(12) United States Patent
Mintz

(10) Patent No.: US 7,176,292 B2
(45) Date of Patent: Feb. 13, 2007

(54) GHRELIN VARIANT PROTEIN

(75) Inventor: Liat Mintz, East Brunswick, NJ (US)

(73) Assignee: Dialean, Ltd. (IL)

( * ) Notice: Subject to any disclaimer, the term of this patent is extended or adjusted under 35 U.S.C. 154(b) by 0 days.

(21) Appl. No.: 10/659,782

(22) Filed: Sep. 11, 2003

(65) Prior Publication Data

US 2005/0059015 A1  Mar. 17, 2005

(51) Int. Cl.
A61K 38/22 (2006.01)
C07K 14/00 (2006.01)
C07H 21/04 (2006.01)

(52) U.S. Cl. .................. 530/399; 930/20; 930/120; 536/23.51

(58) Field of Classification Search ............... 530/350, 530/397, 399, 300
See application file for complete search history.

(56) References Cited

U.S. PATENT DOCUMENTS 6,291,653 B1 * 9/2001 Sheppard et al. ...... 530/388.24
6,838,438 B2   1/2005 Sheppard et al.
6,967,237 B2  11/2005 Bednarek

OTHER PUBLICATIONS

Gualillo et al. Ghrelin, a novel placental-derived hormone. Endocrinology. vol. 142, No. 2, pp. 788-794, Feb. 2001.*
Bednarek et al. Structure-function studies on the new growth hormone-releasing peptide, ghrelin: minimal sequence of ghrelin necessary for activation of growth hormone secretagogue receptor 1a. J Med Chem. vol. 43, No. 23, pp. 4370-4376, Nov. 2000.*
Root et al. Clinical pharmacology of human growth hormone and its secretagogues. Curr Drug Targets Immune Endocr Metabol Disord. vol. 2, No. 1, pp. 27-52, Apr. 2002.*
Bednarek et al. Structure-function studies on the new growth hormone-releasing peptide, ghrelin: minimal sequence of ghrelin necessary for activation of growth hormone secretagogue receptor 1a. J Med Chem. vol. 43, No. 23, pp. 4370-4376, Nov. 2000.*
Muccioli et al. Neuroendocrine and peripheral activities of ghrelin: implications in metabolism and obesity. Eur J Pharmacol. vol. 440, No. 2-3, pp. 235-254, Apr. 2002.*
Broglio et al. Natural and synthetic growth hormone secretagogues: do they have therapeutic protential? Treat Endocrinol. vol. 2, No. 3, pp. 153-163, 2003.*

A. Asakawa, et al., Antagonism of ghrelin receptor reduces food intake and body weight gain in mice, Gut 2003:52:947-952.
Masayasu Kojima et al., Ghrelin is a growth-hormone-releasing acylated peptide from stomach, Nature, vol. 402, Dec. 9, 1999, pp. 656-660.
Hiroshi Hosoda et al., Purification and Characterization of Rat des-Gin14-Ghrelin . . . , J. Biol. Chem., vol. 275, No. 29, Issue of Jul. 21, pp. 21995-22000, 2000.
Mitsuyo Shintani et al., Ghrelin, and Endengenous Growth Hormone Secretagogue . . . , Diabetes, vol. 50, Feb. 2001, pp. 227-232.
P L Jeffery et al., Expression and action of the growth hormone releasing peptide ghrelin . . . , Journal of Endocrinology (2002) 172, Feb 8, 2002, pp. R7-R11.
Minoru Tanaka et al., Testis-specific and developmentally induced expression of a ghrelin . . . , Biochimica et Biophysica Acta, 1522 (2001) pp. 62-65.
L. Trudel et al., Ghrelin/motilin-related peptide is a potent prokinetic to reverse gastric postoperative ileus . . . , Am J Physiol Gastro Liver Physiol 282: G948-G952, 2002.
Anke Hinney et al., Ghrelin gene: Identification of missense variants and a frameshift mutation . . . , J of Clinical Endocrinology & Metabolism 87(6): 2716-2719 (2002).
Marta Korbonits et al., A variation in the ghrelin gene increases weight and decreases . . . , J of Clinical Endocrinology & Metabolism 87(8): 4005-4008 (2002).
Olavi Ukkola et al., Role of Ghrelin Polymorphisms in Obesity Based on Three Different Studies, Obesity Research vol. 10 No. 8 Aug. 2002 pp. 782-791.
Antonio Torsello et al., Short Ghrelin Peptides Neither Displace Ghrelin Binding In Vitro . . . , Endocrinology 143(5):1968-1971 (2002).
David E. Cummings et al., A Preprandial Rise in Plasma Ghrelin Levels Suggests . . . , Diabetes, vol. 50, pp. 1714-1719, Aug. 2001.
Kazuhiro Kawamura et al., Ghrelin Inhibits the Development of Mouse Preimplantation . . . , Endocrinology 144(6):2623-2633 (2003).
A.M. Wren et al., The Novel Hypothalamic Peptide Ghrelin Stimulates Food Intake . . . , Endocrinology vol. 141, No. 11, pp. 4325-4328 (2000).

* cited by examiner

Primary Examiner—Celine Qian
Assistant Examiner—Jennifer Dunston
(74) Attorney, Agent, or Firm—Potter Anderson & Corroon LLP; Jeffrey Safran

(57) ABSTRACT

The present invention concerns a protein produced from an alternative splice form of the human Ghrelin gene, an obesity and/or diabetes related gene.

2 Claims, 17 Drawing Sheets

Fig 1.

```
SEQID22    MLLLGAVLLLLALPGHDQETTTQGPGVLLPLPKGACTGWMAGIPGHPGHNGAPGRDGRDG 60
SEQID23    ------------------------------------------------------------
SEQID24    MLLLGAVLLLLALPGHDQETTTQGPGVLLPLPKGACTGWMAGIPGHPGHNGAPGRDGRDG 60
SEQID25    MLLLGAVLLLLALPGHDQETTTQGPGVLLPLPKGACTGWMAGIPGHPGHNGAPGRDGRDG 60

SEQID22    TPGEKGEKGDPGLIGPKGDIGETGVPGAEGPRGFPGIQGRKGEPGEGAYVYRSAFSVGLE 120
SEQID23    ------------------------MPGAEGPRGFPGIQGRKGEPGEGAYVYRSAFSVGLE 36
SEQID24    TPGEKGEKGDPGLIGPKGDIGETGVPGAEGPRGFPGIQGRKGEPGEGA------------ 108
SEQID25    TPGEKGEKGDPGLIGPKGDIGETGVPGAEGPRGFPGIQGRKGEPGEGAYVYRSAFSVGLE 120

SEQID22    TYVTIPNMPIRFTKIFYNQQNHYDGSTGKFHCNIPGLYYFAYHITVYMKDVKVSLFKKDK 180
SEQID23    TYVTIPNMPIRFTKIFYNQQNHYDGSTGKFHCNIPGLYYFAYHITVYMKDVKVSLFKKDK 96
SEQID24    ------------------------------------------------------------ 108
SEQID25    TYVTIPNMPIRFTKIFYNQQNHYDGSTGKFHCNIPGLY---------------------- 158

SEQID22    AMLFTYDQYQENNVDQASGSVLLHLEVGDQVWLQVYGEGERNGLYAD--NDND-STFTGF 237
SEQID23    AMLFTYDQYQENNVDQASGSVLLHLEVGDQVWLQVYGEGERNGLYAD--NDND-STFTGF 153
SEQID24    ----------------------LLS-PTCPFALPRSSTISKTTMMAP--LVNSTATFLGC 143
SEQID25    ------------------------------------------------------------ 158

SEQID22    LLYHDTN---------- 244
SEQID23    LLYHDTN---------- 160
SEQID24    T----T-LP-TTSQSI- 153
SEQID25    ---------LHRLSSLP 166
```

Fig 2.

```
SEQID28    MLLLQALLFLLILPSHAEDDVTTTEELAPALVPPPKGTCAGWMAGIPGHPGHNGTPGRDG 60
SEQID30    MLLLQALLFLLILPSHAEDDVTTTEELAPALVPPPKGTCAGWMAGIPGHPGH-------- 52
SEQID29    MLLLQALLFLLILPSHAEDDVTTTEELAPALVPPPKGTCAGWMAGIPGHPGHNGTPGRDG 60
SEQID26    MLLLQALLFLLILPSHAEDDVTTTEELAPALVPPPKGTCAGWMAGIPGHPGHNGTPGRDG 60
SEQID27    ------------------------------------------------------------

SEQID28    ---TPGEKGEKGDAGLLGPKGETGDVGMTGAEGPRGFPGTPGRKGEPGEAA-----AASL 113
SEQID30    ------------------------------------------------------------ 52
SEQID29    ---TPGEKGEKGDAGLLGPKGETGDVGMTGAEGPRGFPGTPGRKGEPGEAAY-------- 110
SEQID26    RDGTPGEKGEKGDAGLLGPKGETGDVGMTGAEGPRGFPGTPGRKGEPGEAAYMYRSAFSV 120
SEQID27    ---------------------------MTGAEGPRGFPGTPGRKGEPGEAAYVYRSAFSV 33

SEQID28    ------------------------------------------------------------ 109
SEQID30    ------------------------------------------------------------ 52
SEQID29    ------------------------------------------------------------ 110
SEQID26    GLETRVTVPNVPIRFTKIFYNQQNHYDGSTGKFYCNIPGLYYFSYHITVYMKDVKVSLFK 180
SEQID27    GLETRVTVPNVPIRFTKIFYNQQNHYDGSTGKFYCNIPGLYYFSYHITVYMKDVKVSLFK 93

SEQID28    --------------------------------------------------------FPMYP 118
SEQID30    ----------------IKIK-------FEGHP-----PG--------------------- 63
SEQID29    --------------------------------------------VYRSAFSVGLETRVTVP 129
SEQID26    KDKAVLFTYDQYQEKNVDQA--------SGSVLLHLEVGDQVWLQ--------------- 217
SEQID27    KDKAVLFTYDQYQEKNVDQA--------SGSVLLHLEVGDQVWLQ--------------- 130

SEQID28    FALLRSSTTNRIIMTAALASSTATFRDSTTSLTTSRCT--- 156
SEQID30    --RLNCAKIWHFLQD------------------------- 76
SEQID29    NVPIRFTKIFYNQQN-HYDGSTGKFYCNIPGLYIYWLSSLP 169
SEQID26    --VYGDGDHNGLYADNVNDSTFTGFLLYHDTN--------- 247
SEQID27    --VYGDGDHNGLYADNVNDSTFTGFLLYHDTN--------- 160
```

Fig 3.

```
SEQID31    MPSPGTVCSLLLLGMLWLDLAMAGSSFLSPEHQRVQQRKESKKP---------------- 44
SEQID32    MPSPGTVCSLLLLGMLWLDLAMAGSSFLSPEHQRVQVRPPHKAP------------HVV 47

SEQID31    PAKLQPRALAGWLRPEDGGQAEGAEDELEVRFNAPFDVGIKLSGVQYQQHSQALGKFLQD 104
SEQID32    PALPLSNQLCDLEQQRHWASVFSQSTKDSGSDLTVSGRTWGLRV---------------- 91

SEQID31    ILWEEAKEAPADK------------ 117
SEQID32    LNRLFPPSSRERSRRSHQPSCSPEL 116
```

Fig 4.

```
SEQID33    MAFMKKYLLPILGLFMAYYYYSANEEFRPEMLQGKKVIVTGASKGIGREMAYHLAKMGAH 60
SEQID38    ------------------------------MLQGKKVIVTGASKGIGREMAYHLAKMGAH 30
SEQID36    MAFMKKYLLPILGLFMAYYYYSANEEFRPEMLQGKKVIVTGASKGIGREMAYHLAKMGAH 60
SEQID35    MAFMKKYLLPILGLFMAYYYYSANEEFRPEMLQGKKVIVTGASKGIGREMAYHLAKMGAH 60
SEQID37    MAFMKKYLLPILGLFMAYYYYSANEEFRPEMLQGKKVIVTGASKGIGREMAYHLAKMGAH 60
SEQID39    MAFMKKYLLPILGLFMAYYYYSANEEFRPEMLQGKKVIVTGASKGIGREMAYHLAKMGAH 60
SEQID34    MAFMKKYLLPILGLFMAYYYYSANEEFRPEMLQGKKVIVTGASKGIGREMAYHLAKMGAH 60

SEQID33    VVVTARSKETLQKVVSHCLELGAASAHYIAGTMEDMTFAEQFVAQAGKLMGGLDMLILNH 120
SEQID38    VVVTARSKETLQKVVSHCLELGAASAHYIAGTMEDMTFAEQFVAQAGKLMGGLDMLILNH 90
SEQID36    VVVTARSKETLQKVVSHCLELGAASAHYIAGTMEDMTFAEQFVAQAGKLMGGLDMLILNH 120
SEQID35    VVVTARSKETLQKVVSHCLELGAASAHYIAGTMEDMTFAEQFVAQAGKLMGGLDMLILNH 120
SEQID37    VVVTASS----------------AHYIAGTMEDMTFAEQFVAQAGKLMGGLDMLILNH 102
SEQID39    VVVTARSKETLQKVVSHCLELGAASAHYIAGTMEDMTFAEQFVAQAGKLMGGLDMLILNH 120
SEQID34    VVVTASS----------------AHYIAGTMEDMTFAEQFVAQAGKLMGGLDMLILNH 102

SEQID33    ITNTSLNLFHDDIHHVRKSMEVNFLSYVVLTVAALPMLKQSNGSIVVVSSLAGKVAYPMV 180
SEQID38    ITNTSLNLFHDDIHHVRKSMEVNFLSYVVLTVAALPMLKQSNGSIVVVSSLAGKVAYPMV 150
SEQID36    ITNTSLNLFHDDIHHVR------------------PMLKQSNGSIVVVSSLAGKVAYPMV 162
SEQID35    ITNTSLNLFHDDIHHVRKSMEVNFLSYVVLTVAALPMLKQSNGSIVVVSSLAGKVAYPMV 180
SEQID37    ITNTSLNLFHDDIHHVRKSMEVNFLSYVVLTVAALPMLKQSNGSIVVVSSLAGKVAYPMV 162
SEQID39    ITNTSLNLFHDDIHHVRKSMEVNFLSYVVLTVAALPMLKQSNGSIVVVSSLA-------- 172
SEQID34    ITNTSLNLFHDDIHHVRKSMEVNFLSYVVLTVAALPMLKQSNGSMCAL------------ 150

SEQID33    AAYSASKFALDGFFSSIRKEYSVSRVNVSITLCVLGLIDTETAMKAVSGIVHMQAAPKEE 240
SEQID38    AAYSASKFALDGFFSSIRKEYSVSRVNVSITLCVLGLIDTETAMKAVSGIVHMQAAPKEE 210
SEQID36    AAYSASKFALDGFFSSIRKEYSVSRVNVSITLCVLGLIDTETAMKAVSGIVHMQAAPKEE 222
SEQID35    AAYSASKFALDGFFSSIRKEYSVSRVNVSITLCVLGLIDTETAMKAVSGIVHMQAAPKEE 240
SEQID37    AAYSASKFALDGFFSSIRKEYSVSRVNVSITLCVLGLIDTETAMKAVSGIVHMQAAPKEE 222
SEQID39    --------------------------------ETAMKAVSGIVHMQAAPKEE 192
SEQID34    ----------------------------------------LLECYHVVHLSSX---- 163

SEQID33    CALEIIKGGALRQEEVYYDSSLWTTLLIRNPCRKILEFLYSTSYNMDRFINK--- 292
SEQID38    CALEIIKGGALRQEEVYYDSSLWTTLLIRNPCRKILEFLYSTSYNMDRFINK--- 262
SEQID36    CALEIIKGGALRQEEVYYDSSLWTTLLIRNPCRKILEFLYSTSYNMDRFINK--- 274
SEQID35    CALEIIKGGALRQEEVYYDSSLWTTLLIRNPCRKILEFLYSTSYNMEGLFCLMFI 295
SEQID37    CALEIIKGGALRQEEVYYDSSLWTTLLIRNPCRKILEFLYSTSYNMDRFINK--- 274
SEQID39    CALEIIKGGALRQEEVYYDSSLWTTLLIRNPCRKILEFLYSTSYNMDRFINK--- 244
SEQID34    ------------------------------------------------------
```

Fig 5.

```
SEQID40       MAVMKNYLLPILVLFLAYYYYSTNEEFRPEMLQGKKVIVTGASKGIGREMAYHLSKMGAH  60
SEQID41       MAVMKNYLLPILVLFLAY------------------------------------------  18
SEQID42       MAVMKNYLLPILVLFLAYYYYSTNEEFRPEMLQGKKVIVTGASKGIGREMAYHLSKMGAH  60

SEQID40       VVLTARSEEGLQKVVSRCLELGAASAHYIAGTMEDMTFAEQFIVKAGKLMGGLDMLILNH  120
SEQID41       YYYSTNEEFRLQKVVSRCLELGAASAHYIAGTMEDMTFAEQFIVKAGKLMGGLDMLILNH   78
SEQID42       VVLTARSEEGLQKVVSRCLELGAASAHYIAGTMEDMTFAEQFIVKAGKLMGGLDMLILNH  120

SEQID40       ITQTSLSLFHDDIHSVRRVMEVNFLSYVVMSTAALPMLKQSNGSIAVISSLAGKMTQPMI  180
SEQID41       ITQTSLSLFHDDIHSVRRVMEVNFLSYVVMSTAALPMLKQSNGSIAVISSLAGKMTQPMI  138
SEQID42       ITQTSLSLFHDDIHSVRRVMEVNFLSYVVMSTAALPMLKQSNGSIAVISSLAGGRTVPQQ  180

SEQID40       APYSASKFALDGFFSTIRTELYITKVNVSITLCVLGLIDTETAMKEISGIINAQASPKEE  240
SEQID41       APYSASKFALDGFFSTIRTELYITKVNVSITLCVLGLIDTETAMKEISGIINAQASPKEE  198
SEQID42       RSRSVTPDSRGP------------------------------------------------  192

SEQID40       CALEIIKGTALRKSEVYYDKSPLTPILLGNPGRKIMEFFSLRYYNKDMFVSN  292
SEQID41       CALEIIKGTALRKSEVYYDKSPLTPILLGNPGRKIMEFFSLRYYNKDMFVSN  250
SEQID42       ----------------------------------------------------
```

Fig 6. (1 of 2)

```
SEQID1    CTGATTCCATACCAGAGGGGCTCAGGATGCTGTTGCTGGGAGCTGTTCTACTGCTATTAG
SEQID2    ------------------------------------------------------------
SEQID3    ------------------------------------------------------------
SEQID4    ------------------------------------------------------------

SEQID1    CTCTGCCCGGGCATGACCAGGAAACCACGACTCAAGGGCCCGGAGTCCTGCTTCCCCTGC
SEQID2    ------------------------------------------------------------
SEQID3    ------------------------------------------------------------
SEQID4    ------------------------------------------------------------

SEQID1    CCAAGGGGGCCTGCACAGGTTGGATGGCGGGCATCCCAGGGCATCCGGGCCATAATGGGG
SEQID2    ------------------------------------------------------------
SEQID3    ------------------------------------------------------------
SEQID4    ------------------------------------------------------------

SEQID1    CCCCAGGCCGTGATGGCAGAGATGGCACCCCTGGTGAGAAGGGTGAGAAAGGAGATCCAG
SEQID2    ----------------------------ATG-----------------------------
SEQID3    -----------------------CTGATTCCAT---------------------------
SEQID4    -----------------------CTGATTCCAT---------------------------
                                  **

SEQID1    GTCTTATTGGTCCTAAGGGAGACATCGGTGAAACCGGAGTACCCG--GGGCTGAAGGTCC
SEQID2    ---------------------------------------ACCCG--GGGCTGAAGGTCC
SEQID3    ---------------------------------------ACCAGAGGGGCTCAGGATGC
SEQID4    ---------------------------------------ACCAGAGGGGCTCAGGATGC
                                                  ***  *  ***** * * * *

SEQID1    -----CCGAG-GCT-TTC--CGGG-AAT-------CCAAGGCAGGAA-AGGAGAACCTGG
SEQID2    -----CCGAG-GCT-TTC--CGGG-AAT-------CCAAGGCAGGAA-AGGAGAACCTGG
SEQID3    TGTTGCTGGGAGCTGTTCTACTGCTATTAGCTCTGCCCGGGCATGACCAGGA-AACCACG
SEQID4    TGTTGCTGGGAGCTGTTCTACTGCTATTAGCTCTGCCCGGGCATGACCAGGA-AACCACG
              *  * *** ***  *  *  *    **  **** **  **** ****  *

SEQID1    A--GAAGGTGCCTATGTA----TACCGCT---CA------GCATTCAGTG-TGGGATTGGA
SEQID2    A--GAAGGTGCCTATGTA----TACCGCT---CA------GCATTCAGTG-TGGGATTGGA
SEQID3    ACTCAAGGGCCCGGAGTCCTGCTTCCCCTGCCCAAGGGGGCCTGCACAGGTTGGATGGCG
SEQID4    ACTCAAGGGCCCGGAGTCCTGCTTCCCCTGCCCAAGGGGGCCTGCACAGGTTGGATGGCG
           *  ****  **  **     *  **  **       ** *  **   * *  ****  *

SEQID1    GACTTACGTTACTATCC---CCAACATG----CCCATTCGCT--TTACCAAGAT------
SEQID2    GACTTACGTTACTATCC---CCAACATG----CCCATTCGCT--TTACCAAGAT------
SEQID3    GGCATCCCAGGGCATCCGGGCCATAATGGGGCCCCAGGCCGTGATGGCAGAGATGGCACC
SEQID4    GGCATCCCAGGGCATCCGGGCCATAATGGGGCCCCAGGCCGTGATGGCAGAGATGGCACC
          * * *           ****  ***  ***  ****    *   *    *     ****

SEQID1    -CTTCT-ACAA---TCAGCAA----AACCAC-TATGATGGCTCCACTGGTAAATTCCACT
SEQID2    -CTTCT-ACAA---TCAGCAA----AACCAC-TATGATGGCTCCACTGGTAAATTCCACT
SEQID3    CCTGGTGAGAAGGGTGAGAAAGGAGATCCAGGTCTTATTGGTCCTAAGGGAGACATCGGT
SEQID4    CCTGGTGAGAAGGGTGAGAAAGGAGATCCAGGTCTTATTGGTCCTAAGGGAGACATCGGT
           **  *   * **   *  * **      ***   * *  *  *     **   *  *

SEQID1    GCAAC---ATT--CCTGGGCTGTA---CTACTTTGCCTACCACATCACAGTCTATATGAA
SEQID2    GCAAC---ATT--CCTGGGCTGTA---CTACTTTGCCTACCACATCACAGTCTATATGAA
SEQID3    GAAACCGGAGTACCCGGGGCTGAAGGTCCCCGAGGCTTTCCGGG----AATCCA-AGGCA
SEQID4    GAAACCGGAGTACCCGGGGCTGAAGGTCCCCGAGGCTTTCCGGG----AATCCA-AGGCA
          * ***   * *  * ********    *     **  ***     **  * *   *  *

SEQID1    GGATGTGAAGGTCAGCCTCTTCAAGAAGGACAAGGCTATGC----TCTTCACCTATGATCA
SEQID2    GGATGTGAAGGTCAGCCTCTTCAAGAAGGACAAGGCTATGC----TCTTCACCTATGATCA
SEQID3    GGA----AAGGAGAACCT---------GGAGAAGG---TGC-------------------
SEQID4    GGA----AAGGAGAACCT---------GGAGAAGG---TGCCTATGTATACCGCTCAGCA
          ***    ****  * ***         *** ****   ***

SEQID1    GTACCAGGAAAATAATGTGGACC---AGGCCTCCGGCTCTGTGCTCCTGCATCTGGAGGT
```

FIG. 6 (2 of 2)

```
SEQID2    GTACCAGGAAAATAATGTGGACC---AGGCCTCCGGCTCTGTGCTCCTGCATCTGGAGGT
SEQID3    ----------------------------------GTTACTATCC-CCAACATGCCCATTC
SEQID4    TT--CAG--------TGTGGGATTGGAGACTTACGTTACTATCC-CCAACATGCCCATTC
                                              *  ** * **  ***     *

SEQID1    GGGCGACCAAG-TCTGGCTCCAGGTGTATGGGGAAGGAGAGCGTAATGGACTCTATGCTG
SEQID2    GGGCGACCAAG-TCTGGCTCCAGGTGTATGGGGAAGGAGAGCGTAATGGACTCTATGCTG
SEQID3    GCTTTACCAAGATCTT-CTACA-----ATCAGCAAAACCACTATGATGG-CTCCA--CTG
SEQID4    GCTTTACCAAGATCTT-CTACA-----ATCAGCAAAACCACTATGATGG-CTCCA--CTG
          *  ******  ***  ** **       ** * **     *   * **** ***  * ***

SEQID1    ATAA-TGACAATG----ACTCC--------AC-----------------------------
SEQID2    ATAA-TGACAATG----ACTCC--------AC-----------------------------
SEQID3    GTAAATTCCACTGCAACATTCCTGGGCTGTACTACTTTGCCTACCACATCACAGTCTATA
SEQID4    GTAAATTCCACTGCAACATTCCTGGGCTGTAC----------------------------
          ***  *  ** **       * ***        **

SEQID1    ------------------------------------------------------------
SEQID2    ------------------------------------------------------------
SEQID3    TGAAGGATGTGAAGGTCAGCCTCTTCAAGAAGGACAAGGCTATGCTCTTCACCTATGATC
SEQID4    ------------------------------------------------------------

SEQID1    ------------------------------------------------------------
SEQID2    ------------------------------------------------------------
SEQID3    AGTACCAGGAAAATAATGTGGACCAGGCCTCCGGCTCTGTGCTCCTGCATCTGGAGGTGG
SEQID4    ------------------------------------------------------------

SEQID1    ------------------------------------------------------------
SEQID2    ------------------------------------------------------------
SEQID3    GCGACCAAGTCTGGCTCCAGGTGTATGGGGAAGGAGAGCGTAATGGACTCTATGCTGATA
SEQID4    ------------------------------------------------------------

SEQID1    ---------------CTTCACAGGCTTTCTTCTCTACCATGACACCAACTGATCACCAC
SEQID2    ---------------CTTCACAGGCTTTCTTCTCTACCATGACACCAACTGA-------
SEQID3    ATGACAATGACTCCACCTTCACAGGCTTTCTTCTCTACCATGACACCAACTGA-------
SEQID4    ---------------CTTCACAGGCTTTCTTCTCTACCATGACACCAACTGA-------
                          *************************************

SEQID1    TAACTCAGAGCCTCCTCCAGGCCAAACAGCCCCAAAGTCAATTAAAGGCTTTCAGTACGG
SEQID2    ------------------------------------------------------------
SEQID3    ------------------------------------------------------------
SEQID4    ------------------------------------------------------------

SEQID1    TTAGGAAGTTGATTATTATTTAGTTGGAGGCCTTTAGATATTATTCATTCATTTACTCAT
SEQID2    ------------------------------------------------------------
SEQID3    ------------------------------------------------------------
SEQID4    ------------------------------------------------------------
```

Fig 7. (1 of 3)

```
SEQID5  ATGAGACCTGGCCACTTTCTCCTCATTTCTGTCTGTACGATTGTCAGTGGATCTGACGAC 60
SEQID6  ---------------------------GCTCATTCATCTTTTAATTCA----- 21
SEQID7  ATGAGACCTGGCCACTTTCTCCTCATTTCTGTCTGTACGATTGTCAGTGGATCTGACGAC 60
SEQID8  ------------------------------------------------------------
SEQID9  ------------------------------------------------------------

SEQID5  ACCAAAAGGGCTCAGGATGCTACTGTTGCAAGCTCTCCTGTTCCTCTTAATCCTGCCCAG 120
SEQID6  CCCATAAAGGCTTTGAAAACTAAGGCTGGAGATGAACTTAT-----AGGAGCCTGCCAGG 76
SEQID7  ACCAAAAGGGCTCAGGATGCTACTGTTGCAAGCTCTCCTGTTCCTCTTAATCCTGCCCAG 120
SEQID8  ------------------------------------------------------------
SEQID9  ------------------------------------------------------------

SEQID5  TCATGCCGAAGATGACGTTACTACAACTGAAGAGCTAGCTCCTGCTTTGGTCCCTCCACC 180
SEQID6  CCGTG--GAGAGTGAGGAAGCAGAGATGACGGAGATGATGTCTTTCCTTGTCCTGTGA-- 132
SEQID7  TCATGCCGAAGATGACGTTACTACAACTGAAGAGCTAGCTCCTGCTTTGGTCCCTCCACC 180
SEQID8  ------------------------------------------------------------
SEQID9  ------------------------------------------------------------

SEQID5  CAAGGGAACTTGTGCAGGTTGGATGGCAGGCATCCCAGGACATCCTGGCCACAATGGCAC 240
SEQID6  -AATGGATTGTGGGTAGA---GGTTCCGGAGATAATGCCTCTTGCTGGAAACAGT----- 183
SEQID7  CAAGGGAACTTGTGCAGGTTGGATGGCAGGCATCCCAGGACATCCTGGCCACAATGGCAC 240
SEQID8  ------------------------------------------------------------
SEQID9  ------------------------------------------------------------

SEQID5  ACCAGGCCGTGATGGCAGAGATGGCACTCCTGGAGAGAAGGGAGAGAAAGGAGATGCAGG 300
SEQID6  -CTGGGCAGTTCTGTT---CCCGCCATTC----ACAGAATTCTTCTCACTT---TCTAGG 232
SEQID7  ACCAGGCCGTGATGGCAGAGATGGCACTCCTGGAGAGAAGGGAGAGAAAGGAGATGCAGG 300
SEQID8  ------------------------------------------------------------
SEQID9  ------------------------------------------------------------

SEQID5  TCTTCTTGGTCCTAAGGGTGAGACAGGAGATGTTGGAATGACAGGAGCTGAAGGGCCACG 360
SEQID6  TCTTCTTGGTCCTAAGGGTGAGACAGGAGATGTTGGAATGACAGGAGCTGAAGGGCCACG 292
SEQID7  TCTTCTTGGTCCTAAGGGTGAGACAGGAGATGTTGGAATGACAGGAGCTGAAGGGCCACG 360
SEQID8  ------------------------------------------------------------
SEQID9  ------------------------------------------------------------

SEQID5  GGGCTTCCCCGGAACCCCTGGCAGGAAAGGAGAGCCTGGAGAAGCCGCTTATGTGTATCG 420
SEQID6  GGGCTTCCCCGGAACCCCTGGCAGGAAAGGAGAGCCTGGAGAAGCCGCTTATGTGTATCG 352
SEQID7  GGGCTTCCCCGGAACCCCTGGCAGGAAAGGAGAGCCTGGAGAAGCCGC------------ 408
SEQID8  ------------------------------------------------------------
SEQID9  ------------------------------------------------------------

SEQID5  CTCAGCGTTCAGTGTGGGGCTGGAGACCCGCGTCACTGTTCCCAATGTACCCATTCGCTT 480
SEQID6  CTCAGCGTTCAGTGTGGGGCTGGAGACCCGCGTCACTGTTCCCAATGTACCCATTCGCTT 412
SEQID7  --------------------------GTCACTGTTCCCAATGTACCCATTCGCTT 437
SEQID8  ------------------------------ATGAGACC--TGGCCACTTTCTCCT 23
SEQID9  ------------------------------ATGAGACC--TGGCCACTTTCTCCT 23
                                      **  ** **   *  *  *** *  *

SEQID5  TACTAAGATCTTCTACAACCAACAGAATCATTATGACGGCAGCACTGGCAAGTTCTACTG 540
SEQID6  TACTAAGATCTTCTACAACCAACAGAATCATTATGACGGCAGCACTGGCAAGTTCTACTG 472
SEQID7  TACTAAGATCTTCTACAACCAACAGAATCATTATGACGGCAGCACTGGCAAGTTCTACTG 497
SEQID8  CATTTCTGTCTG-TACGATTGTCAG--TGGATCTGACGACACCAAAAG-GGCTCAGGATG 79
SEQID9  CATTTCTGTCTG-TACGATTGTCAG--TGGATCTGACGACACCAAAAG-GGCTCAGGATG 79
        *  *    *** *** *     ***  *    ** ***** **      *

SEQID5  CAACATTCCGGGACTCTACTACTTCTCTTACCACATCACGGTGTACATGAAAGATGTGAA 600
SEQID6  CAACATTCCGGGACTCTACTACTTCTCTTACCACATCACGGTGTACATGAAAGATGTGAA 532
SEQID7  CAACATTCCGGGACTCTACTACTTCTCTTACCACATCACGGTGTACATGAAAGATGTGAA 557
SEQID8  CTACTGTTGCAAGCTCTCCTGTTCCTCTTAATCCTGCCCAGT---CATGCCGAAGATGAC 136
SEQID9  CTACTGTTGCAAGCTCTCCTGTTCCTCTTAATCCTGCCCAGT---CATGCCGAAGATGAC 136
```

FIG. 7 (2 OF 3)

```
        * **  *    **** **  * ******   *  * **    ****    *  ***
SEQID5  GGTGAGCCTCTTCAAGAAGGACAAGGCCGTTCTCTTCACCTACGACCAGTATCAGGAAAA 660
SEQID6  GGTGAGCCTCTTCAAGAAGGACAAGGCCGTTCTCTTCACCTACGACCAGTATCAGGAAAA 592
SEQID7  GGTGAGCCTCTTCAAGAAGGACAAGGCCGTTCTCTTCACCTACGACCAGTATCAGGAAAA 617
SEQID8  GTTACTACAACT---GAAGAGCTAGCTCCTGCTTTGGTCCCTCCACCCA----AGGGAAC 189
SEQID9  GTTACTACAACT---GAAGAGCTAGCTCCTGCTTTGGTCCCTCCACCCA----AGGGAAC 189
        * *   *   **** *  **** * ** * * **  ** *  ***     *** **

SEQID5  GAATGTGGACCAGGCCTCTGGCTCTGTGCTCCTCCATCTGGAGGTGGGAGACCAAGTCTG 720
SEQID6  GAATGTGGACCAGGCCTCTGGCTCTGTGCTCCTCCATCTGGAGGTGGGAGACCAAGTCTG 652
SEQID7  GAATGTGGACCAGGCCTCTGGCTCTGTGCTCCTCCATCTGGAGGTGGGAGACCAAGTCTG 677
SEQID8  TTGTGCAGGTTGGATGGCAGGCATCCCAGGACATC--CTGGCCACAATG----GCACACC 243
SEQID9  TTGTGCAGGTTGGATGGCAGGCATCCCAGGACATC--CTGGCCACATAA----AAATATA 243
         ** *     *     * ***             *  ****

SEQID5  GCTCCAGGTGTATGGGGATGGGGACCACAATGGACTCTATGCAGATAACGTCAACGACTC 780
SEQID6  GCTCCAGGTGTATGGGGATGGGGACCACAATGGACTCTATGCAGATAACGTCAACGACTC 712
SEQID7  GCTCCAGGTGTATGGGGATGGGGACCACAATGGACTCTATGCAGATAACGTCAACGACTC 737
SEQID8  AGGCCGTGATGGCAGAGA-TGGCACTCCTGGA----GAGAAGGGAGAGAAAGGA-GATGC 297
SEQID9  ATTC---------GAGG-GGCATCCACCAGG----CCGGCTGAATTGTGCCAA-AATAT 287
           *          * *  *   *  *          *             *  *

SEQID5  TACATTTACTGGCTTTCTTCTCTACCATGATACCAACTGACTGCAACTACCCATAGCCCA 840
SEQID6  TACATTTACTGGCTTTCTTCTCTACCATGATACCAACTGACTGCAACTACCCATAGCCCA 772
SEQID7  TACATTTACTGGCTTTCTTCTCTACCATGATACCAACTGACTGCAACTACCCATAGCCCA 797
SEQID8  AGGTCTTCTTGGTCCTAAGGGTGAGACAGGAGATGTTGGAATGACAGGAGCTGAAGGGCC 357
SEQID9  GGCACTTCCTG------CAAGATAA----------------------------------- 306
          ** **           *

SEQID5  TACACCAGGAGAATCATGGAACAGTCGACACACTTTCAGCTTAGTTTGAGAGATTGATTT 900
SEQID6  TACACCAGGAGAATCATGGAACAGTCGACACACTTTCAGCTTAGTTTGAGAGATTGATTT 832
SEQID7  TACACCAGGAGAATCATGGAACAGTCGACACACTTTCAGCTTAGTTTGAGAGATTGATTT 857
SEQID8  ACGGGGCTTCCCCGGAACCCCTGGCAGGAAAGGAGAGCCTGGAGAAGCCGCTTATGTGTA 417
SEQID9  ------------------------------------------------------------

SEQID5  TATTGCTTAGTTTGAGAGTCCTGAGTATTATCCACACGTGTACTCACTTGTTCATTAAAC 960
SEQID6  TATTGCTTAGTTTGAGAGTCCTGAGTATTATCCACACGTGTACTCACTTGTTCATTAAAC 892
SEQID7  TATTGCTTAGTTTGAGAGTCCTGAGTATTATCCACACGTGTACTCACTTGTTCATTAAAC 917
SEQID8  TCGCTCAGCGTTCAGTGTGGGCTGGAGACCCGCGTCACTGTTCCCAATGTACCCATTCG 477
SEQID9  ------------------------------------------------------------

SEQID5  GACTTTATAAAAAATAATTTGTGTTCCTAGTCCAGAAAAAAAGGCACTCCCTGGTCTCCA 1020
SEQID6  GACTTTATAAAAAATAATTTGTGTTCCTAGTCCAGAAAAAAAGGCACTCCCTGGTCTCCA 952
SEQID7  GACTTTATAAAAAATAATTTGTGTTCCTAGTCCAGAAAAAAAGGCACTCCCTGGTCTCCA 977
SEQID8  CTTTACTAAGATCTTCTACAACCAACAGAATCATTATGACGGCAGCACTGGCAAGTTCTA 537
SEQID9  ------------------------------------------------------------

SEQID5  CGACTCTTACATGGTAGCAATAACAGAATGAAAATCACATTTGGTATGGGGGCTTCACAA 1080
SEQID6  CGACTCTTACATGGTAGCAATAACAGAATGAAAATCACATTTGGTATGGGGGCTTCACAA 1012
SEQID7  CGACTCTTACATGGTAGCAATAACAGAATGAAAATCACATTTGGTATGGGGGCTTCACAA 1037
SEQID8  CTGCAACATTCCGGGACTCTACATTTACTGGCTTTCTTCTCTACCATGATACCAACTGAC 597
SEQID9  ------------------------------------------------------------

SEQID5  TATTCGCATGACTGTCTGGAAGTAGACCATGCTATTTTTCTGCTCACTGTACACAAATAT 1140
SEQID6  TATTCGCATGACTGTCTGGAAGTAGACCATGCTATTTTTCTGCTCACTGTACACAAATAT 1072
SEQID7  TATTCGCATGACTGTCTGGAAGTAGACCATGCTATTTTTCTGCTCACTGTACACAAATAT 1097
SEQID8  TGCAACTACCCATAGCCCATACACCAGGAGAATCATGGAACAGTCGACACACTTTCAGCT 657
SEQID9  ------------------------------------------------------------

SEQID5  TGTTCACATAAACCCTATAATGTAAATATGAAATACAGTGATTACTCTTCTCACAGGCTG 1200
SEQID6  TGTTCACATAAACCCTATAATGTAAATATGAAATACAGTGATTACTCTTCTCACAGGCTG 1132
SEQID7  TGTTCACATAAACCCTATAATGTAAATATGAAATACAGTGATTACTCTTCTCACAGGCTG 1157
SEQID8  TAGTTTGAGAGATTGATTTTATTGCTTAGTTTGAGAGTCCTGAGTATTATCCACACGTGT 717
SEQID9  ------------------------------------------------------------
```

FIG. 7 (3 OF 3)

```
SEQID5    ASTGTATGAATTCTAAAGACCCATAAGTATTAAAGTGGTAGGGATAAATTGGAAAAAAAA 1260
SEQID6    AGTGTATGAATTCTAAAGACCCATAAGTATTAAAGTGGTAGGGATAAATTGG-------- 1184
SEQID7    AGTGTATGAATTCTAAAGACCCATAAGTATTAAAGTGGTAGGGATAAATTGG-------- 1209
SEQID8    ACTCACTTGTTCATTAAACGACTTTATAAAAAATAATTTGTGTTCCTAGTCCAGAAAAAA 777
SEQID9    ------------------------------------------------------------

SEQID5    AAAAAAAAAAAGAAAAACTTTAGAGCACACTGGCGGCCGTTACTAG-------------- 1306
SEQID6    ------------------------------------------------------------
SEQID7    ------------------------------------------------------------
SEQID8    AGGCACTCCCTGGTCTCCACGACTCTTACATGGTAGCAATAACAGAATGAAAATCACATT 837
SEQID9    ------------------------------------------------------------

SEQID5    ------------------------------------------------------------
SEQID6    ------------------------------------------------------------
SEQID7    ------------------------------------------------------------
SEQID8    TGGTATGGGGGCTTCACAATATTCGCATGACTGTCTGGAAGTAGACCATGCTATTTTTCT 897
SEQID9    ------------------------------------------------------------

SEQID5    ------------------------------------------------------------
SEQID6    ------------------------------------------------------------
SEQID7    ------------------------------------------------------------
SEQID8    GCTCACTGTACACAAATATTGTTCACATAAACCCTATAATGTAAATATGAAATACAGTGA 957
SEQID9    ------------------------------------------------------------

SEQID5    ------------------------------------------------------------
SEQID6    ------------------------------------------------------------
SEQID7    ------------------------------------------------------------
SEQID8    TTACTCTTCTCACAGGCTGAGTGTATGAATTCTAAAGACCCATAAGTATTAAAGTGGTAG 1017
SEQID9    ------------------------------------------------------------

SEQID5    ----------
SEQID6    ----------
SEQID7    ----------
SEQID8    GGATAAATTGG 1028
SEQID9    ----------
```

Fig 8.

```
SEQID10     ACTCTGGATGGGTGCTGTTTAGACAAACGCCGTCTCCTATATAAGACCTGACAGCACAGG  60
SEQID11     ACTCTGGATGGGTGCTGTTTAGACAAACGCCGTCTCCTATATAAGACCTGACAGCACAGG  60
            ************************************************************

SEQID10     CACCACTCCGCCAGGACTGCAGGCCCACCTGTCTGCAACCCAGCTGAGGCCATGCCCTCC  120
SEQID11     CACCACTCCGCCAGGACTGCAGGCCCACCTGTCTGCAACCCAGCTGAGGCCATGCCCTCC  120
            ************************************************************

SEQID10     CCAGGGACCGTCTGCAGCCTCCTGCTCCTCGGCATGCTCTGGCTGGACTTGGCCATGGCA  180
SEQID11     CCAGGGACCGTCTGCAGCCTCCTGCTCCTCGGCATGCTCTGGCTGGACTTGGCCATGGCA  180
            ************************************************************

SEQID10     GGCTCCAGCTTCCTGAGCCCTGAACACCAGAGAGTCCAGCAGAGAAAGGAGTCGAAGAAG  240
SEQID11     GGCTCCAGCTTCCTGAGCCCTGAACACCAGAGAGTCCAG--GTGAGACCTCCCCACAAAG  238
            ***************************************  * **     * *  ***

SEQID10     CCACCAGCCAAGCTGCAGCCCCGAGCTCTAGCAGGCTGGCTCCGCCCGGAAGATGGAGGT  300
SEQID11     CCCCACATGTTGTTCCAGCCCTGCCACTTAGCAA-CCAGCTCTGT---------GACCT  287
            ** *        * * ****** *     ***** *    **** *         ** *

SEQID10     CAAGCAGAAGGGGCAGAGGATGAACTGGAAGTCCGGTTCAACGCCCCCTTTGATGTTGGA  360
SEQID11     GGAGCAGCAGCGCCATCTC-TGGGCTTCA-GTCTTCTCCCAGAGCACAAAGGACTCTGGG  345
            * **** **   *   **  ***  ***  *** **    *  *      **  * ***

SEQID10     ATCAAGCTGTCAGGGGTTCAGTACCAGCAGCACAGCC--AGGCCCTGGGGAAGTTTCTTC  418
SEQID11     TCTGACCT--CACTGTTTCTGGAAGGACATGGGGGCTTAGAGTCCTAAACAGACTGTTTC  403
             *  **    ** * *** * ***    *  *   *    *   ***    * * ***

SEQID10     AGGACATCCTCTGGGAAGAG-GCCAAAGAGGCCCCAGCCGACAAGTGATCGCCCACAAGC  477
SEQID11     CCCCTTCCAGCAGAGAAAGGAGTCGAAGAAGCC--ACCAGCCAAGCTGCAGCCC-CGAGC  460
                * *  ***    *  *    * *  ****  *   *  *   *** *    ***

SEQID10     CTTACTCACCTCTCTCTAAGTTTAGAAGCGCTCATCTGGCTTTTCGCTTGCTTCTGCAGC  537
SEQID11     TCTAGCAGGCTGGCTCC--GCCCGGAAGA-------TGGA---------GGTCAAGCAGA  502
             **   **  *** ***   *  ** ****    ***       *  *   ****

SEQID10     AACTCCCACGACTGTTGTACAAGCTCAGGAGGCGAATAAATGTTCAAACTGTATGCTGAT  597
SEQID11     AGGGGCAGAGGATGAACTGGAAGTCCGGG---TCGGTACCTCTGCAG-TTTTATGCTTCT  558
            *    *   *   **  *  *** * ***    **  * ** *  *** ****** *

SEQID10     GTTCCAAATGGGAATTTATTTCAAAGAGGAAAAGTTAATATTTTACTTTAAAAAAATCAA  657
SEQID11     GTGGCAGCGAGGAGGGTGGGG---------------------------------------  579
            **  **   ***    *

SEQID10     AATAATAC  665
SEQID11     --------
```

Fig 9. (1 of 4)

```
SEQID15  ------------------------------------------------------------
SEQID17  GGTGAAAAGGGAAAACCTGCCCAAATCCAGTTTTTGTTTCAGTAACTTCCTTTGAGACAA  60
SEQID16  ------------------------------------------------------------
SEQID12  ------------------------------------------------------------
SEQID14  ------------------------------------------------------------
SEQID18  ------------------------------------------------------------
SEQID13  ------------------------------------------------------------

SEQID15  ------------------------------------------------------------
SEQID17  AGTCAGGAATCTGAGAGTAAGCACCTGCTAAGGGTGGGACAGGGGCTCTGTCTGGTATGC  120
SEQID16  ------------------------------------------------------------
SEQID12  ------------------------------------------------------------
SEQID14  ------------------------------------------------------------
SEQID18  ------------------------------------------------------------
SEQID13  ------------------------------------------------------------

SEQID15  ------------------------------------------------------------
SEQID17  CTCTCCCATGTTAAGAGCTAACAATAGTAATGGATAAGTCTCCAGGGCAACCAGGACCAC  180
SEQID16  ------------------------------------------------------------
SEQID12  ------------------------------------------------------------
SEQID14  ------------------------------------------------------------
SEQID18  ------------------------------------------------------------
SEQID13  ------------------------------------------------------------

SEQID15  ------------------------------------------------------------
SEQID17  TTCCAAGCATTCCTGTCTTGGGCTGCCTCGAGGGCTCCTCTGTCCTTTGGGGAGTACTGA  240
SEQID16  ------------------------------------------------------------
SEQID12  ------------------------------------------------------------
SEQID14  ------------------------------------------------------------
SEQID18  ------------------------------------------------------------
SEQID13  ------------------------------------------------------------

SEQID15  ------------------------------------------------------------
SEQID17  TTGATGCCTGATGCCCAGAACTGGCCCACTCTGGCTTCTCTTTGGAGCTGTCTCTGCAGG  300
SEQID16  ------------------------------------------------------------
SEQID12  ------------------------------------------------------------
SEQID14  ------------------------------------------------------------
SEQID18  ------------------------------------------------------------
SEQID13  ------------------------------------------------------------

SEQID15  ---------------------------------------------------------GCA  3
SEQID17  CGCCTTCTGGCTGCCAGCTCGGTCCTAGCATAAGGGACTTCTTCCTTGGCCTGGGTTTCA  360
SEQID16  ---------------------------------------------------------GCA  3
SEQID12  ---------------------------------------------------------GCA  3
SEQID14  ---------------------------------------------------------GCA  3
SEQID18  ---------------------------------------------------------GCA  3
SEQID13  ---------------------------------------------------------GCA  3
                                                                  **

SEQID15  CTGCCTGAGACTACTC--CAGCCTCCCCCGTCCCTGATGTCACAATTCAGAGGCTGCTGC  61
SEQID17  CCTTCTTGTATCAGGTGGCAGACCAGCTGGTTTCAG---TCCAAATCAG-GTCTTCTGA   416
SEQID16  CTGCCTGAGACTACTC--CAGCCTCCCCCGTCCCTGATGTCACAATTCAGAGGCTGCTGC  61
SEQID12  CTGCCTGAGACTACTC--CAGCCTCCCCCGTCCCTGATGTCACAATTCAGAGGCTGCTGC  61
SEQID14  CTGCCTGAGACTACTC--CAGCCTCCCCCGTCCCTGATGTCACAATTCAGAGGCTGCTGC  61
SEQID18  CTGCCTGAGACTACTC--CAGCCTCCCCCGTCCCTGATGTCACAATTCAGAGGCTGCTGC  61
SEQID13  CTGCCTGAGACTACTC--CAGCCTCCCCCGTCCCTGATGTCACAATTCAGAGGCTGCTGC  61
         *  **   *  *    *** *     ** *  *   ** *** **** *  ** ***

SEQID15  CTGCTTAGGAGGTTGTAGAAAGCTCTG--TAGGTTCTCTCTGTGTGTCCTACAGGAGTCT  119
SEQID17  CTCCTCCCAGAAACCAACCAACTTCTGAGCAGGAAATC-CTGCCCCTCCCCAAAGAGTGG  475
SEQID16  CTGCTTAGGAGGTTGTAGAAAGCTCTG--TAGGTTCTCTCTGTGTGTCCTACAGGAGTCT  119
SEQID12  CTGCTTAGGAGGTTGTAGAAAGCTCTG--TAGGTTCTCTCTGTGTGTCCTACAGGAGTCT  119
```

FIG. 9 (2 of 4)

```
SEQID14    CTGCTTAGGAGGTTGTAGAAAGCTCTG--TAGGTTCTCTCTGTGTGTCCTACAGGAGTCT 119
SEQID18    CTGCTTAGGAGGTTGTAGAAAGCTCTG--TAGGTTCTCTCTGTGTGTCCTACAGGAGTCT 119
SEQID13    CTGCTTAGGAGGTTGTAGAAAGCTCTG--TAGGTTCTCTCTGTGTGTCCTACAGGAGTCT 119
           ** **                *  **  ****    ***  ** ***   ***  * ****

SEQID15    TCAG--GCCAGCTCCCTGTCGGATGGCTTTTATGAAAAAATATCTCCTCCCCATTCTGGG 177
SEQID17    GAAACCGCAAAGGAAGAGAGAGATGAAACAGAAGGAAAGGCAGAGGAGGAGGGAGAGAGA 535
SEQID16    TCAG--GCCAGCTCCCTGTCGGATGGCTTTTATGAAAAAATATCTCCTCCCCATTCTGGG 177
SEQID12    TCAG--GCCAGCTCCCTGTCGGATGGCTTTTATGAAAAAATATCTCCTCCCCATTCTGGG 177
SEQID14    TCAG--GCCAGCTCCCTGTCGGATGGCTTTTATGAAAAAATATCTCCTCCCCATTCTGGG 177
SEQID18    TCAG--GCCAGCTCCCTGTCGGATGGCTTTTATGAAAAAATATCTCCTCCCCATTCTGGG 177
SEQID13    TCAG--GCCAGCTCCCTGTCGGATGGCTTTTATGAAAAAATATCTCCTCCCCATTCTGGG 177
             *  **  *       *    ****    *  ***    *               *

SEQID15    GCTCTTCATGGCCTACTACTACTATTCTGCAA-ACGAGGAATTCAGACC------------ 225
SEQID17    GAGAAGAGAAGAAAAAGAAAAAAGAACATCAATAAAAAGAAGTCAGATTTGTTCGAAATC 595
SEQID16    GCTCTTCATGGCCTACTACTACTATTCTGCAA-ACGAGGAATTCAGACC------------ 225
SEQID12    GCTCTTCATGGCCTACTACTACTATTCTGCAA-ACGAGGAATTCAGACC------------ 225
SEQID14    GCTCTTCATGGCCTACTACTACTATTCTGCAA-ACGAGGAATTCAGACC------------ 225
SEQID18    GCTCTTCATGGCCTACTACTACTATTCTGCAA-ACGAGGAATTCAGACC------------ 225
SEQID13    GCTCTTCATGGCCTACTACTACTATTCTGCAA-ACGAGGAATTCAGACC------------ 225
            *     *   *   *  *  *   *** *  * *** *****

SEQID15    ---AGAGATGCTCCAAGGAAAGAAAGTGATTGTCACAGGGGCCAGCAAAGGGATCGGAAG 282
SEQID17    TTGAGAGATGCTCCAAGGAAAGAAAGTGATTGTCACAGGGGCCAGCAAAGGGATCGGAAG 655
SEQID16    ---AGAGATGCTCCAAGGAAAGAAAGTGATTGTCACAGGGGCCAGCAAAGGGATCGGAAG 282
SEQID12    ---AGAGATGCTCCAAGGAAAGAAAGTGATTGTCACAGGGGCCAGCAAAGGGATCGGAAG 282
SEQID14    ---AGAGATGCTCCAAGGAAAGAAAGTGATTGTCACAGGGGCCAGCAAAGGGATCGGAAG 282
SEQID18    ---AGAGATGCTCCAAGGAAAGAAAGTGATTGTCACAGGGGCCAGCAAAGGGATCGGAAG 282
SEQID13    ---AGAGATGCTCCAAGGAAAGAAAGTGATTGTCACAGGGGCCAGCAAAGGGATCGGAAG 282
              ************************************************

SEQID15    AGAGATGGCTTATCATCTGGCGAAGATGGGAGCCCATGTGGTGGTGACAGCGAGGTCAAA 342
SEQID17    AGAGATGGCTTATCATCTGGCGAAGATGGGAGCCCATGTGGTGGTGACAGCGAGGTCAAA 715
SEQID16    AGAGATGGCTTATCATCTGGCGAAGATGGGAGCCCATGTGGTGGTGACAGCGAG------ 336
SEQID12    AGAGATGGCTTATCATCTGGCGAAGATGGGAGCCCATGTGGTGGTGACAGCGAGGTCAAA 342
SEQID14    AGAGATGGCTTATCATCTGGCGAAGATGGGAGCCCATGTGGTGGTGACAGCGAGGTCAAA 342
SEQID18    AGAGATGGCTTATCATCTGGCGAAGATGGGAGCCCATGTGGTGGTGACAGCGAGGTCAAA 342
SEQID13    AGAGATGGCTTATCATCTGGCGAAGATGGGAGCCCATGTGGTGGTGACAGCGAG------ 336
           ******************************************************

SEQID15    AGAAACTCTACAGAAGGTGGTATCCCACTGCCTGGAGCTTGGAGCAGCCTCAGCACACTA 402
SEQID17    AGAAACTCTACAGAAGGTGGTATCCCACTGCCTGGAGCTTGGAGCAGCCTCAGCACACTA 775
SEQID16    ------------------------------------------------CTCAGCACACTA 348
SEQID12    AGAAACTCTACAGAAGGTGGTATCCCACTGCCTGGAGCTTGGAGCAGCCTCAGCACACTA 402
SEQID14    AGAAACTCTACAGAAGGTGGTATCCCACTGCCTGGAGCTTGGAGCAGCCTCAGCACACTA 402
SEQID18    AGAAACTCTACAGAAGGTGGTATCCCACTGCCTGGAGCTTGGAGCAGCCTCAGCACACTA 402
SEQID13    ------------------------------------------------CTCAGCACACTA 348
                                                           ************

SEQID15    CATTGCTGGCACCATGGAAGACATGACCTTCGCAGAGCAATTTGTTGCCCAAGCAGGAAA 462
SEQID17    CATTGCTGGCACCATGGAAGACATGACCTTCGCAGAGCAATTTGTTGCCCAAGCAGGAAA 835
SEQID16    CATTGCTGGCACCATGGAAGACATGACCTTCGCAGAGCAATTTGTTGCCCAAGCAGGAAA 408
SEQID12    CATTGCTGGCACCATGGAAGACATGACCTTCGCAGAGCAATTTGTTGCCCAAGCAGGAAA 462
SEQID14    CATTGCTGGCACCATGGAAGACATGACCTTCGCAGAGCAATTTGTTGCCCAAGCAGGAAA 462
SEQID18    CATTGCTGGCACCATGGAAGACATGACCTTCGCAGAGCAATTTGTTGCCCAAGCAGGAAA 462
SEQID13    CATTGCTGGCACCATGGAAGACATGACCTTCGCAGAGCAATTTGTTGCCCAAGCAGGAAA 408
           ****************************************************

SEQID15    GCTCATGGGAGGACTAGACATGCTCATTCTCAACCACATCACCAACACTTCTTTGAATCT 522
SEQID17    GCTCATGGGAGGACTAGACATGCTCATTCTCAACCACATCACCAACACTTCTTTGAATCT 895
SEQID16    GCTCATGGGAGGACTAGACATGCTCATTCTCAACCACATCACCAACACTTCTTTGAATCT 468
SEQID12    GCTCATGGGAGGACTAGACATGCTCATTCTCAACCACATCACCAACACTTCTTTGAATCT 522
SEQID14    GCTCATGGGAGGACTAGACATGCTCATTCTCAACCACATCACCAACACTTCTTTGAATCT 522
SEQID18    GCTCATGGGAGGACTAGACATGCTCATTCTCAACCACATCACCAACACTTCTTTGAATCT 522
SEQID13    GCTCATGGGAGGACTAGACATGCTCATTCTCAACCACATCACCAACACTTCTTTGAATCT 468
           ***********************************************************

SEQID15    TTTTCATGATGATATTCACCATGTGCGC-------------------------------- 550
SEQID17    TTTTCATGATGATATTCACCATGTGCGCAAAAGCATGGAAGTCAACTTCCTCAGTTACGT 955
SEQID16    TTTTCATGATGATATTCACCATGTGCGCAAAAGCATGGAAGTCAACTTCCTCAGTTACGT 528
```

FIG. 9 (3 of 4)

```
SEQID12   TTTTCATGATGATATTCACCATGTGCGCAAAAGCATGGAAGTCAACTTCCTCAGTTACGT 582
SEQID14   TTTTCATGATGATATTCACCATGTGCGCAAAAGCATGGAAGTCAACTTCCTCAGTTACGT 582
SEQID18   TTTTCATGATGATATTCACCATGTGCGCAAAAGCATGGAAGTCAACTTCCTCAGTTACGT 582
SEQID13   TTTTCATGATGATATTCACCATGTGCGCAAAAGCATGGAAGTCAACTTCCTCAGTTACGT 528
          ************************************************************

SEQID15   ---------------------CCCATGCTGAAGCAGAGCAATGGAAGCATTGTTGTCGT 588
SEQID17   GGTCCTGACTGTAGCTGCCTTGCCCATGCTGAAGCAGAGCAATGGAAGCATTGTTGTCGT 1015
SEQID16   GGTCCTGACTGTAGCTGCCTTGCCCATGCTGAAGCAGAGCAATGGAAGCATTGTTGTCGT 588
SEQID12   GGTCCTGACTGTAGCTGCCTTGCCCATGCTGAAGCAGAGCAATGGAAGCATTGTTGTCGT 642
SEQID14   GGTCCTGACTGTAGCTGCCTTGCCCATGCTGAAGCAGAGCAATGGAAGCATTGTTGTCGT 642
SEQID18   GGTCCTGACTGTAGCTGCCTTGCCCATGCTGAAGCAGAGCAATGGAAGCATTGTTGTCGT 642
SEQID13   GGTCCTGACTGTAGCTGCCTTGCCCATGCTGAAGCAGAGCAATGGAAGCAT------GT 581
                                  *********************************  **

SEQID15   CTCCTCTCTGGCTGGGAAAGTGGCTTATCCAATGGTTGCTGCC-TATTCTGCAAGCAAGT 647
SEQID17   CTCCTCTCTGGCTGGGAAAGTGGCTTATCCAATGGTTGCTGCC-TATTCTGCAAGCAAGT 1074
SEQID16   CTCCTCTCTGGCTGGGAAAGTGGCTTATCCAATGGTTGCTGCC-TATTCTGCAAGCAAGT 647
SEQID12   CTCCTCTCTGGCTGGGAAAGTGGCTTATCCAATGGTTGCTGCC-TATTCTGCAAGCAAGT 701
SEQID14   CTCCTCTCTGGCTGGGAAAGTGGCTTATCCAATGGTTGCTGCC-TATTCTGCAAGCAAGT 701
SEQID18   CTCCTCTCTGGCTG---------------------------------------------- 656
SEQID13   GCGCTCTTCTGCTGGAA------------------TGCTATCATGTTGTGCATCTGAGC 622
          ****    ****

SEQID15   TTGCTTTGGATGGGTTCTTCTCCTCCATCAGAAAGGAATATTCAGTGTCCAGGGTCAATG 707
SEQID17   TTGCTTTGGATGGGTTCTTCTCCTCCATCAGAAAGGAATATTCAGTGTCCAGGGTCAATG 1134
SEQID16   TTGCTTTGGATGGGTTCTTCTCCTCCATCAGAAAGGAATATTCAGTGTCCAGGGTCAATG 707
SEQID12   TTGCTTTGGATGGGTTCTTCTCCTCCATCAGAAAGGAATATTCAGTGTCCAGGGTCAATG 761
SEQID14   TTGCTTTGGATGGGTTCTTCTCCTCCATCAGAAAGGAATATTCAGTGTCCAGGGTCAATG 761
SEQID18   ------------------------------------------------------------
SEQID13   A-GTNGTTGATGG-----TCTCTCTCAT----AGAAGATATCAGG----CAGGCATGATA 668

SEQID15   TATCAATCACTCTCTGTGTTCTTGGCCTCATAGACACAGAAACAGCCATG-AAGGCAGTT 766
SEQID17   TATCAATCACTCTCTGTGTTCTTGGCCTCATAGACACAGAAACAGCCATG-AAGGCAGTT 1193
SEQID16   TATCAATCACTCTCTGTGTTCTTGGCCTCATAGACACAGAAACAGCCATG-AAGGCAGTT 766
SEQID12   TATCAATCACTCTCTGTGTTCTTGGCCTCATAGACACAGAAACAGCCATG-AAGGCAGTT 820
SEQID14   TATCAATCACTCTCTGTGTTCTTGGCCTCATAGACACAGAAACAGCCATG-AAGGCAGTT 820
SEQID18   -----------------------------------AAACAGCCATG-AAGGCAGTT 676
SEQID13   TACT---------------TTGGTCTGCTATACCAGACGCTAGGCGTCTGATGCA--- 708
                                   **  *      *   ***

SEQID15   TCTGGGATAGTCCATATGCAAGCAGCTCCAAAGGAGGAATGTGCCCTGGAGATCATCAAA 826
SEQID17   TCTGGGATAGTCCATATGCAAGCAGCTCCAAAGGAGGAATGTGCCCTGGAGATCATCAAA 1253
SEQID16   TCTGGGATAGTCCATATGCAAGCAGCTCCAAAGGAGGAATGTGCCCTGGAGATCATCAAA 826
SEQID12   TCTGGGATAGTCCATATGCAAGCAGCTCCAAAGGAGGAATGTGCCCTGGAGATCATCAAA 880
SEQID14   TCTGGGATAGTCCATATGCAAGCAGCTCCAAAGGAGGAATGTGCCCTGGAGATCATCAAA 880
SEQID18   TCTGGGATAGTCCATATGCAAGCAGCTCCAAAGGAGGAATGTGCCCTGGAGATCATCAAA 736
SEQID13   ------------------------------------------------------------

SEQID15   GGGGGAGCTCTGCGCCAAGAAGAAGTGTATTATGACAGCTCACTCTGGACCACTCTTCTG 886
SEQID17   GGGGGAGCTCTGCGCCAAGAAGAAGTGTATTATGACAGCTCACTCTGGACCACTCTTCTG 1313
SEQID16   GGGGGAGCTCTGCGCCAAGAAGAAGTGTATTATGACAGCTCACTCTGGACCACTCTTCTG 886
SEQID12   GGGGGAGCTCTGCGCCAAGAAGAAGTGTATTATGACAGCTCACTCTGGACCACTCTTCTG 940
SEQID14   GGGGGAGCTCTGCGCCAAGAAGAAGTGTATTATGACAGCTCACTCTGGACCACTCTTCTG 940
SEQID18   GGGGGAGCTCTGCGCCAAGAAGAAGTGTATTATGACAGCTCACTCTGGACCACTCTTCTG 796
SEQID13   ------------------------------------------------------------

SEQID15   ATCAGAAATCCATGCAGGAAGATCCTGGAATTTCTCTACTCAACGAGCTATAATATGGAC 946
SEQID17   ATCAGAAATCCATGCAGGAAGATCCTGGAATTTCTCTACTCAACGAGCTATAATATGGAC 1373
SEQID16   ATCAGAAATCCATGCAGGAAGATCCTGGAATTTCTCTACTCAACGAGCTATAATATGGAC 946
SEQID12   ATCAGAAATCCATGCAGGAAGATCCTGGAATTTCTCTACTCAACGAGCTATAATATGGAC 1000
SEQID14   ATCAGAAATCCATGCAGGAAGATCCTGGAATTTCTCTACTCAACGAGCTATAATATGGA- 999
SEQID18   ATCAGAAATCCATGCAGGAAGATCCTGGAATTTCTCTACTCAACGAGCTATAATATGGAC 856
SEQID13   ------------------------------------------------------------

SEQID15   AGATTCATAAACAAGTAGGAACTCCCTGAGGGCTGGGCATGCTGAGGGATTTTGGGACTG 1006
SEQID17   AGATTCATAAACAAGTAGGAACTCCCTGAGGGCTGGGCATGCTGAGGGATTTTGGGACTG 1433
```

FIG. 9 (4 of 4)

```
SEQID16   AGATTCATAAACAAGTAGGAACTCCCTGAGGGCTGGGCATGCTGAGGGATTTTGGGACTG 1006
SEQID12   AGATTCATAAACAAGTAGGAACTCCCTGAGGGCTGGGCATGCTGAGGGATTTTGGGACTG 1060
SEQID14   ------------------------------------------------GGGACTG 1006
SEQID18   AGATTCATAAACAAGTAGGAACTCCCTGAGGGCTGGGCATGCTGAGGGATTTTGGGACTG 916
SEQID13   ------------------------------------------------------------

SEQID15   TTCTGTCTCATGTTTATCTGAGCTCTTATCTATGAAGACATCTTCCCAGAGTGTCCCCAG 1066
SEQID17   TTCTGTCTCATGTTTATCTGAGCTCTTATCTATGAAGACATCTTCCCAGAGTGTCCCCAG 1493
SEQID16   TTCTGTCTCATGTTTATCTGAGCTCTTATCTATGAAGACATCTTCCCAGAGTGTCCCCAG 1066
SEQID12   TTCTGTCTCATGTTTATCTGAGCTCTTATCTATGAAGACATCTTCCCAGAGTGTCCCCAG 1120
SEQID14   TTCTGTCTCATGTTTATCTGAGCTCTTATCTATGAAGACATCTTCCCAGAGTGTCCCCAG 1066
SEQID18   TTCTGTCTCATGTTTATCTGAGCTCTTATCTATGAAGACATCTTCCCAGAGTGTCCCCAG 976
SEQID13   ------------------------------------------------------------

SEQID15   AGACATGCAAGTCATGGGTCACACCTGACAAATGGAAGGAGTTCCTCTAACATTTGCAAA 1126
SEQID17   AGACATGCAAGTCATGGGTCACACCTGACAAATGGAAGGAGTTCCTCTAACATTTGCAAA 1553
SEQID16   AGACATGCAAGTCATGGGTCACACCTGACAAATGGAAGGAGTTCCTCTAACATTTGCAAA 1126
SEQID12   AGACATGCAAGTCATGGGTCACACCTGACAAATGGAAGGAGTTCCTCTAACATTTGCAAA 1180
SEQID14   AGACATGCAAGTCATGGGTCACACCTGACAAATGGAAGGAGTTCCTCTAACATTTGCAAA 1126
SEQID18   AGACATGCAAGTCATGGGTCACACCTGACAAATGGAAGGAGTTCCTCTAACATTTGCAAA 1036
SEQID13   ------------------------------------------------------------

SEQID15   ATGGAAATGTAATAATAATGAATGTCATGCACCGCTGCAGCCAGCAGTTGTAAAATTGTT 1186
SEQID17   ATGGAAATGTAATAATAATGAATGTCATGCACCGCTGCAGCCAGCAGTTGTAAAATTGTT 1613
SEQID16   ATGGAAATGTAATAATAATGAATGTCATGCACCGCTGCAGCCAGCAGTTGTAAAATTGTT 1186
SEQID12   ATGGAAATGTAATAATAATGAATGTCATGCACCGCTGCAGCCAGCAGTTGTAAAATTGTT 1240
SEQID14   ATGGAAATGTAATAATAATGAATGTCATGCACCGCTGCAGCCAGCAGTTGTAAAATTGTT 1186
SEQID18   ATGGAAATGTAATAATAATGAATGTCATGCACCGCTGCAGCCAGCAGTTGTAAAATTGTT 1096
SEQID13   ------------------------------------------------------------

SEQID15   AGTAAACATAGGTATAATTACCAGATAGTTATATTAAATTTATATCTTATATATAATAAT 1246
SEQID17   AGTAAACATAGGTATAATTACCAGATAGTTATATTAAATTTATATCTTATATATAATAAT 1673
SEQID16   AGTAAACATAGGTATAATTACCAGATAGTTATATTAAATTTATATCTTATATATAATAAT 1246
SEQID12   AGTAAACATAGGTATAATTACCAGATAGTTATATTAAATTTATATCTTATATATAATAAT 1300
SEQID14   AGTAAACATAGGTATAATTACCAGATAGTTATATTAAATTTATATCTTATATATAATAAT 1246
SEQID18   AGTAAACATAGGTATAATTACCAGATAGTTATATTAAATTTATATCTTATATATAATAAT 1156
SEQID13   ------------------------------------------------------------

SEQID15   ATGTGATGATTAATACAATATTAATTATAATAAAGGTCACATAAACTTTATAAATTCATA 1306
SEQID17   ATGTGATGATTAATACAATATTAATTATAATAAAGGTCACATAAACTTTATAAATTCATA 1733
SEQID16   ATGTGATGATTAATACAATATTAATTATAATAAAGGTCACATAAACTTTATAAATTCATA 1306
SEQID12   ATGTGATGATTAATACAATATTAATTATAATAAAGGTCACATAAACTTTATAAATTCATA 1360
SEQID14   ATGTGATGATTAATACAATATTAATTATAATAAAGGTCACATAAACTTTATAAATTCATA 1306
SEQID18   ATGTGATGATTAATACAATATTAATTATAATAAAGGTCACATAAACTTTATAAATTCATA 1216
SEQID13   ------------------------------------------------------------

SEQID15   ACTGGTAGCTATAACTTGAGCTTATTCAGGATGGTTTCTTTAAAACCATAAACTGTACAA 1366
SEQID17   ACTGGTAGCTATAACTTGAGCTTATTCAGGATGGTTTCTTTAAAACCATAAACTGTACAA 1793
SEQID16   ACTGGTAGCTATAACTTGAGCTTATTCAGGATGGTTTCTTTAAAACCATAAACTGTACAA 1366
SEQID12   ACTGGTAGCTATAACTTGAGCTTATTCAGGATGGTTTCTTTAAAACCATAAACTGTACAA 1420
SEQID14   ACTGGTAGCTATAACTTGAGCTTATTCAGGATGGTTTCTTTAAAACCATAAACTGTACAA 1366
SEQID18   ACTGGTAGCTATAACTTGAGCTTATTCAGGATGGTTTCTTTAAAACCATAAACTGTACAA 1276
SEQID13   ------------------------------------------------------------

SEQID15   ATGAAATTTTTCAATATTTGTTTCTTAT 1394
SEQID17   ATGAAATTTTTCAATATTTGTTTCTTAT 1821
SEQID16   ATGAAATTTTTCAATATTTGTTTCTTAT 1394
SEQID12   ATGAAATTTTTCAATATTTGTTTCTTAT 1448
SEQID14   ATGAAATTTTTCAATATTTGTTTCTTAT 1394
SEQID18   ATGAAATTTTTCAATATTTGTTTCTTAT 1304
SEQID13   -----------------------------
```

Fig 10. (1 of 2)

```
SEQID19   ACTGTTGGCCTCTGGAWTCAGAGGCTGCTGCCTGCCTGGGAGGTTGTAGAAAGCTCTGCA 60
SEQID20   ACTGTTGGCCTCTGGAWTCAGAGGCTGCTGCCTGCCTGGGAGGTTGTAGAAAGCTCTGCA 60
SEQID21   ACTGTTGGCCTCTGGAWTCAGAGGCTGCTGCCTGCCTGGGAGGTTGTAGAAAGCTCTGCA 60
          ************************************************************

SEQID19   GGTTTTCTTCGTGTGTCCTACAGGGCGCCCTGAGCCAGGTCCCTGTTTGATGGCAGTTAT 120
SEQID20   GGTTTTCTTCGTGTGTCCTACAGGGCGCCCTGAGCCAGGTCCCTGTTTGATGGCAGTTAT 120
SEQID21   GGTTTTCTTCGTGTGTCCTACAGGGCGCCCTGAGCCAGGTCCCTGTTTGATGGCAGTTAT 120
          ************************************************************

SEQID19   GAAAAATTACCTCCTCCCGATCCTGGTGCTCTTCCTGGCCTACTACTACTATTCTACAAA 180
SEQID20   GAAAAATTACCTCCTCCCGATCCTGGTGCTCTTCCTGGCCTACTACTACTATTCTACAAA 180
SEQID21   GAAAAATTACCTCCTCCCGATCCTGGTGCTCTTCCTGGCCTACTACTACTATTCTACAAA 180
          ************************************************************

SEQID19   TGAAGAGTTCAGACCAGAAATGCTCCAGGGAAAGAAAGTGATTGTCACTGGGGCCAGCAA 240
SEQID20   TGAAGAGTTCAGAC---------------------------------------------- 194
SEQID21   TGAAGAGTTCAGACCAGAAATGCTCCAGGGAAAGAAAGTGATTGTCACTGGGGCCAGCAA 240
          **************

SEQID19   AGGGATTGGAAGAGAAATGGCATATCATCTGTCAAAAATGGGAGCCCATGTGGTATTGAC 300
SEQID20   ------------------------------------------------------------
SEQID21   AGGGATTGGAAGAGAAATGGCATATCATCTGTCAAAAATGGGAGCCCATGTGGTATTGAC 300

SEQID19   TGCCAGGTCGGAGGAAGGTCTCCAGAAGGTAGTGTCTCGCTGCCTTGAACTCGGAGCAGC 360
SEQID20   ------------------TCCAGAAGGTAGTGTCTCGCTGCCTTGAACTCGGAGCAGC 234
SEQID21   TGCCAGGTCGGAGGAAGGTCTCCAGAAGGTAGTGTCTCGCTGCCTTGAACTCGGAGCAGC 360
                            ******************************************

SEQID19   CTCTGCTCACTACATTGCTGGCACTATGGAAGACATGACATTTGCGGAGCAATTTATTGT 420
SEQID20   CTCTGCTCACTACATTGCTGGCACTATGGAAGACATGACATTTGCGGAGCAATTTATTGT 294
SEQID21   CTCTGCTCACTACATTGCTGGCACTATGGAAGACATGACATTTGCGGAGCAATTTATTGT 420
          ************************************************************

SEQID19   CAAGGCGGGAAAGCTCATGGGCGGACTGGACATGCTTATTCTAAACCACATCACTCAGAC 480
SEQID20   CAAGGCGGGAAAGCTCATGGGCGGACTGGACATGCTTATTCTAAACCACATCACTCAGAC 354
SEQID21   CAAGGCGGGAAAGCTCATGGGCGGACTGGACATGCTTATTCTAAACCACATCACTCAGAC 480
          ************************************************************

SEQID19   CTCGCTGTCTCTCTTCCATGACGACATCCACTCTGTGCGAAGAGTCATGGAGGTCAACTT 540
SEQID20   CTCGCTGTCTCTCTTCCATGACGACATCCACTCTGTGCGAAGAGTCATGGAGGTCAACTT 414
SEQID21   CTCGCTGTCTCTCTTCCATGACGACATCCACTCTGTGCGAAGAGTCATGGAGGTCAACTT 540
          ************************************************************

SEQID19   CCTCAGCTACGTGGTCATGAGCACAGCCGCCTTGCCCATGCTGAAGCAGAGCAATGGCAG 600
SEQID20   CCTCAGCTACGTGGTCATGAGCACAGCCGCCTTGCCCATGCTGAAGCAGAGCAATGGCAG 474
SEQID21   CCTCAGCTACGTGGTCATGAGCACAGCCGCCTTGCCCATGCTGAAGCAGAGCAATGGCAG 600
          ************************************************************

SEQID19   CATTGCCGTCATCTCCTCCTTGGCTGGGAAAATGACCCAGCCTATGATTGCTCCCTACTC 660
SEQID20   CATTGCCGTCATCTCCTCCTTGGCTGGGAAAATGACCCAGCCTATGATTGCTCCCTACTC 534
SEQID21   CATTGCCGTCATCTCCTCCTTGGCTGGGGAA-GAACAGTTCCACAACAGAGA---AGTC 656
          ****************************  **  *    *  *  *      *  **

SEQID19   TGCAAGCAAGTTTGCTCTGGATGGGTTCTTTTCCACCATTAGAACAGAACTCTACATAAC 720
SEQID20   TGCAAGCAAGTTTGCTCTGGATGGGTTCTTTTCCACCATTAGAACAGAACTCTACATAAC 594
SEQID21   -----GCAGTGTTACTCCTGAC---------TCCCGC-----GGCCCGTGATTAATATCAC 698
               ***  **  ***  **         *  ***       *  *    *  *   **

SEQID19   CAAGGTCAACGTGTCCATCACTCTCTGTGTCCTTGGCCTCATAGACACACAGAAACAGCTAT 780
SEQID20   CAAGGTCAACGTGTCCATCACTCTCTGTGTCCTTGGCCTCATAGACACACAGAAACAGCTAT 654
SEQID21   CAGCCACAGAATGGAC-TGGAACCCTGTATC---GATCTGGTGGGATTGGATATAACGAA 754
          **  **   **  *  *    *  *  *** **   *  *      **  **  *  *

SEQID19   GAAGGAA--ATCTCTGGGATAATTAACGCCCAAGCTTCTCCCAAGGAGGAGTGCGCCCTG 838
SEQID20   GAAGGAA--ATCTCTGGGATAATTAACGCCCAAGCTTCTCCCAAGGAGGAGTGCGCCCTG 712
SEQID21   CATAGAATTACTCCTGAGACTACCAGAACTGAA---TAGTTCAAATCAAATCATGCC--- 808
```

FIG. 10 (2 of 2)

```
                    *  ***  *  *** **  *  *    *  **   *    ***    *     ***
SEQID19    GAGATCATCAAAGGCACAGCTCTACGCAAAAGCGAGGTGTACTATGACAAATCGCCTTTG 898
SEQID20    GAGATCATCAAAGGCACAGCTCTACGCAAAAGCGAGGTGTACTATGACAAATCGCCTTTG 772
SEQID21    -AGAATATC--AGACAAATCCAAATGGCAAAAC-AGTTGCA------------------- 845
                    ***   ***  **  **  *  *    *  *  ***  *  **  **  *

SEQID19    ACTCCAATCCTGCTTGGGAACCCAGGAAGGAAGATCATGGAATTTTTTTCATTACGATAT 958
SEQID20    ACTCCAATCCTGCTTGGGAACCCAGGAAGGAAGATCATGGAATTTTTTTCATTACGATAT 832
SEQID21    ------------------------------------------------------------

SEQID19    TATAATAAGGACATGTTTGTAAGTAACTAGGAACTCCTGAGCCCTGGTGAGTGGTCTTAG 1018
SEQID20    TATAATAAGGACATGTTTGTAAGTAACTAGGAACTCCTGAGCCCTGGTGAGTGGTCTTAG 892
SEQID21    ------------------------------------------------------------

SEQID19    AACAGTCCTGCCTGATACTTCTGTAAGCCCTACCCACAAAAGTATCTTTCCAGAGATACA 1078
SEQID16    AACAGTCCTGCCTGATACTTCTGTAAGCCCTACCCACAAAAGTATCTTTCCAGAGATACA 952
SEQID21    ------------------------------------------------------------

SEQID19    CAAATTTTGGGGTACACCTCATCATGAGAAATTCTTGCAACACTTGCACAGTGAAAATGT 1138
SEQID20    CAAATTTTGGGGTACACCTCATCATGAGAAATTCTTGCAACACTTGCACAGTGAAAATGT 1012
SEQID21    ------------------------------------------------------------

SEQID19    AATTGTAATAAATGTCACAAACCACTTTGGGGCCTGCAGTTGTGAACTTGATTGTAACTA 1198
SEQID20    AATTGTAATAAATGTCACAAACCACTTTGGGGCCTGCAGTTGTGAACTTGATTGTAACTA 1072
SEQID21    ------------------------------------------------------------

SEQID19    TGGATATAAACACATAGTGGTTGTATCGGCTTTACCTCACACTGAATGAAACAATGATAA 1258
SEQID20    TGGATATAAACACATAGTGGTTGTATCGGCTTTACCTCACACTGAATGAAACAATGATAA 1132
SEQID21    ------------------------------------------------------------

SEQID19    CTAATGTAACATTAAATATAATAAAGGTAATATCAACTTTGTAAATGCA 1307
SEQID20    CTAATGTAACATTAAATATAATAAAGGTAATATCAACTTTGTAAATGCA 1181
SEQID21    -------------------------------------------------
```

GHRELIN VARIANT PROTEIN

FIELD OF THE INVENTION

The present invention relates to obesity and diabetes markers, to reagents which can detect obesity and diabetes marker transcripts and translation products, to kits and methods for detecting obesity and diabetes marker transcripts and translation products, to methods and kits for screening and diagnosing obesity and diabetes in individuals and monitoring response to treatment, disease progression and disease recurrence in patients diagnosed with obesity and diabetes, to compounds which specifically bind to translation products of obesity and/or diabetes marker transcripts, to compositions for and methods of treating obesity and/or diabetes.

BACKGROUND OF THE INVENTION

Obesity is the second most important cause of preventable death in the United States, exceeded only by cigarette smoking. Obesity is estimated to affect 58,000,000 people and contribute to 300,000 deaths annually in the United States and its prevalence is increasing. Individuals suffering from the disease are at increased risk of illness from hypertension, lipid disorders, coronary heart disease, type II diabetes, stroke, gall bladder disease, osteoarthritis, sleep apnea, respiratory problems and certain cancers.

Obesity develops when there is an excess of energy intake over energy usage. The causes of this excess may vary from patient to patient and are believed to stem from various genetic, social and environmental factors. Current research supports the view that under identical environmental conditions, different people gain weight at different rates and the amount they gain seems to be genetically determined. It has been proposed that natural selection caused our distant ancestors to acquire 'thrifty genes' which boosted the ability to store fat from each feast in order to sustain the body through the next famine. In today's environment of a surfeit of high fat, high calorie 'western style' food, 'thrifty genes' have become a liability.

More and more scientists and physicians are coming to reject the traditional belief that poor diet and lack of exercise are solely to blame for obesity and are increasingly tending to view it as a medical condition. Health economists, using prospective studies and national health statistics, have calculated the costs of obesity in the US in 1995 at $99.2 billion. By 2005 it is estimated that more than 120 million will be obese. The number of people living in France, Germany, Italy, the UK and the US could rise from 71 million in 1999 to 78 million in 2005. The economic impact of obesity in the US is now comparable to that of diabetes and ranks alongside expenditure on heart disease and hypertension. Medical researchers calculate that at least 88% of all cases of type II diabetes, 57% of coronary heart disease cases, 11% of breast cancers, and 10% of colon cancers diagnosed in overweight Americans are attributable to obesity.

The World health Organization has classified the obesity condition as an epidemic, and has set up a special task force to tackle one of the greatest risks to human health and well-being.

There remains a need for obesity and/or diabetes specific markers. There remains a need for reagents and kits which can be used to detect the presence of obesity and/or diabetes markers in samples from patients. There remains a need for methods of screening and diagnosing individuals who have obesity and/or diabetes and methods of monitoring response to treatment, disease progression and disease recurrence in patients diagnosed with obesity and diabetes. There remains a need for reagents, kits and methods for determining the type of obesity and/or diabetes that an individual who is obese has. There remains a need for compositions which can specifically target obesity and/or diabetes related cells. There remains a need for imaging agents which can specifically bind to obesity and/or diabetes cells. There remains a need for improved methods of imaging obesity and/or diabetes cells. There remains a need for therapeutic agents which can specifically bind to obesity and/or diabetes cells. there remains a need for improved methods of treating individuals who are suspected of suffering from obesity and diabetes.

GLOSSARY

In the following description and claims use will be made, at times, with a variety of terms, and the meaning of such terms as they should be construed in accordance with the invention is as follows:

"Obesity and/or diabetes nucleic acid sequences"—the sequence shown in any one of SEQ ID NO: 1 to SEQ ID NO: 4 and of SEQ ID NO: 22 to SEQ ID NO: 25 sequences having at least 90% identity (see below) to said sequences and fragments (see below) of the above sequences of least 20 b.p. long. These sequences are sequences coding for naturally occurring, alternative splice variants of the native and known Adiponectin, depicted in Locus Link as locus Hs. 9370 under Accession Number NM_004797 which is the sequence coding for the human 30 kDa glycoprotein of 244 amino acids. It should be emphasized that the novel variants of the present invention are naturally occurring sequences resulting from alternative splicing of Adiponectin and not merely truncated, mutated or fragmented form of the gene.

the sequence shown in any one of SEQ ID NO: 5 to SEQ ID NO: 9 and of SEQ ID NO: 26 to SEQ ID NO: 30 sequences having at least 90% identity (see below) to said sequences and fragments (see below) of the above sequences of least 20 b.p. long. These sequences are sequences coding for naturally occurring, alternative splice variants of the native and known Adiponectin, depicted in Locus Link as locus Mm. 11450 under Accession Number NM_009605 which is the sequence coding for the mouse 30 kDa glycoprotein of 247 amino acids. It should be emphasized that the novel variants of the present invention are naturally occurring sequences resulting from alternative splicing of Adiponectin and not merely truncated, mutated or fragmented form of the gene.

the sequence shown in any one of SEQ ID NO: 10 to SEQ ID NO: 11 and of SEQ ID NO: 31 to SEQ ID NO: 32 sequences having at least 90% identity (see below) to said sequences and fragments (see below) of the above sequences of least 20 b.p. long. These sequences are sequences coding for naturally occurring, alternative splice variants of the native and known Ghrelin, depicted in Locus Link as locus Hs. 51738 under Accession Number NM_016362 which is the sequence coding for the human 13 kDa glycoprotein of 117 amino acids. It should be emphasized that the novel variants of the present invention are naturally occurring sequences resulting from alternative splicing of Ghrelin and not merely truncated, mutated or fragmented form of the gene.

the sequence shown in any one of SEQ ID NO: 12 to SEQ ID NO: 18 and of SEQ ID NO: 33 to SEQ ID NO: 39 sequences having at least 90% identity (see below) to said sequences and fragments (see below) of the above sequences of least 20 b.p. long. These sequences are sequences coding for naturally occurring, alternative splice variants of the native and known 11-beta-HSD, depicted in Locus Link as locus Hs. 3290 under Accession Number NM_005525 which is the sequence coding for the human 32 kDa glycoprotein of 292 amino acids. It should be emphasized that the novel variants of the present invention are naturally occurring sequences resulting from alternative splicing of 11-beta-HSD and not merely truncated, mutated or fragmented form of the gene.

the sequence shown in any one of SEQ ID NO: 19 to SEQ ID NO: 21 and of SEQ ID NO: 40 to SEQ ID NO: 42 sequences having at least 90% identity (see below) to said sequences and fragments (see below) of the above sequences of least 20 b.p. long. These sequences are sequences coding for naturally occurring, alternative splice variants of the native and known 11-beta-HSD, depicted in Locus Link as locus Mm. 15483 under Accession Number NM_008288 which is the sequence coding for the mouse 32 kDa glycoprotein of 292 amino acids. It should be emphasized that the novel variants of the present invention are naturally occurring sequences resulting from alternative splicing of 11-beta-HSD and not merely truncated, mutated or fragmented form of the gene.

The description of the obesity and/or diabetes variants and their difference from the original sequence is summarized in Table 1 as follows:

TABLE 1

| SEQ ID NO: | Obesity and Diabetes related genes | GenBank Human Locus ID | GenBank Mouse Locus ID | Gene Symbol | Variation description |
|---|---|---|---|---|---|
| 1 | Adiponectin-WT (Variant 1) | 9370 | 11450 | APM | Nucleotide sequence of the human wild type protein (human) |
| 2 | Adiponectin Variant 2 | | | | Nucleotide sequence of variant 2 (human) |
| 3 | Adiponectin Variant 3 | | | | Nucleotide sequence of variant 3 (human) |
| 4 | Adiponectin Variant 4 | | | | Nucleotide sequence of variant 4 (human) |
| 5 | Adiponectin-WT (Variant 1) | 9370 | 11450 | APM | Nucleotide sequence of the mouse wild type protein (mouse) |
| 6 | Adiponectin Variant 2 | | | | Nucleotide sequence of variant 2 (mouse) |
| 7 | Adiponectin Variant 3 | | | | Nucleotide sequence of variant 3 (mouse) |
| 8 | Adiponectin Variant 4 | | | | Nucleotide sequence of variant 4 (mouse) |
| 9 | Adiponectin Variant 5 | | | | Nucleotide sequence of variant 5 (mouse) |
| 10 | Ghrelin- WT (variant 1) | 51738 | 58991 | GHRL | Nucleotide sequence of the human wild type protein |
| 11 | Ghrelin Variant 2 | | | | Nucleotide sequence of variant 2 (human) |
| 12 | 11-beta-HSD - WT (Variant 1) | 3290 | 15483 | HSD11B1 | Nucleotide sequence of the wild type human protein |
| 13 | 11-beta-HSD Variant 2 | | | | Nucleotide sequence of variant 2 (human) |
| 14 | 11-beta-HSD Variant 3 | | | | Nucleotide sequence of variant 3 (human) |
| 15 | 11-beta-HSD Variant 4 | | | | Nucleotide sequence of variant 4 (human) |
| 16 | 11-beta-HSD Variant 5 | | | | Nucleotide sequence of variant 5 (human) |
| 17 | 11-beta-HSD Variant 6 | | | | Nucleotide sequence of variant 6 (human) |
| 18 | 11-beta-HSD Variant 7 | | | | Nucleotide sequence of variant 7 (human) |
| 19 | 11-beta-HSD - WT (Variant 1) | | | | Nucleotide sequence of the mouse wild type protein |
| 20 | 11-beta-HSD Variant 8 | | | | Nucleotide sequence of variant 8 (mouse) |
| 21 | 11-beta-HSD Variant 9 | | | | Nucleotide sequence of variant 9 (mouse) |
| 22 | Adiponectin-WT (Variant 1) | 9370 | 11450 | APM | Wild type human protein sequence |
| 23 | Adiponectin Variant 2 | | | | Alternative initiation (human) |
| 24 | Adiponectin Variant 3 | | | | |
| 25 | Adiponectin Variant 4 | | | | |

TABLE 1-continued

| SEQ ID NO: | Obesity and Diabetes related genes | GenBank Human Locus ID | GenBank Mouse Locus ID | Gene Symbol | Variation description |
|---|---|---|---|---|---|
| 26 | Adiponectin-WT (Variant 1) | 9370 | 11450 | APM | Wild type mouse protein sequence |
| 27 | Adiponectin Variant 2 | | | | Alternative initiation (mouse) |
| 28 | Adiponectin Variant 3 | | | | Alternative 45 amino acids from position 111 in the wild type protein creating a variant with 156 amino acids (mouse) |
| 29 | Adiponectin Variant 4 | | | | Alternative 58 amino acids from position 111 in the wild type protein creating a variant with 169 amino acids (mouse) |
| 30 | Adiponectin Variant 5 | | | | Truncated variant 76 amino acids long (mouse) |
| 31 | Ghrelin- WT (variant 1) | 51738 | 58991 | GHRL | Wild type human protein sequence |
| 32 | Ghrelin Variant 2 | | | | Alternative 70 amino acids from position 35 in the wild type protein creating a variant with 117 amino acids (human) |
| 33 | 11-beta-HSD - WT (Variant 1) | 3290 | 15483 | HSD11B1 | Wild type human protein sequence |
| 34 | 11-beta-HSD Variant 2 | | | | Deletion of 18 amino acids from amino acid 64 in the wild type protein and an alternative exon of 16 amino acids replacing the rest of the amino acids from amino acid 165 in the wild type protein (human) |
| 35 | 11-beta-HSD Variant 3 | | | | Alternative 9 amino acids from amino acid 286 creating a variant with 295 amino acids (human) |
| 36 | 11-beta-HSD Variant 4 | | | | Deletion of 18 amino acids from amino acid 137 till amino acid 155 in the wild type protein (human) |
| 37 | 11-beta-HSD Variant 5 | | | | Deletion of 20 amino acids from amino acid 64 till amino acid 84 in the wild type protein (human) |
| 38 | 11-beta-HSD Variant 6 | | | | Alternative initiation at amino acid no. 31 in the wild type protein (human) |
| 39 | 11-beta-HSD Variant 7 | | | | Deletion of 48 amino acids from amino acid 173 till amino acid 221 in the wild type protein (human) |
| 40 | 11-beta-HSD - WT (Variant 1) | | | | Wild type mouse protein sequence |
| 41 | 11-beta-HSD Variant 8 | | | | Deletion of 32 amino acids from amino acid 29 till amino acid 71 in the wild type protein |
| 42 | 11-beta-HSD Variant 9 | | | | Alternative 19 amino acids from amino acid 173 creating a variant with 192 amino acids (mouse) |

SEQ ID NOS: 1–21 are nucleotide sequences.
SEQ ID NOS: 22–42 are protein sequences encoded by SEQ ID NOS 1–21.

TABLE 2

SEQ ID 1–9 Adiponectin variants:
SEQ ID NO. 1: NM_004797_T1 | Length 4517
CTGATTCCATACCAGAGGGGCTCAGGATGCTGTTGCTGGGAGCTGTTCTACTGCTATTAG

CTCTGCCCGGGCATGACCAGGAAACCACGACTCAAGGGCCCGGAGTCCTGCTTCCCCTGC

CCAAGGGGGCCTGCACAGGTTGGATGGCGGGCATCCCAGGGCATCCGGGCCATAATGGGG

CCCCAGGCCGTGATGGCAGAGATGGCACCCCTGGTGAGAAGGGTGAGAAAGGAGATCCAG

GTCTTATTGGTCCTAAGGGAGACATCGGTGAAACCGGAGTACCCGGGGCTGAAGGTCCCC

GAGGCTTTCCGGGAATCCAAGGCAGGAAAGGAGAACCTGGAGAAGGTGCCTATGTATACC

GCTCAGCATTCAGTGTGGGATTGGAGACTTACGTTACTATCCCCAACATGCCCATTCGCT

TTACCAAGATCTTCTACAATCAGCAAAACCACTATGATGGCTCCACTGGTAAATTCCACT

GCAACATTCCTGGGCTGTACTACTTTGCCTACCACATCACAGTCTATATGAAGGATGTGA

AGGTCAGCCTCTTCAAGAAGGACAAGGCTATGCTCTTCACCTATGATCAGTACCAGGAAA

ATAATGTGGACCAGGCCTCCGGCTCTGTGCTCCTGCATCTGGAGGTGGGCGACCAAGTCT

GGCTCCAGGTGTATGGGGAAGGAGAGCGTAATGGACTCTATGCTGATAATGACAATGACT

CCACCTTCACAGGCTTTCTTCTCTACCATGACACCAACTGATCACCACTAACTCAGAGCC

TCCTCCAGGCCAAACAGCCCCAAAGTCAATTAAAGGCTTTCAGTACGGTTAGGAAGTTGA

TTATTATTTAGTTGGAGGCCTTTAGATATTATTCATTCATTTACTCATTCATTTATTCAT

TCATTCATCAAGTAACTTTAAAAAAATCATATGCTATGTTCCCAGTCCTGGGGAGCTTCA

CAAACATGACCAGATAACTGACTAGAAAGAAGTAGTTGACAGTGCTATTTTGTGCCCACT

GTCTCTCCTGATGCTCATATCAATCCTATAAGGCACAGGGAACAAGCATTCTCCTGTTTT

TACAGATTGTATCCTGAGGCTGAGAGAGTTAAGTGAATGTCTAAGGTCACACAGTATTAA

GTGACAGTGCTAGAAATCAAACCCAGAGCTGTGGACTTTGTTCACTAGACTGTGCCCTTT

TATAGAGGTACATGTTCTCTTTGGAGTGTTGGTAGGTGTCTGTTTCCCACCTCACCTGAG

AGCCATTGAATTTGCCTTCCTCATGAATTAAAACCTCCCCCAAGCAGAGCTTCCTCAGAG

AAAGTGGTTCTATGATGAAGTCCTGTCTTGGAAGGACTACTACTCAATGGCCCCTGCACT

ACTCTACTTCCTCTTACCTATGTCCCTTCTCATGCCTTTCCCTCCAACGGGGAAAGCCAA

CTCCATCTCTAAGTGCTGAACTCATCCCTGTTCCTCAAGGCCACCTGGCCAGGAGCTTCT

CTGATGTGATATCCACTTTTTTTTTTTTTGAGATGGAGTCTCACTCTGTCACCCAGGCT

GGAGTACAGTGACACGACCTCGGCTCACTGCAGCCTCCTTCTCCTGGGTCCAAGCAATTA

TTGTGCCTCAGCCTCCCGAGTAGCTGAGACTTCAGGTGCATTCCACCACACATGGCTAAT

TTTTGTATTTTTAGTAGAAATGGGGTTTCGTCATGTTGGCCAGGCTGGTCTCGAACTCCT

GGCCTAGGTGATCCACCCGCCTCGACCTCCCAAAGTGCTGGGATTACAGGCATGAGCCAC

CATGCCCAGTCGATATCTCACTTTTTATTTTGCCATGGATGAGAGTCCTGGGTGTGAGGA

ACACCTCCCACCAGGCTAGAGGCAACTGCCCACGAAGGACTGTGCTTCCGTCACCTCTAA

ATCCCTTGCAGATCCTTGATAAATGCCTCATGAAGACCAATCTCTTGAATCCCATATCTA

CCCAGAATTAACTCCATTCCAGTCTCTGCATGTAATCAGTTTTATCCACAGAAACATTTT

CATTTTAGGAAATCCCTGGTTTAAGTATCAATCCTTGTTCAGCTGGACAATATGAATCTT

TTCCACTGAAGTTAGGGATGACTGTGATTTTCAGAACACGTCCAGAATTTTTCATCAAGA

AGGTAGCTTGAGCCTGAAATGCAAAACCCATGGAGGAATTCTGAAGCCATTGTCTCCTTG

AGTACGAACAGGGTCAGGGAAGACTGGGCCTCCTGAATTTATTATTGTTCTTTAAGAATT

ACAGGTTGAGGTAGTTGATGGTGGTAAACATTCTCTCAGGAGACAATAACTCCAGTGATG

TABLE 2-continued

```
TTTTTCAAAGATTTTAGCAAAAACAGAGTAAATAGCATTCTCTATCAATATATAAATTTA
AAAAACTATCTTTTTGCTTACAGTTTTAAATTCTGAACAATTTCTCTTATATGTGTATTG
CTAATCATTAAGGTATTATTTTTTCCACATATAAAGCTTTGTCTTTTTGTTGTTGTTGTT
GTTTTTAAGATGGAGTTTCCCTCTGTTCCCAGGCTAGAGTGCAGTGGCATGATCTCGGCT
TACTGCAACCTTTGCCTCCCACGTTTAAGCGATTCTTCTGCCTCAGCCTCCCGAGTAGCT
GGGACCACACGTGCCTACCACCATGCCAGGCTAATTTTTGTATTTTTAGTAAAGACAGGG
TTTCACCATATTGGCCAGGCTGGTCTCGAACTCCTGACCTTGTGATCTGCCCGCCTCCAT
TGTGTTGTTATTTGTGAGAAAGATAGATATGAGGTTTAGAGAGGGATGAAGAGGTGAGAG
TAAGCCTTGTGTTAGTCAGAACTCTGTGTTGTGAATGTCATTCACAACAGAAAACCCAAA
ATATTATGCAAACTACTGTAAGCAAGAAAAATAAAGGAAAAATGGAAACATTTATTCCTT
TGCATAATAGAAATTACCAGAGTTGTTCTGTCTTTAGATAAGGTTTGAACCAAAGCTCAA
AACAATCAAGACCCTTTTCTGTATGTCCTTCTGTTCTGCCTTCCGCAGTGTAGGCTTTAC
CCTCAGGTGCTACACAGTATAGTTCTAGGGTTTCCCTCCCGATATCAAAAAGACTGTGGC
CTGCCCAGCTCTCGTATCCCCAAGCCACACCATCTGGCTAAATGGACATCATGTTTTCTG
GTGATGCCCAAAGAGGAGAGAGGAAGCTCTCTTTCCCAGATGCCCCAGCAAGTGTAACCT
TGCATCTCATTGCTCTGGCTGAGTTGTGTGCCTGTTTCTGACCAATCACTGAGTCAGGAG
GATGAAATATTCATATTGACTTAATTGCAGCTTAAGTTAGGGGTATGTAGAGGTATTTTC
CCTAAAGCAAAATTGGGACACTGTTATCAGAAATAGGAGAGTGGATGATAGATGCAAAAT
AATACCTGTCCACAACAAACTCTTAATGCTGTGTTTGAGCTTTCATGAGTTTCCCAGAGA
GACATAGCTGGAAAATTCCTATTGATTTTCTCTAAAATTTCAACAAGTAGCTAAAGTCTG
GCTATGCTCACAGTCTCACATCTGGTGGGGGTGGGCTCCTTACAGAACACGCTTTCACAG
TTACCCTAAACTCTCTGGGGCAGGGTTATTCCTTTGTGGAACCAGAGGCACAGAGACAGT
CAACTGAGGCCCAACAGAGGCCTGAGAGAAACTGAGGTCAAGATTTCAGGATTAATGGTC
CTGTGATGCTTTGAAGTACAATTGTGGATTTGTCCAATTCTCTTTAGTTCTGTCAGCTTT
TGCTTCATATATTTTAGCGCTCTATTATTAGATATATACATGTTTAGTATTATGTCTTAT
TGGTGCATTTACTCTCTTATCATTATGTAATGTCCTTCTTTATCTGTGATAATTTTCTGT
GTTCTGAAGTCTACTTTGTCTAAAAATAACATACGCACTCAACTTCCTTTTCTTTCTTCC
TTCCTTTCTTTCTTCCTTCCTTTCTTTCTCTCTCTCTTTCCTTCCTTCCTTCCTCCTT
TTCTCTCTCTCTCTCTCTCTCTCTTTTCTTGACAGACTCTCGTTCTGTGGCCCTGGCT
GGAGTTCAGTGGTGTGATCTTGGCTCACTGCTACCTCTACCATGAGCAATTCTCCTGCCT
CAGCCTCCCAAGTAGCTGGAACTACAGGCTCATGCCACTGCGCCCAGCTAATTTTTGTAT
TTTTCGTAGAGACGGGGTTTCACCACATTCGTCAGGTTGGTTTCAAACTCCTGACTTTGT
GATCCACCCGCCTCGGCCTCCCAAAGTGCTGGGATTACAGGCATGAGCCATCACACCTGG
TCAACTTTCTTTTGATTAGTGTTTTTGTGGTATATCTTTTTCCATCATGTTACTTTAAAT
ATATCTATATTATTGTATTTAAAATGTGTTTCTTACAGAGTGCATGTAGTTGGGTATAAT
TTTTATCCAGTCTAAAAATATCTGTCTTTTAATTGGTGTTTAGACAATTTATATTTAATA
AAATGGTGGAATTTAAA
```
SEQ ID NO. 2: NM_004797_T2 | Length 484
```
ATGACCCGGGGCTGAAGGTCCCCGAGGCTTTCCGGGAATCCAAGGCAGGAAAGGAGAACC
TGGAGAAGGTGCCTATGTATACCGCTCAGCATTCAGTGTGGGATTGGAGACTTACGTTAC
```

TABLE 2-continued

TATCCCCAACATGCCCATTCGCTTTACCAAGATCTTCTACAATCAGCAAAACCACTATGA

TGGCTCCACTGGTAAATTCCACTGCAACATTCCTGGGCTGTACTACTTTGCCTACCACAT

CACAGTCTATATGAAGGATGTGAAGGTCAGCCTCTTCAAGAAGGACAAGGCTATGCTCTT

CACCTATGATCAGTACCAGGAAAATAATGTGGACCAGGCCTCCGGCTCTGTGCTCCTGCA

TCTGGAGGTGGGCGACCAAGTCTGGCTCCAGGTGTATGGGGAAGGAGAGCGTAATGGACT

CTATGCTGATAATGACAATGACTCCACCTTCACAGGCTTTCTTCTCTACCATGACACCAA

CTGA

SEQ ID NO. 3: NM_004797_T3 | Length 718
CTGATTCCATACCAGAGGGGCTCAGGATGCTGTTGCTGGGAGCTGTTCTACTGCTATTAG

CTCTGCCCGGGCATGACCAGGAAACCACGACTCAAGGGCCCGGAGTCCTGCTTCCCCTGC

CCAAGGGGGCCTGCACAGGTTGGATGGCGGGCATCCCAGGGCATCCGGGCCATAATGGGG

CCCCAGGCCGTGATGGCAGAGATGGCACCCCTGGTGAGAAGGGTGAGAAAGGAGATCCAG

GTCTTATTGGTCCTAAGGGAGACATCGGTGAAACCGGAGTACCCGGGGCTGAAGGTCCCC

GAGGCTTTCCGGGAATCCAAGGCAGGAAAGGAGAACCTGGAGAAGGTGCGTTACTATCCC

CAACATGCCCATTCGCTTTACCAAGATCTTCTACAATCAGCAAAACCACTATGATGGCTC

CACTGGTAAATTCCACTGCAACATTCCTGGGCTGTACTACTTTGCCTACCACATCACAGT

CTATATGAAGGATGTGAAGGTCAGCCTCTTCAAGAAGGACAAGGCTATGCTCTTCACCTA

TGATCAGTACCAGGAAAATAATGTGGACCAGGCCTCCGGCTCTGTGCTCCTGCATCTGGA

GGTGGGCGACCAAGTCTGGCTCCAGGTGTATGGGGAAGGAGAGCGTAATGGACTCTATGC

TGATAATGACAATGACTCCACCTTCACAGGCTTTCTTCTCTACCATGACACCAACTGA

SEQ ID NO. 4: NM_004797_T4 | Length 537
CTGATTCCATACCAGGGGGCTCAGGATGCTGTTGCTGGGAGCTGTTCTACTGCTATTAG

CTCTGCCCGGGCATGACCAGGAAACCACGACTCAAGGGCCCGGAGTCCTGCTTCCCCTGC

CCAAGGGGGCCTGCACAGGTTGGATGGCGGGCATCCCAGGGCATCCGGGCCATAATGGGG

CCCCAGGCCGTGATGGCAGAGATGGCACCCCTGGTGAGAAGGGTGAGAAAGGAGATCCAG

GTCTTATTGGTCCTAAGGGAGACATCGGTGAAACCGGAGTACCCGGGGCTGAAGGTCCCC

GAGGCTTTCCGGGAATCCAAGGCAGGAAAGGAGAACCTGGAGAAGGTGCCTATGTATACC

GCTCAGCATTCAGTGTGGGATTGGAGACTTACGTTACTATCCCCAACATGCCCATTCGCT

TTACCAAGATCTTCTACAATCAGCAAAACCACTATGATGGCTCCACTGGTAAATTCCACT

GCAACATTCCTGGGCTGTACCTTCACAGGCTTTCTTCTCTACCATGACACCAACTGA

SEQ ID NO. 5: U37222_T1 | Length: 1306 WT
ATGAGACCTGGCCACTTTCTCCTCATTTCTGTCTGTACGATTGTCAGTGGATCTGACGAC

ACCAAAAGGGCTCAGGATGCTACTGTTGCAAGCTCTCCTGTTCCTCTTAATCCTGCCCAG

TCATGCCGAAGATGACGTTACTACAACTGAAGAGCTAGCTCCTGCTTTGGTCCCTCCACC

CAAGGGAACTTGTGCAGGTTGGATGGCAGGCATCCCAGGACATCCTGGCCACAATGGCAC

ACCAGGCCGTGATGGCAGAGATGGCACTCCTGGAGAGAAGGGAGAGAAGGAGATGCAGG

TCTTCTTGGTCCTAAGGGTGAGACAGGAGATGTTGGAATGACAGGAGCTGAAGGGCCACG

GGGCTTCCCCGGAACCCCTGGCAGGAAAGGAGAGCCTGGAGAAGCCGCTTATGTGTATCG

CTCAGCGTTCAGTGTGGGGCTGGAGACCCGCGTCACTGTTCCCAATGTACCCATTCGCTT

TACTAAGATCTTCTACAACCAACAGAATCATTATGACGGCAGCACTGGCAAGTTCTACTG

CAACATTCCGGGACTCTACTACTTCTCTTACCACATCACGGTGTACATGAAAGATGTGAA

TABLE 2-continued

GGTGAGCCTCTTCAAGAAGGACAAGGCCGTTCTCTTCACCTACGACCAGTATCAGGAAAA

GAATGTGGACCAGGCCTCTGGCTCTGTGCTCCTCCATCTGGAGGTGGGAGACCAAGTCTG

GCTCCAGGTGTATGGGGATGGGGACCACAATGGACTCTATGCAGATAACGTCAACGACTC

TACATTTACTGGCTTTCTTCTCTACCATGATACCAACTGACTGCAACTACCCATAGCCCA

TACACCAGGAGAATCATGGAACAGTCGACACACTTTCAGCTTAGTTTGAGAGATTGATTT

TATTGCTTAGTTTGAGAGTCCTGAGTATTATCCACACGTGTACTCACTTGTTCATTAAAC

GACTTTATAAAAAATAATTTGTGTTCCTAGTCCAGAAAAAAAGGCACTCCCTGGTCTCCA

CGACTCTTACATGGTAGCAATAACAGAATGAAAATCACATTTGGTATGGGGGCTTCACAA

TATTCGCATGACTGTCTGGAAGTAGACCATGCTATTTTTCTGCTCACTGTACACAAATAT

TGTTCACATAAACCCTATAATGTAAATATGAAATACAGTGATTACTCTTCTCACAGGCTG

ASTGTATGAATTCTAAAGACCCATAAGTATTAAAGTGGTAGGGATAAATTGGAAAAAAAA

AAAAAAAAAAAGAAAAACTTTAGAGCACACTGGCGGCCGTTACTAG

SEQ ID NO. 6: U37222_T2 | LENGTH: 1184
GCTCATTCATCTTTTAATTCACCCATAAAGGCTTTGAAAACTAAGGCTGGAGATGAACTT

ATAGGAGCCTGCCAGGCCGTGGAGAGTGAGGAAGCAGAGATGACGGAGATGATGTCTTTC

CTTGTCCTGTGAAATGGATTGTGGGTAGAGGTTCCGGAGATAATGCCTCTTGCTGGAAAC

AGTCTGGGCAGTTCTGTTCCCGCCATTCACAGAATTCTTCTCACTTTCTAGGTCTTCTTG

GTCCTAAGGGTGAGACAGGAGATGTTGGAATGACAGGAGCTGAAGGGCCACGGGGCTTCC

CCGGAACCCCTGGCAGGAAAGGAGAGCCTGGAGAAGCCGCTTATGTGTATCGCTCAGCGT

TCAGTGTGGGGCTGGAGACCCGCGTCACTGTTCCCAATGTACCCATTCGCTTTACTAAGA

TCTTCTACAACCAACAGAATCATTATGACGGCAGCACTGGCAAGTTCTACTGCAACATTC

CGGGACTCTACTACTTCTCTTACCACATCACGGTGTACATGAAAGATGTGAAGGTGAGCC

TCTTCAAGAAGGACAAGGCCGTTCTCTTCACCTACGACCAGTATCAGGAAAAGAATGTGG

ACCAGGCCTCTGGCTCTGTGCTCCTCCATCTGGAGGTGGGAGACCAAGTCTGGCTCCAGG

TGTATGGGGATGGGGACCACAATGGACTCTATGCAGATAACGTCAACGACTCTACATTTA

CTGGCTTTCTTCTCTACCATGATACCAACTGACTGCAACTACCCATAGCCCATACACCAG

GAGAATCATGGAACAGTCGACACACTTTCAGCTTAGTTTGAGAGATTGATTTTATTGCTT

AGTTTGAGAGTCCTGAGTATTATCCACACGTGTACTCACTTGTTCATTAAACGACTTTAT

AAAAAATAATTTGTGTTCCTAGTCCAGAAAAAAAGGCACTCCCTGGTCTCCACGACTCTT

ACATGGTAGCAATAACAGAATGAAAATCACATTTGGTATGGGGCTTCACAATATTCGCA

TGACTGTCTGGAAGTAGACCATGCTATTTTTCTGCTCACTGTACACAAATATTGTTCACA

TAAACCCTATAATGTAAATATGAAATACAGTGATTACTCTTCTCACAGGCTGAGTGTATG

AATTCTAAAGACCCATAAGTATTAAAGTGGTAGGGATAAATTGG

SEQ ID NO. 7: U37222_T3 | LENGTH: 1209
ATGAGACCTGGCCACTTTCTCCTCATTTCTGTCTGTACGATTGTCAGTGGATCTGACGAC

ACCAAAAGGGCTCAGGATGCTACTGTTGCAAGCTCTCCTGTTCCTCTTAATCCTGCCCAG

TCATGCCGAAGATGACGTTACTACAACTGAAGAGCTAGCTCCTGCTTTGGTCCCTCCACC

CAAGGGAACTTGTGCAGGTTGGATGGCAGGCATCCCAGGACATCCTGGCCACAATGGCAC

ACCAGGCCGTGATGGCAGAGATGGCACTCCTGGAGAGAAGGGAGAGAAGGAGATGCAGG

TCTTCTTGGTCCTAAGGGTGAGACAGGAGATGTTGGAATGACAGGAGCTGAAGGGCCACG

GGGCTTCCCCGGAACCCCTGGCAGGAAAGGAGAGCCTGGAGAAGCCGCGTCACTGTTCCC

TABLE 2-continued

```
AATGTACCCATTCGCTTTACTAAGATCTTCTACAACCAACAGAATCATTATGACGGCAGC

ACTGGCAAGTTCTACTGCAACATTCCGGGACTCTACTACTTCTCTTACCACATCACGGTG

TACATGAAAGATGTGAAGGTGAGCCTCTTCAAGAAGGACAAGGCCGTTCTCTTCACCTAC

GACCAGTATCAGGAAAAGAATGTGGACCAGGCCTCTGGCTCTGTGCTCCTCCATCTGGAG

GTGGGAGACCAAGTCTGGCTCCAGGTGTATGGGGATGGGGACCACAATGGACTCTATGCA

GATAACGTCAACGACTCTACATTTACTGGCTTTCTTCTCTACCATGATACCAACTGACTG

CAACTACCCATAGCCCATACACCAGGAGAATCATGGAACAGTCGACACACTTTCAGCTTA

GTTTGAGAGATTGATTTTATTGCTTAGTTTGAGAGTCCTGAGTATTATCCACACGTGTAC

TCACTTGTTCATTAAACGACTTTATAAAAAATAATTTGTGTTCCTAGTCCAGAAAAAAAG

GCACTCCCTGGTCTCCACGACTCTTACATGGTAGCAATAACAGAATGAAAATCACATTTG

GTATGGGGCTTCACAATATTCGCATGACTGTCTGGAAGTAGACCATGCTATTTTTCTGC

TCACTGTACACAAATATTGTTCACATAAACCCTATAATGTAAATATGAAATACAGTGATT

ACTCTTCTCACAGGCTGAGTGTATGAATTCTAAAGACCCATAAGTATTAAAGTGGTAGGG

ATAAATTGG

SEQ ID NO. 8: U37222_T4 | LENGTH: 1028
ATGAGACCTGGCCACTTTCTCCTCATTTCTGTCTGTACGATTGTCAGTGGATCTGACGAC

ACCAAAAGGGCTCAGGATGCTACTGTTGCAAGCTCTCCTGTTCCTCTTAATCCTGCCCAG

TCATGCCGAAGATGACGTTACTACAACTGAAGAGCTAGCTCCTGCTTTGGTCCCTCCACC

CAAGGGAACTTGTGCAGGTTGGATGCAGGCATCCCAGGACATCCTGGCCACAATGGCAC

ACCAGGCCGTGATGGCAGAGATGGCACTCCTGGAGAGAAGGGAGAGAAAGGAGATGCAGG

TCTTCTTGGTCCTAAGGGTGAGACAGGAGATGTTGGAATGACAGGAGCTGAAGGGCCACG

CGGCTTCCCCGGAACCCCTGGCAGGAAAGGAGAGCCTGGAGAAGCCGCTTATGTGTATCG

CTCAGCGTTCAGTGTGGGGCTGGAGACCCGCGTCACTGTTCCCAATGTACCCATTCGCTT

TACTAAGATCTTCTACAACCAACAGAATCATTATGACGGCAGCACTGGCAAGTTCTACTG

CAACATTCCGGGACTCTACATTTACTGGCTTTCTTCTCTACCATGATACCAACTGACTGC

AACTACCCATAGCCCATACACCAGGAGAATCATGGAACAGTCGACACACTTTCAGCTTAG

TTTGAGAGATTGATTTTATTGCTTAGTTTGAGAGTCCTGAGTATTATCCACACGTGTACT

CACTTGTTCATTAAACGACTTTATAAAAAATAATTTGTGTTCCTAGTCCAGAAAAAAAGG

CACTCCCTGGTCTCCACGACTCTTACATGGTAGCAATAACAGAATGAAAATCACATTTGG

TATGGGGCTTCACAATATTCGCATGACTGTCTGGAAGTAGACCATGCTATTTTTCTGCT

CACTGTACACAAATATTGTTCACATAAACCCTATAATGTAAATATGAAATACAGTGATTA

CTCTTCTCACAGGCTGAGTGTATGAATTCTAAAGACCCATAAGTATTAAAGTGGTAGGGA

TAAATTGG

SEQ ID NO. 9: U37222_T5 | LENGTH: 306
ATGAGACCTGGCCACTTTCTCCTCATTTCTGTCTGTACGATTGTCAGTGGATCTGACGAC

ACCAAAAGGGCTCAGGATGCTACTGTTGCAAGCTCTCCTGTTCCTCTTAATCCTGCCCAG

TCATGCCGAAGATGACGTTACTACAACTGAAGAGCTAGCTCCTGCTTTGGTCCCTCCACC

CAAGGGAACTTGTGCAGGTTGGATGCAGGCATCCCAGGACATCCTGGCCACATAAAAAT

ATAATTCGAGGGGCATCCACCAGGCCGGCTGAATTGTGCCAAAATATGGCACTTCCTGCA

AGATAA
```

TABLE 2-continued

SEQ ID 10-11 Ghrelin variants:
SEQ ID NO. 10: NM_016362_T1 | Length: 665
ACTCTGGATGGGTGCTGTTTAGACAAACGCCGTCTCCTATATAAGACCTGACAGCACAGG

CACCACTCCGCCAGGACTGCAGGCCCACCTGTCTGCAACCCAGCTGAGGCCATGCCCTCC

CCAGGGACCGTCTGCAGCCTCCTGCTCCTCGGCATGCTCTGGCTGGACTTGGCCATGGCA

GGCTCCAGCTTCCTGAGCCCTGAACACCAGAGAGTCCAGCAGAGAAAGGAGTCGAAGAAG

CCACCAGCCAAGCTGCAGCCCCGAGCTCTAGCAGGCTGGCTCCGCCCGGAAGATGGAGGT

CAAGCAGAAGGGGCAGAGGATGAACTGGAAGTCCGGTTCAACGCCCCCTTTGATGTTGGA

ATCAAGCTGTCAGGGGTTCAGTACCAGCAGCACAGCCAGGCCCTGGGGAAGTTTCTTCAG

GACATCCTCTGGGAAGAGGCCAAAGAGGCCCCAGCCGACAAGTGATCGCCCACAAGCCTT

ACTCACCTCTCTCTAAGTTTAGAAGCGCTCATCTGGCTTTTCGCTTGCTTCTGCAGCAAC

TCCCACGACTGTTGTACAAGCTCAGGAGGCGAATAAATGTTCAAACTGTATGCTGATGTT

CCAAATGGGAATTTATTTCAAAGAGGAAAAGTTAATATTTTACTTTAAAAAAATCAAAAT

AATAC

SEQ ID NO. 11: NM_016362_T2 | Length: 579
ACTCTGGATGGGTGCTGTTTAGACAAACGCCGTCTCCTATATAAGACCTGACAGCACAGG

CACCACTCCGCCAGGACTGCAGGCCCACCTGTCTGCAACCCAGCTGAGGCCATGCCCTCC

CCAGGGACCGTCTGCAGCCTCCTGCTCCTCGGCATGCTCTGGCTGGACTTGGCCATGGCA

GGCTCCAGCTTCCTGAGCCCTGAACACCAGAGAGTCCAGGTGAGACCTCCCCACAAAGCC

CCACATGTTGTTCCAGCCCTGCCACTTAGCAACCAGCTCTGTGACCTGGAGCAGCAGCGC

CATCTCTGGGCTTCAGTCTTCTCCCAGAGCACAAAGGACTCTGGGTCTGACCTCACTGTT

TCTGGAAGGACATGGGGGCTTAGAGTCCTAAACAGACTGTTTCCCCCTTCCAGCAGAGAA

AGGAGTCGAAGAAGCCACCAGCCAAGCTGCAGCCCCGAGCTCTAGCAGGCTGGCTCCGCC

CGGAAGATGGAGGTCAAGCAGAAGGGGCAGAGGATGAACTGGAAGTCCGGGTCGGTACCT

CTGCAGTTTTATGCTTCTGTGGCAGCGAGGAGGGTGGGG

SEQ ID 12-21 HSD11B variants:
SEQ ID 12: NM_005525_T1 WT| Length: 1448
GCACTGCCTGAGACTACTCCAGCCTCCCCCGTCCCTGATGTCACAATTCAGAGGCTGCTG

CCTGCTTAGGAGGTTGTAGAAAGCTCTGTAGGTTCTCTCTGTGTGTCCTACAGGAGTCTT

CAGGCCAGCTCCCTGTCGGATGGCTTTTATGAAAAAATATCTCCTCCCCATTCTGGGGCT

CTTCATGGCCTACTACTACTATTCTGCAAACGAGGAATTCAGACCAGAGATGCTCCAAGG

AAAGAAAGTGATTGTCACAGGGGCCAGCAAAGGGATCGGAAGAGAGATGGCTTATCATCT

GGCGAAGATGGGAGCCCATGTGGTGGTGACAGCGAGGTCAAAAGAAACTCTACAGAAGGT

GGTATCCCACTGCCTGGAGCTTGGAGCAGCCTCAGCACACTACATTGCTGGCACCATGGA

AGACATGACCTTCGCAGAGCAATTTGTTGCCCAAGCAGGAAAGCTCATGGGAGGACTAGA

CATGCTCATTCTCAACCACATCACCAACACTTCTTTGAATCTTTTTCATGATGATATTCA

CCATGTGCGCAAAAGCATGGAAGTCAACTTCCTCAGTTACGTGGTCCTGACTGTAGCTGC

CTTGCCCATGCTGAAGCAGAGCAATGGAAGCATTGTTGTCGTCTCCTCTCTGGCTGGGAA

AGTGGCTTATCCAATGGTTGCTGCCTATTCTGCAAGCAAGTTTGCTTTGGATCGGTTCTT

CTCCTCCATCAGAAAGGAATATTCAGTGTCCAGGGTCAATGTATCAATCACTCTCTGTGT

TCTTGGCCTCATAGACACAGAAACAGCCATGAAGGCAGTTTCTCGGATAGTCCATATGCA

AGCAGCTCCAAAGGAGGAATGTGCCCTGGAGATCATCAAAGGGGGAGCTCTGCGCCAAGA

TABLE 2-continued

AGAAGTGTATTATGACAGCTCACTCTGGACCACTCTTCTGATCAGAAATCCATGCAGGAA

GATCCTGGAATTTCTCTACTCAACGAGCTATAATATGGACAGATTCATAAACAAGTAGGA

ACTCCCTGAGGGCTGGGCATGCTGAGGGATTTTGGGACTGTTCTGTCTCATGTTTATCTG

AGCTCTTATCTATGAAGACATCTTCCCAGAGTGTCCCCAGAGACATGCAAGTCATGGGTC

ACACCTGACAAATGGAAGGAGTTCCTCTAACATTTGCAAAATGGAAATGTAATAATAATG

AATGTCATGCACCGCTGCAGCCAGCAGTTGTAAAATTGTTAGTAAACATAGGTATAATTA

CCAGATAGTTATATTAAATTTATATCTTATATATAATAATATGTGATGATTAATACAATA

TTAATTATAATAAAGGTCACATAAACTTTATAAATTCATAACTGGTAGCTATAACTTGAG

CTTATTCAGGATGGTTTCTTTAAAACCATAAACTGTACAAATGAAATTTTTCAATATTTG

TTTCTTAT

SEQ ID 13: NM_005525_T2 | LENGTH: 708
GCACTGCCTGAGACTACTCCAGCCTCCCCCGTCCCTGATGTCACAATTCAGAGGCTGCTG

CCTGCTTAGGAGGTTGTAGAAAGCTCTGTAGGTTCTCTCTGTGTGTCCTACAGGAGTCTT

CAGGCCAGCTCCCTGTCGGATGGCTTTTATGAAAAAATATCTCCTCCCCATTCTGGGGCT

CTTCATGGCCTACTACTACTATTCTGCAAACGAGGAATTCAGACCAGAGATGCTCCAAGG

AAAGAAAGTGATTGTCACAGGGGCCAGCAAAGGGATCGGAAGAGAGATGGCTTATCATCT

GGCGAAGATGGGAGCCCATGTGGTGGTGACAGCGAGCTCAGCACACTACATTGCTGGCAC

CATGGAAGACATGACCTTCGGAGAGCAATTTGTTGCCCAAGCAGGAAAGCTCATGGGAGG

ACTAGACATGCTCATTCTCAACCACATCACCAACACTTCTTTGAATCTTTTTCATGATGA

TATTCACCATGTGCGCAAAAGCATGGAAGTCAACTTCCTCAGTTACGTGGTCCTGACTGT

AGCTGCCTTGCCCATGCTGAAGCAGAGCAATGGAAGCATGTGCGCTCTTCTGCTGGAATG

CTATCATGTTGTGCATCTGAGCAGTNGTTGATGGTCTCTCTCATAGAAGATATCAGGCAG

GCATGATATACTTTGGTCTGCTATACCAGACGCTAGGCGTCTGATGCA

SEQ ID 14: NM_005525_T3 | LENGTH: 1394
GCACTGCCTGAGACTACTCCAGCCTCCCCCGTCCCTGATGTCACAATTCAGAGGCTGCTG

CCTGCTTAGGAGGTTGTAGAAAGCTCTGTAGGTTCTCTCTGTGTGTCCTACAGGAGTCTT

CAGGCCAGCTCCCTGTCGGATGGCTTTTATGAAAAAATATCTCCTCCCCATTCTGGGGCT

CTTCATGGCCTACTACTACTATTCTGCAAACGAGGAATTCAGACCAGAGATGCTCCAAGG

AAAGAAAGTGATTGTCACAGGGGCCAGCAAAGGGATCGGAAGAGAGATGGCTTATCATCT

GGCGAAGATGGGAGCCCATGTGGTGGTGACAGCGAGGTCAAAAGAAACTCTACAGAAGGT

GGTATCCCACTGCCTGGAGCTTGGAGCAGCCTCAGCACACTACATTGCTGGCACCATGGA

AGACATGACCTTCGCAGAGCAATTTGTTGCCCAAGCAGGAAAGCTCATGGGAGGACTAGA

CATGCTCATTCTCAACCACATCACCAACACTTCTTTGAATCTTTTTCATGATGATATTCA

CCATGTGCGCAAAAGCATGGAAGTCAACTTCCTCAGTTACGTGGTCCTGACTGTAGCTGC

CTTGCCCATGCTGAAGCAGAGCAATGGAAGCATTGTTGTCGTCTCCTCTCTGGCTGGGAA

AGTGGCTTATCCAATGGTTGCTGCCTATTCTGCAAGCAAGTTTGCTTTGGATGGGTTCTT

CTCCTCCATCAGAAAGGAATATTCAGTGTCCAGGGTCAATGTATCAATCACTCTCTGTGT

TCTTGGCCTCATAGACACAGAAACAGCCATGAAGGCAGTTTCTGGGATAGTCCATATGCA

AGCAGCTCCAAAGGAGGAATGTGCCCTGGAGATCATCAAAGGGGAGCTCTGCGCCAAGA

AGAAGTGTATTATGACAGCTCACTCTGGACCACTCTTCTGATCAGAAATCCATGCAGGAA

GATCCTGGAATTTCTCTACTCAACGAGCTATAATATGGAGGGACTGTTCTGTCTCATGTT

TABLE 2-continued

```
TATCTGAGCTCTTATCTATGAAGACATCTTCCCAGAGTGTCCCCAGAGACATGCAAGTCA

TGGGTCACACCTGACAAATGGAAGGAGTTCCTCTAACATTTGCAAAATGGAAATGTAATA

ATAATGAATGTCATGCACCGCTGCAGCCAGCAGTTGTAAAATTGTTAGTAAACATAGGTA

TAATTACCAGATAGTTATATTAAATTTATATCTTATATATAATAATATGTGATGATTAAT

ACAATATTAATTATAATAAAGGTCACATAAACTTTATAAATTCATAACTGGTAGCTATAA

CTTGAGCTTATTCAGGATGGTTTCTTTAAAACCATAAACTGTACAAATGAAATTTTTCAA

TATTTGTTTCTTAT

SEQ ID 15: NM_005525_T4 | LENGTH: 1394
GCACTGCCTGAGACTACTCCAGCCTCCCCCGTCCCTGATGTCACAATTCAGAGGCTGCTG

CCTGCTTAGGAGGTTGTAGAAAGCTCTGTAGGTTCTCTCTGTGTGTCCTACAGGAGTCTT

CAGGCCAGCTCCCTGTCGGATGGCTTTTATGAAAAAATATCTCCTCCCCATTCTGGGGCT

CTTCATGGCCTACTACTACTATTCTGCAAACGAGGAATTCAGACCAGAGATGCTCCAAGG

AAAGAAAGTGATTGTCACAGGGGCCAGCAAAGGGATCGGAAGAGAGATGGCTTATCATCT

GGCGAAGATGGGAGCCCATGTGGTGGTGACAGCGAGGTCAAAAGAAACTCTACAGAAGGT

GGTATCCCACTGCCTGGAGCTTGGAGCAGCCTCAGCACACTACATTGCTGGCACCATGGA

AGACATGACCTTCGCAGAGCAATTTGTTGCCCAAGCAGGAAAGCTCATGGGAGGACTAGA

CATGCTCATTCTCAACCACATCACCAACACTTCTTTGAATCTTTTTCATGATGATATTCA

CCATGTGCGCCCCATGCTGAAGCAGAGCAATGGAAGCATTGTTGTCGTCTCCTCTCTGGC

TGGGAAAGTGGCTTATCCAATGGTTGCTGCCTATTCTGCAAGCAAGTTTGCTTTGGATGG

GTTCTTCTCCTCCATCAGAAAGGAATATTCAGTGTCCAGGGTCAATGTATCAATCACTCT

CTGTGTTCTTGGCCTCATAGACACAGAAACAGCCATGAAGGCAGTTTCTGGGATAGTCCA

TATGCAAGCAGCTCCAAAGGAGGAATGTGCCCTGGAGATCATCAAAGGGGGAGCTCTGCG

CCAAGAAGAAGTGTATTATGACAGCTCACTCTGGACCACTCTTCTGATCAGAAATCCATG

CAGGAAGATCCTGGAATTTCTCTACTCAACGAGCTATAATATGGACAGATTCATAAACAA

GTAGGAACTCCCTGAGGGCTGGGCATGCTGAGGGATTTTGGGACTGTTCTGTCTCATGTT

TATCTGAGCTCTTATCTATGAAGACATCTTCCCAGAGTGTCCCCAGAGACATGCAAGTCA

TGGGTCACACCTGACAAATGGAAGGAGTTCCTCTAACATTTGCAAAATGGAAATGTAATA

ATAATGAATGTCATGCACCGCTGCAGCCAGCAGTTGTAAAATTGTTAGTAAACATAGGTA

TAATTACCAGATAGTTATATTAAATTTATATCTTATATATAATAATATGTGATGATTAAT

ACAATATTAATTATAATAAAGGTCACATAAACTTTATAAATTCATAACTGGTAGCTATAA

CTTGAGCTTATTCAGGATGGTTTCTTTAAAACCATAAACTGTACAAATGAAATTTTTCAA

TATTTGTTTCTTAT

SEQ ID 16: NM_005525_T5 | LENGTH: 1394
GCACTGCCTGAGACTACTCCAGCCTCCCCCGTCCCTGATGTCACAATTCAGAGCCTGCTG

CCTGCTTAGGAGGTTGTAGAAAGCTCTGTAGGTTCTCTCTGTGTGTCCTACAGGAGTCTT

CAGGCCAGCTCCCTGTCGGATGGCTTTTATGAAAAAATATCTCCTCCCCATTCTGGGGCT

CTTCATGGCCTACTACTACTATTCTGCAAACGAGGAATTCAGACCAGAGATGCTCCAAGG

AAAGAAAGTGATTGTCACAGGGGCCAGCAAAGGGATCGGAAGAGAGATGGCTTATCATCT

GGCGAAGATGGGAGCCCATGTGGTGGTGACAGCGAGCTCAGCACACTACATTGCTGGCAC

CATGGAAGACATGACCTTCGCAGAGCAATTTGTTGCCCAAGCAGGAAAGCTCATGGGAGG
```

TABLE 2-continued

```
ACTAGACATGCTCATTCTCAACCACATCACCAACACTTCTTTGAATCTTTTTCATGATGA
TATTCACCATGTGCGCAAAAGCATGGAAGTCAACTTCCTCAGTTACGTGGTCCTGACTGT
AGCTGCCTTGCCCATGCTGAAGCAGAGCAATGGAAGCATTGTTGTCGTCTCCTCTCTGGC
TGGGAAAGTGGCTTATCCAATGGTTGCTGCCTATTCTGCAAGCAAGTTTGCTTTGGATGG
GTTCTTCTCCTCCATCAGAAAGGAATATTCAGTGTCCAGGGTCAATGTATCAATCACTCT
CTGTGTTCTTGGCCTCATAGACACAGAAACAGCCATGAAGGCAGTTTCTGGGATAGTCCA
TATGCAAGCAGCTCCAAAGGAGGAATGTGCGCTGGAGATCATCAAAGGGGGAGCTCTGCG
CCAAGAAGAAGTGTATTATGACAGCTCACTCTGGACCACTCTTCTGATCAGAAATCCATC
CAGGAAGATCCTGGAATTTCTCTACTCAACGAGCTATAATATGGACAGATTCATAAACAA
GTAGGAACTCCCTGAGGGCTGGGCATGCTGAGGGATTTTGGGACTGTTCTGTCTCATGTT
TATCTGAGCTCTTATCTATGAAGACATCTTCCCAGAGTGTCCCCAGAGACATGCAAGTCA
TGGGTCACACCTGACAAATGGAAGGAGTTCCTCTAACATTTGCAAAATGGAAATGTAATA
ATAATGAATGTCATGCACCGCTGCAGCCAGCAGTTGTAAAATTGTTAGTAAACATAGGTA
TAATTACCAGATAGTTATATTAAATTTATATCTTATATATAATAATATGTGATGATTAAT
ACAATATTAATTATAATAAAGGTCACATAAACTTTATAAATTCATAACTGGTAGCTATAA
CTTGAGCTTATTCAGGATGGTTTCTTTAAAACCATAAACTGTACAAATGAAATTTTTCAA
TATTTGTTTCTTAT

SEQ ID 17: NM_005525_T6 | LENGTH: 1821
GGTGAAAAGGGAAAACCTGCCCAAATCCAGTTTTTGTTTCAGTAACTTCCTTTGAGACAA
AGTCAGGAATCTGAGAGTAAGCACCTGCTAAGGGTGGGACAGGGGCTCTGTCTGGTATGC
CTCTCCCATGTTAAGAGCTAACAATAGTAATGGATAAGTCTCCAGGGCAACCAGGACCAC
TTCCAAGCATTCCTGTCTTGGGCTGCCTCGAGGGCTCCTCTGTCCTTTGGGGAGTACTGA
TTGATGCCTGATGCCCAGAACTGGCCCACTCTGGCTTCTCTTTGGAGCTGTCTCTGCAGG
CGCCTTCTGGCTGCCAGCTCGGTCCTAGCATAAGGGACTTCTTCCTTGGCCTGGGTTTCA
CCTTCTTGTATCAGGTGGCAGACCAGCTGGTTTCAGTCCCAAATCAGGTCTTCTGACTCC
TCCCAGAAACCAACCAACTTCTGAGCAGGAAATCCTGCCCCTCCCCAAAGAGTGGGAAAC
GCGAAAGGAAGAGAGAGATGAAACAGAAGGAAAGGCAGAGGAGGAGGAGAGAGAGAA
GAGAAGAAAAAGAAAAAGAACATCAATAAAAAGAAGTCAGATTTGTTCGAAATCTTGAG
AGATGCTCCAAGGAAAGAAAGTGATTGTCACAGGGGCCAGCAAAGGGATCGGAAGAGAGA
TGGCTTATCATCTGGCGAAGATGGGAGCCCATGTGGTGGTGACAGCGAGGTCAAAAGAAA
CTCTACAGAAGGTGGTATCCCACTGCCTGGAGCTTGGAGCAGCCTCAGCACACTACATTG
CTGGCACCATGGAAGACATGACCTTCGCAGAGCAATTTGTTGCCCAAGCAGGAAAGCTCA
TGGGAGGACTAGACATGCTCATTCTCAACCACATCACCAACACTTCTTTGAATCTTTTTC
ATGATGATATTCACCATGTGCGCAAAAGCATGGAAGTCAACTTCCTCAGTTACGTGGTCC
TGACTGTAGCTGCCTTGCCGATGCTGAAGCAGAGCAATGGAAGCATTGTTGTCGTCTCCT
CTCTGGCTGGGAAAGTGGCTTATCCAATGGTTGCTGCCTATTCTGCAAGCAAGTTTGCTT
TGGATGGGTTCTTCTCCTCCATCAGAAAGGAATATTCAGTGTCCAGGGTCAATGTATCAA
TCACTCTCTGTGTTCTTGGCCTCATAGACACAGAAACAGCCATGAAGGCAGTTTCTGGGA
TAGTCCATATGCAAGCAGCTCCAAAGGAGGAATGTGCCCTGGAGATCATCAAAGGGGGAG
CTCTGCGCCAAGAAGAAGTGTATTATGACAGCTCACTCTGGACCACTCTTCTGATCAGAA
```

TABLE 2-continued

ATCCATGCAGGAAGATCCTGGAATTTCTCTACTCAACGAGCTATAATATGGACAGATTCA

TAAACAAGTAGGAACTCCCTGAGGGCTGGGCATGCTGAGGGATTTTGGGACTGTTCTGTC

TCATGTTTATCTGAGCTCTTATCTATGAAGACATCTTCCCAGAGTGTCCCCAGAGACATG

CAAGTCATGGGTCACACCTGACAAATGGAAGGAGTTCCTCTAACATTTGCAAAATGGAAA

TGTAATAATAATGAATGTCATGCACCGCTGCAGCCAGCAGTTGTAAAATTGTTAGTAAAC

ATAGGTATAATTACCAGATAGTTATATTAAATTTATATCTTATATATAATAATATGTGAT

GATTAATACAATATTAATTATAATAAAGGTCACATAAACTTTATAAATTCATAACTGGTA

GCTATAACTTGAGCTTATTCAGGATGGTTTCTTTAAAACCATAAACTGTACAAATGAAAT

TTTTCAATATTTGTTTCTTAT

SEQ ID 18: NM_005525_T7 | LENGTH: 1304
GCACTGCCTGAGACTACTCCAGCCTCCCCCGTCCCTGATGTCACAATTCAGAGGCTGCTG

CCTGCTTAGGAGGTTGTAGAAAGCTCTGTAGGTTCTCTCTGTGTGTCCTACAGGAGTGTT

CAGGCCAGCTCCCTGTCGGATGGCTTTTATGAAAAAATATCTCCTCCCCATTCTGGGGCT

CTTCATGGCCTACTACTACTATTCTGCAAACGAGGAATTCAGACCAGAGATGCTCCAAGG

AAAGAAAGTGATTGTCACAGGGGCCAGCAAAGGGATCGGAAGAGAGATGGCTTATCATCT

GGCGAAGATGGGAGCCCATGTGGTGGTGACAGCGAGGTCAAAAGAAACTCTACAGAAGGT

GGTATCCCACTGCCTGGAGCTTGGAGCAGCCTCAGCACACTACATTGCTGGCACCATGGA

AGACATGACCTTCGCAGAGCAATTTGTTGCCCAAGCAGGAAAGCTCATGGGAGGACTAGA

CATGCTCATTCTCAACCACATCACCAACACTTCTTTGAATCTTTTTCATGATGATATTCA

CCATGTGCGCAAAAGCATGGAAGTCAACTTCCTCAGTTACGTGGTCCTGACTGTAGCTGC

CTTGCCCATGCTGAAGCAGAGCAATGGAAGCATTGTTGTCGTCTCCTCTCTGGCTGAAAC

AGCCATGAAGGCAGTTTCTGGGATAGTCCATATGCAAGCAGCTCCAAAGGAGGAATGTGC

CCTGGAGATCATCAAAGGGGGAGCTCTGCGCCAAGAAGAAGTGTATTATGACAGCTCACT

CTGCACCACTCTTCTGATCAGAAATCCATGCAGGAAGATCCTGGAATTTCTCTACTCAAC

GAGCTATAATATGGACAGATTCATAAACAAGTAGGAACTCCCTGAGGGCTGGGCATGCTG

AGGGATTTTGGGACTGTTCTGTCTCATGTTTATCTGAGCTCTTATCTATGAAGACATCTT

CCCAGAGTGTCCCCAGAGACATGCAAGTCATGGGTCACACCTGACAAATGGAAGGAGTTC

CTCTAACATTTGCAAAATGGAAATGTAATAATAATGAATGTCATGCACCGCTGCAGCCAG

CAGTTGTAAAATTCTTAGTAAACATAGGTATAATTACCAGATAGTTATATTAAATTTATA

TCTTATATATAATAATATGTCATGATTAATACAATATTAATTATAATAAAGGTCACATAA

ACTTTATAAATTCATAACTGGTAGCTATAACTTGAGCTTATTCAGGATGGTTTCTTTAAA

ACCATAAACTGTACAAATGAAATTTTTCAATATTTGTTTCTTAT

SEQ ID 19: XM_110304_T1 | Length: 1307 WT
ACTGTTGGCCTCTGGAWTCAGAGGCTGCTGCCTGCCTGGGAGGTTGTAGAAAGCTCTGCA

GGTTTTCTTCGTGTGTCCTACAGGGCGCCCTGACCCAGGTCCCTGTTTGATGGCAGTTAT

GAAAAATTACCTCCTCCCGATCCTGGTGCTCTTCCTGGCCTACTACTACTATTCTACAAA

TGAAGAGTTCAGACCAGAAATGCTCCAGGGAAAGAAAGTGATTGTCACTGGGGCCAGCAA

AGGGATTGGAAGAGAAATGGCATATCATCTGTCAAAAATGGGAGCCCATGTGGTATTGAC

TGCCAGGTCGGAGGAAGGTCTCCAGAAGGTAGTGTCTCGCTGCCTTGAACTCGGAGCAGC

CTCTGCTCACTACATTGCTGGCACTATGGAAGACATGACATTTGCGGAGCAATTTATTGT

CAAGGCGGGAAAGCTCATGGGCGGACTGGACATGCTTATTCTAAACCACATCACTCAGAC

TABLE 2-continued

CTCGCTGTCTCTCTTCCATGACGACATCCACTCTGTGCGAAGAGTCATGGAGGTCAACTT

CCTCAGCTACGTGGTCATGAGCACAGCCGCCTTGCCCATGCTGAAGCAGAGCAATGGCAG

CATTGCCGTCATCTCCTCCTTGGCTGGGAAAATGACCCAGCCTATGATTGCTCCCTACTC

TGCAAGCAAGTTTGCTCTGGATGGGTTCTTTTCCACCATTAGAACAGAACTCTACATAAC

CAAGGTCAACGTGTCCATCACTCTCTGTGTCCTTGGCCTCATAGACACAGAAACAGCTAT

GAAGGAAATCTCTGGGATAATTAACGCCCAAGCTTCTCCCAAGGAGGAGTGCCCCCTGGA

GATCATCAAAGCCACAGCTCTACGCAAAACCGAGGTGTACTATGACAAATCGCCTTTGAC

TCCAATCCTGCTTGGGAACCCAGGAAGGAAGATCATGGAATTTTTTTCATTACGATATTA

TAATAAGGACATGTTTGTAAGTAACTAGGAACTCCTGACCCCTCGTGAGTGGTCTTAGAA

CACTCCTCCCTGATACTTCTGTAAGCCCTACCCACAAAAGTATCTTTCCAGAGATACACA

AATTTTGGGGTACACCTCATCATGAGAAATTCTTGCAACACTTGCACAGTGAAAATGTAA

TTGTAATAAATGTCACAAACCACTTTGGGGCCTGCAGTTGTGAACTTGATTGTAACTATG

GATATAACACATAGTGGTTGTATCGCCTTTACCTCACACTGAATGAAAACAATGATAACT

AATGTAACATTAATATAATAAAGGTAATATCAACTTTGTAAATCCA

SEQ ID 20: XM_110304_T3 | Length: 1181
ACTGTTGGCCTCTGGAWTCAGAGGCTGCTGCCTGCCTGGGAGGTTGTAGAAAGCTCTGCA

GGTTTTCTTCGTCTGTCCTACAGGGCGCCCTGAGCCAGGTCCCTGTTTGATGGCAGTTAT

GAAAAATTACCTCCTCCCGATCCTGGTGCTCTTCCTGGCCTACTACTACTATTCTACAAA

TGAAGAGTTCAGACTCCAGAAGGTAGTGTCTCGCTGCCTTGAACTCGGAGCAGCCTCTGC

TCACTACATTGCTGGCACTATGGAAGACATGACATTTGCGGAGCAATTTATTGTCAAGGC

GGGAAAGCTCATGGGCGGACTGGACATGCTTATTCTAAACCACATCACTCAGACCTCGCT

GTCTCTCTTCCATGACGACATCCACTCTGTGCGAAGAGTCATGGAGGTCAACTTCCTCAG

CTACGTGGTCATGAGCACAGCCGCCTTGCCCATGCTGAAGCAGAGCAATGGCAGCATTGC

CGTCATCTCCTCCTTGGCTGGGAAAATGACCCAGCCTATGATTGCTCCCTACTCTGCAAG

CAAGTTTGCTCTGGATGGGTTCTTTTCCACCATTAGAACAGAACTCTACATAACCAAGGT

CAACCTCTCCATCACTCTCTGTGTCCTTGGCCTCATACACACAGAAACAGCTATGAAGGA

AATCTCTGGGATAATTAACGCCCAAGCTTCTCCCAAGGAGGAGTCCGCCCTGGAGATCAT

CAAAGGCACAGCTCTACGCAAAAGCGAGGTGTACTATGACAAATCGCCTTTGACTCCAAT

CCTGCTTGGGAACCCAGGAAGGAAGATCATGGAATTTTTTTCATTACGATATTATAATAA

GGACATGTTTGTAAGTAACTAGGAACTCCTGAGCCCTGGTGAGTGGTCTTAGAACAGTCC

TGCCTGATACTTCTGTAAGCCCTACCCACAAAAGTATCTTTCCAGAGATACACAAATTTT

GGGGTACACCTCATCATGAGAAATTCTTGCAACACTTGCACAGTGAAAATGTAATTGTAA

TAAATGTCACAAACCACTTTGGGGCCTGCAGTTGTGAACTTGATTGTAACTATGGATATA

AACACATAGTGGTTGTATCGGCTTTACCTCACACTGAATGAAACAATGATAACTAATGTA

ACATTAAATATAATAAAGGTAATATCAACTTTGTAAATGCA

SEQ ID 21: XM_110304_T4 | Length: 845
ACTGTTGGCCTCTGGAWTCAGAGGCTGCTGCCTGCCTGGGAGGTTGTAGAAAGCTCTGCA

GGTTTTCTTCGTGTGTCCTACAGGGCGCCCTGAGCCAGGTCCCTGTTTGATGGCAGTTAT

GAAAAATTACCTCCTCCCGATCCTGGTGCTCTTCCTGGCCTACTACTACTATTCTACAAA

TGAAGAGTTCAGACCAGAAATGCTCCAGGGAAAGAAAGTGATTGTCACTGGGGCCAGCAA

TABLE 2-continued

```
AGGGATTGGAAGAGAAATGGCATATCATCTGTCAAAAATGGGAGCCCATGTGGTATTGAC

TGCCAGGTCGGAGGAAGGTCTCCAGAAGGTAGTGTCTCGCTGCCTTGAACTCGGAGCAGC

CTCTGCTCACTACATTGCTGGCACTATGGAAGACATGACATTTGCGGAGCAATTTATTGT

CAAGGCGGGAAAGCTCATGGGCGGACTGGACATGCTTATTCTAAACCACATCACTCAGAC

CTCGCTGTCTCTCTTCCATGACGACATCCACTCTGTGCGAAGAGTCATGGAGGTCAACTT

CCTCAGCTACGTGGTCATGAGCACAGCCGCCTTGCCCATGCTGAAGCAGAGCAATGGCAG

CATTGCCGTCATCTCCTCCTTGCCTGGGGGAAGAACAGTTCCACAACAGAGAAGTCGCAG

TGTTACTCCTGACTCCCGCGGCCCGTGATTAATATCACCAGCCACAGAATGGACTGGAAC

CCTCTATCGATCTGGTGGGATTGGATATAACGAACATAGAATTACTCCTGAGACTACCAG

AACTGAATAGTTCAAATCAAATCATGCCAGAATATCAGACAAATCCAAATGGCAAAACAG

TTGCA
```

SEQ ID 22–30 Adiponectin variants products:
SEQ ID NO. 22: NP_004788_P1 | Length: 244 | Transcript: 1 WT
MLLLGAVLLLLALPGHDQETTTQGPGVLLPLPKGACTGWMAGIPGHPGHNGAPGRDGRDG

TPGEKGEKGDPGLIGPKGDIGETGVPGAEGPRGFPGIQGRKGEPGEGAYVYRSAFSVGLE

TYVTIPNMPIRFTKIFYNQQNHYDGSTGKFHCNIPGLYYFAYHITVYMKDVKVSLFKKDK

AMLFTYDQYQENNVDQASGSVLLHLEVGDQVWLQVYGEGERNGLYADNDNDSTFTGFLLY

HDTN

SEQ ID NO. 23: NP_004788_P2 | Length: 160 | Transcript: 2
MPGAEGPRGFPGIQGRKGEPGEGAYVYRSAFSVGLETYVTIPNMPIRFTKIFYNQQNHYD

GSTGKFHCNIPGLYYFAYHITVYMKDVKVSLFKKDKAMLFTYDQYQENNVDQASGSVLLH

LEVGDQVWLQVYGEGERNGLYADNDNDSTFTGFLLYHDTN

SEQ ID NO. 24: NP_004788_P3 | Length: 153 | Transcript: 3
MLLLGAVLLLLALPGHDQETTTQGPGVLLPLPKGACTGWMAGIPGHPGHNGAPGRDGRDG

TPGEKGEKGDPGLIGPKGDIGETGVPGAEGPRGFPGIQGRKGEPGEGALLSPTCPFALPR

SSTISKTTMMAPLVNSTATFLGCTTLPTTSQSI

SEQ ID NO. 25: NP_004788_P4 | Length: 166 | Transcript: 4
MLLLGAVLLLLALPGHDQETTTQGPGVLLPLPKGACTGWMAGIPGHPGHNGAPGRDGRDG

TPGEKGEKGDPGLIGPKGDIGETGVPGAEGPRGFPGIQGRKGEPGEGAYVYRSAFSVGLE

TYVTIPNMPIRFTKIFYNQQNHYDGSTGKFHCNIPGLYLNRLSSLP

SEQ ID NO. 26: NP_033735_P1 | Length: 247 | Transcript: 1 WT
MLLLQALLFLLILPSHAEDDVTTTEELAPALVPPPKGTCAGWMAGIPGHPGHNGTPGRDG

RDGTPGEKGEKGDAGLLGPKGETGDVGMTGAEGPRGFPGTPGRKGEPGEAAYMYRSAFSV

GLETRVTVPNVPIRFTKIFYNQQNHYDGSTGKFYCNIPGLYYFSYHITVYMKDVKVSLFK

KDKAVLFTYDQYQEKNVDQASGSVLLHLEVGDQVWLQVYGDGDHNGLYADNVNDSTFTGF

LLYHDTN

SEQ ID NO. 27: NP_033735_P2 | Length: 160 | Transcript: 2
MTGAEGPRGFPGTPGRKGEPGEAAYVYRSAFSVGLETRVTVPNVPIRFTKIFYNQQNHYD

GSTGKFYCNIPGLYYFSYHITVYMKDVKVSLFKKDKAVLFTYDQYQEKNVDQASGSVLLH

LEVGDQVWLQVYGDGDHNGLYADNVNDSTFTGFLLYHDTN

SEQ ID NO. 28: NP_033735_P3 | Length: 156 | Transcript: 3
MLLLQALLFLLILPSHAEDDVTTTEELAPALVPPPKGTCAGWMAGIPGHPGHNGTPGRDG

RDGTPGEKGEKGDAGLLGPKGETGDVGMTGAEGPRGFPGTPGRKGEPGEAASLFPMYPFA

LLRSSTTNRIIMTAALASSTATFRDSTTSLTTSRCT

TABLE 2-continued

SEQ ID NO. 29: NP_033735_P4 | Length: 169 | Transcript: 4
MLLLQALLFLLILPSHAEDDVTTTEELAPALVPPPKGTCAGWMAGIPGHPGHNGTPGRDG

RDGTPGEKGEKGDAGLLGPKGETGDVGMTGAEGPRGFPGTPGRKGEPGEAAYVYRSAFSV

GLETRVTVPNVPIRFTKIFYNQQNHYDGSTGKFYCNIPGLYIYWLSSLP

SEQ ID NO. 30: NP_033735_P5 | Length: 76 | Transcript: 5
MLLLQALLFLLILPSHAEDDVTTTEELAPALVPPPKGTCAGWMAGIPGHPGHIKIKFEGH

PPGRLNCAKIWHFLQD

SEQ ID 31-32 Ghrelin variants:
SEQ ID NO. 31: NP_057446 | Length: 117 | Transcript: 1 WT
MPSPGTVCSLLLLGMLWLDLAMAGSSFLSPEHQRVQQRKESKKPPAKLQPRALAGWLRPE

DGGQAEGAEDELEVRFNAPFDVGIKLSGVQYQQHSQALGKFLQDILWEEAKEAPADK

SEQ ID NO. 32: NP_057446 | Length: 117 | Transcript: 2
MPSPGTVCSLLLLGMLWLDLAMAGSSFLSPEHQRVQVRPPHKAPHVVPALPLSNQLCDLE

QQRHWASVFSQSTKDSGSDLTVSGRTWGLRVLNRLFPPSSRERSRRSHQPSCSPEL

SEQ ID 33-42 HSD11B variants:
SEQ ID NO. 33: NP_005516 | Length: 292 | Transcript: 1 WT
MAFMKKYLLPILGLFMAYYYYSANEEFRPEMLQGKKVIVTGASKGIGREMAYHLAKMGAH

VVVTARSKETLQKVVSHCLELGAASAHYIAGTMEDMTFAEQFVAQAGKLMGGLDMLILNH

ITNTSLNLFHDDIHHVRKSMEVNFLSYVVLTVAALPMLKQSNGSIVVVSSLAGKVAYPMV

AAYSASKFALDGPFSSIRKEYSVSRVNVSITLCVLGLIDTETAMKAVSGIVHMQAAPKEE

CALEIIKGGALRQEEVYYDSSLWTTLLIRNPCRKILEFLYSTSYNMDRFINK

SEQ ID NO. 34: NP_005516 | Length: 163 | Transcript: 2
MAFMKKYLLPILGLFMAYYYYSANEEFRPEMLQGKKVIVTGASKGIGREMAYHLAKMGAH

VVVTASSAHYIAGTMEDMTFAEQFVAQAGKLMGGLDMLILNHITNTSLNLFEDDIHHVRK

SMEVNFLSYVVLTVAALPMLKQSNGSMCALLLECYHVVHLSSX

SEQ ID NO. 35: NP_005516 | Length: 295 | Transcript: 3
MAFNKKYLLPILGLFMAYYYYSANEEFRPEMLQGKKVIVTGASKGIGREMAYHLAKMGAH

VVVTARSKETLQKVVSHCLELGAASAHYIAGTMEDMTFAEQFVAQAGKLMGGLDMLILNH

ITNTSLNLFHDDIHHVRKSMEVNFLSYVVLTVAALPMLKQSNGSIVVVSSLAGKVAYPMV

AAYSASKFALDGFFSSIRKEYSVSRVNVSITLCVLGLIDTETAMKAVSGIVHMQAAPKEE

CALEIIKGGALRQEEVYYDSSLWTTLLIRNPCRKILEFLYSTSYNMEGLFCLMFI

SEQ ID NO. 36: NP_005516 | Length: 274 | Transcript: 4
MAFMKKYLLPILGLFMAYYYYSANEEFRPEMLQGKKVIVTGASKGIGREMAYHLAKMGAH

VVVTARSKETLQKVVSHCLELGAASAHYIAGTMEDMTFAEQFVAQAGKLMGGLDMLILNH

ITNTSLNLFHDDIHHVRPMLKQSNGSIVVVSSLAGKVAYPMVAAYSASKFALDGFFSSIR

KEYSVSRVNVSITLCVLGLIDTETAMKAVSGIVHMQAAPKEECALEIIKGGALRQEEVYY

DSSLWTTLLIRNPCRKILEFLYSTSYNMDRFINK

SEQ ID NO. 37: NP_005516 | Length: 274 | Transcript: 5
MAFMKKYLLPILGLFMAYYYYSANEEFRPEMLQGKKVIVTGASKGIGREMAYHLAKMGAH

VVVTASSAHYIAGTMEDMTFAEQFVAQAGKLMGGLDMLILNHITNTSLNLFHDDIHHVRK

SMEVNFLSYVVLTVAALPMLKQSNGSIVVVSSLAGKVAYPMVAAYSASKFALDGFFSSIR

KEYSVSRVNVSITLCVLGLIDTETAMKAVSGIVHMQAAPKEECALEIIKGGALRQEEVYY

DSSLWTTLLIRNPCRKILEFLYSTSYNMDRFINK

SEQ ID NO. 38: NP_005516 | Length: 262 | Transcript: 6
MLQGKKVIVTGASKGIGREMAYHLAKMGAHVVVTARSKETLQKVVSHCLELGAASAHYIA TABLE 2-continued

```
GTMEDMTFAEQFVAQAGKLMGGLDMLILNHITNTSLNLFHDDIHHVRKSMEVNFLSYVVL

TVAALPMLKQSNGSIVVVSSLAGKVAYPMVAAYSASKFALDGFFSSIRKEYSVSRVNVSI

TLCVLGLIDTETAMKAVSGIVHMQAAPKEECALEIIKGGALRQEEVYYDSSLWTTLLIRN

PCRKILEFLYSTSYNMDRFINK

SEQ ID NO. 39: NP_005516 | Length: 244 | Transcript: 7
MAFMKKYLLPILGLFMAYYYYSANEEFRPEMLQGKKVIVTGASKGIGREMAYHLAKMGAH

VVVTARSKETLQKVVSHCLELGAASAHYIAGTMEDMTFAEQFVAQAGKLMGGLDMLILNH

ITNTSLNLFHDDIHHVRKSMEVNFLSYVVLTVAALPMLKQSNGSIVVVSSLAETAMKAVS

GIVHMQAAPKEECALEIIKGGALRQEEVYYDSSLWTTLLIRNPCRKILEFLYSTSYNMDR

FINK

SEQ ID NO. 40: XP_110304| Length: 292 | Transcript: 1 WT
MAVMKNYLLPILVLFLAYYYYSTNEEFRPEMLQGKKVIVTGASKGIGREMAYHLSKMGAH

VVLTARSEEGLQKVVSRCLELGAASAHYIAGTMEDMTFAEQFIVKAGKLMGGLDMLILNH

ITQTSLSLFHDDIHSVRRVMEVNFLSYVVMSTAALPMLKQSNGSIAVISSLAGKMTQPMI

APYSASKFALDGFFSTIRTELYITKVNVSITLCVLGLIDTETAMKEISGIINAQASPKEE

CALEIIKGTALRKSEVYYDKSPLTPILLGNPGRKIMEFFSLRYYNKDMFVSN

SEQ ID NO. 41: XP_110304| Length: 250 | Transcript: 8
MAVMKNYLLPILVLFLAYYYYSTNEEFRLQKVVSRCLELGAASAHYIAGTMEDMTFAEQF

IVKAGKLMGGLDMLILNHITQTSLSLFHDDIHSVRRVMEVNFLSYVVMSTAALPMLKQSN

GSIAVISSLAGKMTQPMIAPYSASKFALDGFFSTIRTELYITKVNVSITLCVLGLIDTET

AMKEISGIINAQASPKEECALEIIKGTALRKSEVYYDKSPLTPILLGNPGRKIMEFFSLR

YYNKDMFVSN

SEQ ID NO. 42: XP_110304| Length: 192 | Transcript: 9
MAVMKNYLLPILVLFLAYYYYSTNEEFRPEMLQGKKVIVTGASKGIGREMAYHLSKMGAH

VVLTARSEEGLQKVVSRCLELGAASAHYIAGTMEDMTFAEQFIVKAGKLMGGLDMLILNH

ITQTSLSLFHDDIHSVRRVMEVNFLSYVVMSTAALPMLKQSNGSIAVISSLAGGRTVPQQ

RSRSVTPDSRGP
```

"obesity and/or diabetes Variants products—also referred at times as the "obesity and/or diabetes variants proteins" or "obesity and/or diabetes variants polypeptides"—is an amino acid sequence encoded by the obesity and/or diabetes variants nucleic acid sequences which is a naturally occurring mRNA sequence obtained as a result of alternative splicing. The amino acid sequences may be a peptide, a protein, as well as peptides or proteins having chemically modified amino acids (see below) such as a glycopeptide or glycoprotein. The obesity and/or diabetes variants products are shown in any one of SEQ ID NO: 22 to SEQ ID NO: 42. The term also includes homologs (see below) of said sequences in which one or more amino acids has been added, deleted, substituted (see below) or chemically modified (see below) as well as fragments (see below) of this sequence having at least 10 amino acids.

"Fragments of obesity and/or diabetes related variants nucleic acid sequences"—a partial sequence of any one of SEQ ID NO:1 to SEQ ID NO:21 which includes the regions which contains the variation in nucleotides between the variant and the original sequences. These regions (in the amino acid level) are as depicted in the above Table 1.

"Fragments of obesity and/or diabetes related variant product"—amino acid sequences coded by the above nucleic acid fragment, containing regions by which the variant differs from the original sequence as indicated in Table 1.

"Nucleic acid sequence"—a sequence composed of DNA nucleotides, RNA nucleotides or a combination of both types and may includes natural nucleotides, chemically modified nucleotides and synthetic nucleotides.

"Amino acid sequence"—a sequence composed of any one of the 20 naturally appearing amino acids, amino acids which have been chemically modified (see below), or composed of synthetic amino acids.

"Homologues of variants/products"—amino acid sequences of variants in which one or more amino acids has been added, deleted or replaced. The altered amino acid shall be in regions where the variant differs from the original sequence, for example, according to the explanation in Table 1.

"Conservative substitution"—refers to the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

"Non-conservative substitution"—refers to the substitution of an amino acid in one class with an amino acid from another class; for example, substitution of an Ala, a class H residue, with a class III residue such as Asp, Asn, Glu, or Gln.

"Chemically modified"—when referring to the product of the invention, means a product (protein) where at least one of its amino acid resides is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristlyation, pegylation, prenylation, phosphorylation, ubiqutination, or any similar process.

"Biologically active"—refers to the variant product having some sort of biological activity, for example, capability of binding to the obesity and/or diabetes related gene or to other agonists of the original obesity and/or diabetes related gene as known.

"Immunologically active" defines the capability of a natural, recombinant or synthetic varient product, or any fragment thereof, to induce a specific immune response in appropriate animals or cells and to bind with specific antibodies. Thus, for example, an immunologically active fragment of variant product denotes a fragment which retains some or all of the immunological properties of the variant product, e.g can bind specific anti-variant product antibodies or which can elicit an immune response which will generate such antibodies or cause proliferation of specific immune cells which produce variant.

"Optimal alignment"—is defined as an alignment giving the highest percent identity score. Such alignment can be performed using a variety of commercially available sequence analysis programs, such as the local alignment program LALIGN using a ktup of 1, default parameters and the default PAM. A preferred alignment is the one performed using the CLUSTAL-W program from MacVector™, operated with an open gap penalty of 10.0, an extended gap penalty of 0.1, and a BLOSUM similarity matrix. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence). In case of alignments of known gene sequences with that of the new variant, the optimal alignment invariably included aligning the identical parts of both sequences together, then keeping apart and unaligned the sections of the sequences that differ one from the other.

"Having at least 90% identity"—with respect to two amino acid or nucleic acid sequence sequences, refers to the percentage of residues that are identical in the two sequences when the sequences are optimally aligned. Thus, 90% amino acid sequence identity means that 90% of the amino acids in two or more optimally aligned polypeptide sequences are identical.

"Isolated nucleic acid molecule having an variant nucleic acid sequence"—is a nucleic acid molecule that includes the obesity and/or diabetes related variant nucleic acid coding sequence. Said isolated nucleic acid molecule may include the obesity and/or diabetes related variant nucleic acid sequence as an independent insert; may include the obesity and/or diabetes related variant nucleic acid sequence fused to an additional coding sequences, encoding together a fusion protein in which the variant coding sequence is the dominant coding sequence (for example, the additional coding sequence may code for a signal peptide); the obesity and/or diabetes related variant nucleic acid sequence may be in combination with non-coding sequences, e.g., introns or control elements, such as promoter and terminator elements or 5' and/or 3' untranslated regions, effective for expression of the coding sequence in a suitable host; or may be a vector in which the obesity and/or diabetes related variant protein coding sequence is a heterologous.

"Expression vector"—refers to vectors that have the ability to incorporate and express heterologous DNA fragments in a foreign cell. Many prokaryotic and eukaryotic expression vectors are known and/or commercially available. Selection of appropriate expression vectors is within the knowledge of those having skill in the art.

"Deletion"—is a change in either nucleotide or amino acid sequence in which one or more nucleotides or amino acid residues, respectively, are absent.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively. As regards amino acid sequences the substitution may be conservative or non-conservative.

"Antibody"—refers to IgG, IgM, IgD, IgA, and IgG antibody. The definition includes polyclonal antibodies or monoclonal antibodies. This term refers to whole antibodies or fragments of the antibodies comprising the antigen-binding domain of the anti-variant product antibodies, e.g. antibodies without the Fc portion, single chain antibodies, fragments consisting of essentially only the variable, antigen-binding domain of the antibody, etc.

"Treating a disease"—refers to administering a therapeutic substance effective to ameliorate symptoms associated with a disease, to lessen the severity or cure the disease, or to prevent the disease from occurring.

"Detection"—refers to a method of detection of a disease, disorder, pathological or normal condition. This term may refer to detection of a predisposition to a disease as well as for establishing the prognosis of the patient by determining the severity of the disease.

"Probe"—the obesity and/or diabetes variant nucleic acid sequence, or a sequence complementary therewith, when used to detect presence of other similar sequences in a sample or of sequences having some homology with this sequence. The detection is carried out by identification of hybridization complexes between the probe and the assayed sequence. The probe may be attached to a solid support or to a detectable label.

"Original obesity and/or diabetes related genes"—the amino acid or nucleic acid sequence from which the obesity and/or diabetes related variants of the invention have been varied as a result of alternative slicing. The original nucleic sequence is the sequence of the human obesity and/or diabetes related gene depicted as SEQ ID NO: 1 for human Adiponectin and the original amino acid sequence is the sequence encoded by it; SEQ ID NO: 5 for mouse Adiponectin and the original amino acid sequence is the sequence encoded by it; SEQ ID NO: 10 for Ghrelin and the original amino acid sequence is the sequence encoded by it; SEQ ID NO: 12 for human 11-beta-HSD and the original amino acid sequence is the sequence encoded by it; SEQ ID NO: 19 for mouse 11-beta-HSD and the original amino acid sequence is the sequence encoded by it.

SUMMARY OF THE INVENTION

The present invention relates to isolated nucleic acid molecules having a sequence selected from the group consisting of: SEQ ID NO: 2–4; 6–9; 11; 13–18; 20–21 and fragments thereof comprising at least 20 nucleotides. The present invention relates to isolated nucleic acid molecules comprising SEQ ID NO: 2–4; 6–9; 11; 13–18; 20–21 and isolated nucleic acid molecules comprising fragments of SEQ ID NO: 2–4; 6–9; 11; 13–18; 20–21 comprising at least 20 nucleotides.

The present invention relates to PCR primers which can amplify products using sequences of SEQ ID NO: 2–4; 6–9; 11; 13–18; 20–21 as templates.

The present invention relates to methods of screening, diagnosing and monitoring individuals for obesity and/or diabetes. The methods comprise detecting the presence, absence, or quantity of a transcription product that comprises a sequence selected from the group consisting of: SEQ ID NO: 2–4; 6–9; 11; 13–18; 20–21 in a sample. The presence or quantity of said transcription product is indicative of obesity and/or diabetes.

The present invention relates to methods of screening, diagnosing and monitoring individuals for obesity and/or diabetes comprising the step of detecting the presence, absence, or quantity of a translation product of a transcript having a sequence selected from the group consisting of: SEQ ID NO: 2–4; 6–9; 11; 13–18; 20–21 in a sample. The presence or quantity of said translation product is indicative of obesity and/or diabetes The present invention relates to kits for screening, diagnosing and monitoring an individual for obesity and/or diabetes.

The present invention relates to proteins encoded by a nucleic acid sequence selected from the group consisting of: SEQ ID NO: 2–4; 6–9; 11; 13–18; 20–21 and immunogenic fragments thereof.

The present invention relates to antibodies which specifically bind to an epitope on a protein encoded by a nucleic acid sequence selected from the group consisting of: SEQ ID NO: 2–4; 6–9; 11; 13–18; 20–21.

The present invention relates to antibodies which specifically bind to an epitope on a protein encoded by a nucleic acid sequence selected from the group consisting of: SEQ ID NO: 2–4; 6–9; 11; 13–18; 20–21 that are linked to detectable labels or active agents.

The present invention relates to pharmaceutical composition comprising antibodies which specifically bind to an epitope on a protein encoded by a nucleic acid sequence selected from the group consisting of: SEQ ID NO: 2–4; 6–9; 11; 13–18; 20-21 that are linked to active agents.

The present invention relates to methods of treating an individual suspected of suffering from obesity and/or diabetes. The methods comprise the step of administering to individuals antibodies which specifically bind to an epitope on a protein encoded by a nucleic acid sequence selected from the group consisting of: SEQ ID NO: 2–4; 6–9; 11; 13–18; 20–21 that are linked to active agents.

The present invention relates to methods of delivering a nucleic acid molecule to obesity and/or diabetic cell of an individual. The methods comprise the step of administering to said individual a pharmaceutical composition comprising antibodies which specifically bind to an epitope on a protein encoded by a nucleic acid sequence selected from the group consisting of SEQ ID NO: 2–4; 6–9; 11; 13-18; 20–21 and, a nucleic acid molecules.

BRIEF DESCRIPTION OF THE DRAWING

FIG. 1 shows multiple alignment of four amino acid sequences ID NOS: 22–25 of human origin (depicted in SEQ ID NO:22 to SEQ ID NO:25 to each other and to the original sequence;

FIG. 2 shows multiple alignment of five amino acid sequences ID NOS: 26–30 of mouse origin (depicted in SEQ ID NO:26 to SEQ ID NO:30 to each other and to the original sequence;

FIG. 3 shows alignment of two amino acid sequences ID NOS: 31–32 of human origin (depicted in SEQ ID NO:31 to SEQ ID NO:32 to the original sequence;

FIG. 4 shows multiple alignment of seven amino acid sequences ID NOS: 33–39 of human origin (depicted in SEQ ID NO:33 to SEQ ID NO:39 to each other and to the original sequence;

FIG. 5 shows multiple alignment of three amino acid sequences ID NOS: 40–42 of human origin (depicted in SEQ ID NO:40 to SEQ ID NO:42 to each other and to the original sequence;

FIG. 6 shows multiple alignment of four nucleic acid sequences ID NOS: 1–4 of human origin (depicted in SEQ ID NO:1 to SEQ ID NO:4 to each other and to the original sequence;

FIG. 7 shows multiple alignment of five nucleic acid sequences ID NOS: 5–9 of mouse origin (depicted in SEQ ID NO:5 to SEQ ID NO:9 to each other and to the original sequence;

FIG. 8 shows alignment of two nucleic acid sequences ID NOS: 10–11 of human origin (depicted in SEQ ID NO:10 to SEQ ID NO:11 to the original sequence;

FIG. 9 shows multiple alignment of seven nucleic acid sequences ID NOS: 12–18 of human origin (depicted in SEQ ID NO:12 to SEQ ID NO:18 to each other and to the original sequence;

FIG. 10 shows multiple alignment of three amino acid sequences ID NOS: 19–21 of human origin (depicted in SEQ ID NO:19 to SEQ ID NO:21 to each other and to the original sequence;

DETAILED DESCRIPTION OF PREFERRED EMBODIMENTS

EXAMPLE I

Obesity and/or Diabetes Variants Nucleic Acid Sequence

The nucleic acid sequences of the invention include nucleic acid sequences which encode Obesity and/or diabetes variants products and fragments and analogs thereof. The nucleic acid sequences may alternatively be sequences complementary to the above coding sequences, or to regions of said coding sequence. The length of the complementary sequences is sufficient to avoid the expression of the coding sequence. The nucleic acid sequences may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand. The nucleic acid sequences may also both include dNTPs, rNTPs as well as non naturally occurring sequences. The sequence may also be a part of a hybrid between an amino acid sequence and a nucleic acid sequence.

In a general embodiment, the nucleic acid sequence has at least 90%, identity with any one of the sequence identified as SEQ ID NO:2 to SEQ ID NO:4 or SEQ ID NO:6 to SEQ ID NO:9 or SEQ ID NO:11 or SEQ ID NO:13 to SEQ ID:18 or SEQ ID NO:20 to SEQ ID 21.

The nucleic acid sequences may include the coding sequence by itself. By another alternative the coding region may be in combination with additional coding sequences, such as those coding for fusion protein or signal peptides, in combination with non-coding sequences, such as introns and control elements, promoter and terminator elements or 5' and/or 3' untranslated regions, effective for expression of the coding sequence in a suitable host, and/or in a vector or host environment in which the variant nucleic acid sequences is introduced as a heterologous sequence.

The nucleic acid sequences of the present invention may also have the Obesity and/or diabetes variants products coding sequences fused in-frame to a marker sequence which allows for purification of the variant product. The marker sequence may be, for example, a hexahistidine tag to provide for purification of the mature polypeptide fused to the marker in the case of a bacterial host, or, the marker sequence may be a hemagglutinin (HA) tag when a mammalian host, e.g. COS-7 cells, is used. The HA tag corresponds to an epitope derived from the influenza hemagglutinin protein (Wilson, I., et al. Cell37:767 (1984)).

Also included in the scope of the invention are fragments as defined above also referred to herein as oligonucleotides, typically having at least 20 bases, preferably 20–30 bases corresponding to a region of the coding-sequence nucleic acid sequence. The fragments may be used as probes, primers, and when complementary also as antisense agents, and the like, according to known methods.

As indicated above, the nucleic acid sequence may be substantially a depicted in SEQ ID NO:2 to SEQ ID NO:4 or SEQ ID NO:6 to SEQ ID NO:9 or SEQ ID NO:11 or SEQ ID NO:13 to SEQ ID:18 or SEQ ID NO:20 to SEQ ID 21 or fragments thereof or sequences having at least 90% identity to the above sequence as explained above. Alternatively, due to the degenerative nature of the genetic code, the sequence may be a sequence coding for any one of the amino acid sequence of SEQ ID NO:23 to SEQ ID NO:25 or SEQ ID NO:27 to SEQ ID NO:30 or SEQ ID NO:32 or SEQ ID NO:34 to SEQ ID:39 or SEQ ID NO:41 to SEQ ID 42, or fragments or analogs of said amino acid sequence.

A. Preparation of Nucleic Acid Sequences

The nucleic acid sequences may be obtained by screening cDNA libraries using oligonucleotide probes which can hybridize to or PCR-amplify nucleic acid sequences which encode the Obesity and/or diabetes variants products disclosed above. cDNA libraries prepared from a variety of tissues are commercially available and procedures for screening and isolating cDNA clones are well-known to those of skill in the art. Such techniques are described in, for example, Sambrook et al. (1989) Molecular Cloning: A Laboratory Manual (2nd Edition), Cold Spring Harbor Press, Plainview, N.Y. and Ausubel FM et al. (1989) Current Protocols in Molecular Biology, John Wiley & Sons, New York, N.Y.

The nucleic acid sequences may be extended to obtain upstream and downstream sequences such as promoters, regulatory elements, and 5' and 3' untranslated regions (UTRs). Extension of the available transcript sequence may be performed by numerous methods known to those of skill in the art, such as PCR or primer extension (Sambrook et al., supra), or by the RACE method using, for example, the Marathon RACE kit (Clontech, Cat. # K1802-1).

Alternatively, the technique of "restriction-site" PCR (Gobinda et al. *PCR Methods Applic*. 2:318–22, (1993)), which uses universal primers to retrieve flanking sequence adjacent a known locus, may be employed. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia, T. et al., *Nucleic Acids Res*. 16:8186, (1988)). The primers may be designed using OLIGO(R) 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Capture PCR (Lagerstrom, M. et al., *PCR Methods Applic*. 1:111–19, (1991)) is a method for PCR amplification of DNA fragments adjacent to a known sequence in human and yeast artificial chromosome DNA. Capture PCR also requires multiple restriction enzyme digestions and ligations to place an engineered double-stranded sequence into a flanking part of the DNA molecule before PCR.

Another method which may be used to retrieve flanking sequences is that of Parker, J. D., et al., *Nucleic Acids Res.*, 19:3055–60, (1991)). Additionally, one can use PCR, nested primers and PromoterFinder™ libraries to "walk in" genomic DNA (PromoterFinder™; Clontech, Palo Alto, Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes.

A randomly primed library may be particularly useful if an oligo d(T) library does not yield a full-length cDNA. Genomic libraries are useful for extension into the 5' non-translated regulatory region.

The nucleic acid sequences and oligonucleotides of the invention can also be prepared by solid-phase methods, according to known synthetic methods. Typically, fragments of up to about 100 bases are individually synthesized, then joined to form continuous sequences up to several hundred bases.

B. Use of Obesity and/or Diabetes Variants Nucleic Acid Sequences for the Production of Obesity and/or Diabetes Variants Products In accordance with the present invention, nucleic acid sequences specified above may be used as recombinant DNA molecules that direct the expression of Obesity and/or diabetes variant products.

As will be understood by those of skill in the art, it may be advantageous to produce Obesity and/or diabetes variants product-encoding nucleotide sequences possessing codons other than those which appear in SEQ ID NO:2 to SEQ ID NO:4 or SEQ ID NO:6 to SEQ ID NO:9 or SEQ ID NO:11 or SEQ ID NO:13 to SEQ ID:18 or SEQ ID NO:20 to SEQ ID 21 which are those which naturally occur in the human genome. Codons preferred by a particular prokaryotic or eukaryotic host (Murray, E. et al *Nuc Acids Res.*, 17:477–508, (1989)) can be selected, for example, to increase the rate of variant product expression or to produce recombinant RNA transcripts having desirable properties, such as a longer half-life, than transcripts produced from naturally occurring sequence.

The nucleic acid sequences of the present invention can be engineered in order to alter a Obesity and/or diabetes variants products coding sequences for a variety of reasons, including but not limited to, alterations which modify the cloning, processing and/or expression of the product. For example, alterations may be introduced using techniques which are well known in the art, e.g., site-directed mutagenesis, to insert new restriction sites, to alter glycosylation patterns, to change codon preference, etc.

The present invention also includes recombinant constructs comprising one or more of the sequences as broadly described above. The constructs comprise a vector, such as a plasmid or viral vector, into which nucleic acid sequences of the invention have been inserted, in a forward or reverse orientation. In a preferred aspect of this embodiment, the constructs further comprise regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook, et al., (supra).

The present invention also relates to host cells which are genetically engineered with vectors of the invention, and the production of the product of the invention by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the expression of the variant nucleic acid sequence. The culture conditions, such as temperature, pH and the like, are those previously used with the host cell selected for expression, and will be apparent to those skilled in the art.

The nucleic acid sequences of the present invention may be included in any one of a variety of expression vectors for expressing a product. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The DNA sequence in the expression vector is operatively linked to an appropriate transcription control sequence (promoter) to direct mRNA synthesis. Examples of such promoters include: LTR or SV40 promoter, the *E. coli* lac or trp promoter, the phage lambda PL promoter, and other promoters known to control expression of genes in prokaryotic or eukaryotic cells or their viruses. The expression vectors also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vectors containing the appropriate DNA sequence as described above, as well as an appropriate promoter or control sequence, may be employed to transform an appropriate host to permit the host to express the protein. Examples of appropriate expression hosts include: bacterial cells, such as *E. coli, Streptomyces, Salmonella typhimurium*; fungal cells, such as yeast; insect cells such as *Drosophila* and *Spodoptera* Sf9; animal cells such as CHO, COS, HEK 293 or Bowes melanoma; adenoviruses; plant cells, etc. The selection of an appropriate host is deemed to be within the scope of those skilled in the art from the teachings herein. The invention is not limited by the host cells employed.

In bacterial systems, a number of expression vectors may be selected depending upon the use intended for the Obesity and/or diabetes variant product. For example, when large quantities of Obesity and/or diabetes variant product are needed for the induction of antibodies, vectors which direct high level expression of fusion proteins that are readily purified may be desirable. Such vectors include, but are not limited to, multifunctional *E. coli* cloning and expression vectors such as Bluescript(R) (Stratagene), in which the Obesity and/or diabetes variants polypeptides coding sequence may be ligated into the vector in-frame with sequences for the amino-terminal Met and the subsequent 7 residues of beta-galactosidase so that a hybrid protein is produced; pIN vectors (Van Heeke & Schuster *J. Biol. Chem.* 264:5503–5509, (1989)); pET vectors (Novagen, Madison Wis.); and the like.

In the yeast *Saccharomyces cerevisiae* a number of vectors containing constitutive or inducible promoters such as alpha factor, alcohol oxidase and PGH may be used. For reviews, see Ausubel et al. (supra) and Grant et al., (*Methods in Enzymology* 153:516–544, (1987)).

In cases where plant expression vectors are used, the expression of a sequence encoding variant products may be driven by any of a number of promoters. For example, viral promoters such as the 35S and 19S promoters of CaMV (Brisson et al., *Nature* 310:511–514. (1984)) may be used alone or in combination with the omega leader sequence from TMV (Takamatsu et al., *EMBO J.*, 6:307–311, (1987)). Alternatively, plant promoters such as the small subunit of RUBISCO (Coruzzi et al., *EMBO J.* 3:1671–1680, (1984); Broglie et al., *Science* 224:838–843, (1984)); or heat shock promoters (Winter J and Sinibaldi R. M., *Results Probl. Cell Differ.*, 17:85–105, (1991)) may be used. These constructs can be introduced into plant cells by direct DNA transformation or pathogen-mediated transfection. For reviews of such techniques, see Hobbs S. or Murry L. E. (1992) in McGraw Hill Yearbook of Science and Technology, McGraw Hill, New York, N.Y., pp 191–196; or Weissbach and Weissbach (1988) *Methods for Plant Molecular Biology*, Academic Press, New York, N.Y., pp 421–463.

Obesity and/or diabetes variants products may also be expressed in an insect system. In one such system, Autographa californica nuclear polyhedrosis virus (AcNPV) is used as a vector to express foreign genes in *Spodoptera frugiperda* cells or in *Trichoplusia* larvae. The Obesity and/or diabetes variants products coding sequence may be cloned into a nonessential region of the virus, such as the polyhedrin gene, and placed under control of the polyhedrin promoter. Successful insertion of Obesity and/or diabetes coding sequences will render the polyhedrin gene inactive and produce recombinant virus lacking coat protein coat. The recombinant viruses are then used to infect *S. frugiperda* cells or *Trichoplusia* larvae in which variant protein is expressed (Smith et al., *J. Virol.* 46:584, (1983); Engelhard, E. K. et al., *Proc. Nat. Acad. Sci.* 91:3224–7, (1994)).

In mammalian host cells, a number of viral-based expression systems may be utilized. In cases where an adenovirus is used as an expression vector, Obesity and/or diabetes variants products coding sequences may be ligated into an adenovirus transcription/translation complex consisting of the late promoter and tripartite leader sequence. Insertion in a nonessential E1 or E3 region of the viral genome will result in a viable virus capable of expressing variant protein in infected host cells (Logan and Shenk, *Proc. Natl. Acad. Sci.* 81:3655–59, (1984). In addition, transcription enhancers, such as the Rous sarcoma virus (RSV) enhancer, may be used to increase expression in mammalian host cells.

Specific initiation signals may also be required for efficient translation of variants products coding sequences. These signals include the ATG initiation codon and adjacent sequences. In cases where Obesity and/or diabetes variants products coding sequence, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf, D. et al., (1994) *Results Probl. Cell Differ.*, 20:125–62, (1994); Bittner et al., *Methods in Enzymol* 153:516–544, (1987)).

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, I. (1986) Basic Methods in Molecular Biology). Cell-free translation systems can also be employed to produce polypeptides using RNAs derived from the DNA constructs of the present invention.

A host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre-pro" form of the protein may also be important for correct insertion, folding and/or function. Different host cells such as CHO, HeLa, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express variant products may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M., et al., *Cell* 11:223–32, (1977)) and adenine phosphoribosyltransferase (Lowy I., et al., *Cell* 22:817–23, (1980)) genes which can be employed in tk- or aprt-cells, respectively. Also, antimetabolite, antibiotic or herbicide resistance can be used as the basis for selection; for example, dhfr which confers resistance to methotrexate (Wigler M., et al., *Proc. Natl. Acad. Sci.* 77:3567–70, (1980)); npt, which confers resistance to the aminoglycosides neomycin and G-418 (Colbere-Garapin, F. et al., *J. Mol. Biol.*, 150:1–14, (1981)) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan, *Proc. Natl. Acad. Sci.* 85:8047–51, (1988)). The use of visible markers has gained popularity with such markers as anthocyanins, beta-glucuronidase and its substrate, GUS, and luciferase and its substrates, luciferin and ATP, being widely used not only to identify transformants, but also to quantify the amount of transient or stable protein expression attributable to a specific vector system (Rhodes, C. A. et. al., *Methods Mol. Biol.*, 55:121–131, (1995)).

Host cells transformed with nucleotide sequences encoding Obesity and/or diabetes variants products may be cultured under conditions suitable for the expression and recovery of the encoded protein from cell culture. The product produced by a recombinant cell may be secreted or contained intracellularly depending on the sequence and/or the vector used. As will be understood by those of skill in the art, expression vectors containing nucleic acid sequences encoding Obesity and/or diabetes variants products can be designed with signal sequences which direct secretion of Obesity and/or diabetes variants products through a prokaryotic or eukaryotic cell membrane.

The Obesity and/or diabetes variants products may also be expressed as recombinant proteins with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a protease-cleavable polypeptide linker sequence between the purification domain and Obesity and/or diabetes variants products is useful to facilitate purification. One such expression vector provides for expression of a fusion protein compromising a variant polypeptide fused to a polyhistidine region separated by an enterokinase cleavage site. The histidine residues facilitate purification on IMIAC (immobilized metal ion affinity chromatography, as described in Porath, et al., *Protein Expression and Purification*, 3:263–281, (1992)) while the enterokinase cleavage site provides a means for isolating variant polypeptide from the fusion protein. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

The Obesity and/or diabetes variants products can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Protein refolding steps can be used, as necessary, in completing configuration of the mature protein. Finally, high performance liquid chromatography (HPLC) can be employed for final purification steps.

Sf-9 cells were infected with Obesity and/or diabetes variants expressing baculovirus (Ac-obesity and/or diabetes variant) comprising the amino acid sequence of SEQ ID NO:23 to SEQ ID NO:25 or SEQ ID NO:27 to SEQ ID NO:30 or SEQ ID NO:32 or SEQ ID NO:34 to SEQ ID:39 or SEQ ID NO:41 to SEQ ID 42 at MOI of 2. The cells were grown in 28° C. at continuous shaking (90 rpm). At 60 hours post infection (hpi) the medium was collected and cells were separated from the medium by centrifugation at 5000 RPM for 5 minutes. 10 ml medium was separated using cation exchange chromatography with SP-Sepharose column. The Column was equilibrated with PBS pH-6.5 and following loading of the sample on the column the column was washed with PBS to elute the unbound proteins (flow through fraction). Elution was done with increasing concentration of NaCl at flow rate of 2 ml/min (5% NaCl/min).

The different fractions were subjected to SDS-PAGE electrophoresis and to western blotting using anti m Obesity and/or diabetes variant antibody.

C.1 Secretion:

Sf-9 cells were infected with Obesity and/or diabetes variants expressing baculovirus (Ac-obesity and/or diabetes variant) at MOI of 2. The cells were grown at 28° C. at continuous shaking (90 rpm) and 1 ml samples were collected at 24, 48 and 60 hours post infection (hpi). Following centrifugation Cells pellet was lysed with lysis buffer (50 mM Tris pH 7.5, 1% triton X100, and protease inhibitor cocktail) at 4° C. for 30 min and sonicated for 30 seconds. The sample was centrifuged for 10 minutes at 14000 rmp and the sup was designated Pellet. 40 μl of the pellet preparation and of the medium (Designated Medium) were supplemented with sample buffer and electrophoreses on a 15% SDS-PAGE. Following electrophoresis the gel was subjected to a semi dry protein transfer onto a nitrocellulose membrane. The membrane was incubated with anti m Obesity and/or diabetes variants antibody for 2 hours and with secondary anti rabbit antibody for an additional 1 hour.

Detection of the signal was done using a commercial western blot detection kit.

D. Diagnostic Applications Utilizing Nucleic Acid Sequences

The nucleic acid sequences of the present invention may be used for a variety of diagnostic purposes. The nucleic acid sequences may be used to detect and quantitate expression of the Obesity and/or diabetes variant in patient's cells, e.g. biopsied tissues, by detecting the presence of mRNA coding for the Obesity and/or diabetes variants products. Alternatively, the assay may be used to detect the soluble variants in the serum or blood. This assay typically involves obtaining total mRNA from the tissue or serum and contacting the mRNA with a nucleic acid probe. The probe is a nucleic acid molecule of at least 20 nucleotides, preferably 20–30 nucleotides, capable of specifically hybridizing with a sequence included within the sequence of a nucleic acid molecule encoding the Obesity and/or diabetes variant product under hybridizing conditions, detecting the presence of mRNA hybridized to the probe, and thereby detecting the expression of variant. This assay can be used to distinguish between absence, presence, and excess expression of Obesity and/or diabetes variants products and to monitor levels of Obesity and/or diabetes variants expression during therapeutic intervention. In addition, the assay may be used to compare the levels of the Obesity and/or diabetes variant of the invention to the levels of the original Obesity and/or diabetes sequence from which it has been varied or to levels of each other, which comparison may have some physiological meaning.

The invention also contemplates the use of the nucleic acid sequences as a diagnostic for diseases resulting from inherited defective variants sequences, or diseases in which the ratio of the amount of the original Obesity and/or diabetes sequence from which the Obesity and/or diabetes variants were varied to the novel Obesity and/or diabetes variants of the invention is altered. These sequences can be detected by comparing the sequences of the defective (i.e., mutant) Obesity and/or diabetes variants coding region with that of a normal coding region. Association of the sequence coding for mutant Obesity and/or diabetes variants products with abnormal variants products activity may be verified. In addition, sequences encoding mutant Obesity and/or diabetes variants products can be inserted into a suitable vector for expression in a functional assay system (e.g., colorimetric assay, complementation experiments in a variant protein deficient strain of HEK293 cells) as yet another means to verify or identify mutations. Once mutant genes have been identified, one can then screen populations of interest for carriers of the mutant gene.

Individuals carrying mutations in the nucleic acid sequences of the present invention may be detected at the DNA level by a variety of techniques. Nucleic acids used for diagnosis may be obtained from a patient's cells, including but not limited to such as from blood, urine, saliva, placenta, tissue biopsy and autopsy material. Genomic DNA may be used directly for detection or may be amplified enzymatically by using PCR (Saiki, et al., *Nature* 324:163–166, (1986)) prior to analysis. RNA or cDNA may also be used for the same purpose. As an example, PCR primers complementary to the nucleic acid of the present invention can be used to identify and analyze mutations in the gene of the present invention. Deletions and insertions can be detected by a change in size of the amplified product in comparison to the normal genotype.

Point mutations can be identified by hybridizing amplified DNA to radiolabeled RNA of the invention or alternatively, radiolabeled antisense DNA sequences of the invention. Sequence changes at specific locations may also be revealed by nuclease protection assays, such RNase and SI protection or the chemical cleavage method (e.g. Cotton, et al *Proc. Natl. Acad. Sci.* USA, 85:4397–4401, (1985)), or by differences in melting temperatures. "*Molecular beacons*" (Kostrikis L.G. et al., Science 279:1228–1229, (1998)), hairpin-shaped, single-stranded synthetic oligo-nucleotides containing probe sequences which are complementary to the nucleic acid of the present invention, may also be used to detect point mutations or other sequence changes as well as monitor expression levels of variant product. Such diagnostics would be particularly useful for prenatal testing.

Another method for detecting mutations uses two DNA probes which are designed to hybridize to adjacent regions of a target, with abutting bases, where the region of known or suspected mutation(s) is at or near the abutting bases. The two probes may be joined at the abutting bases, e.g., in the presence of a ligase enzyme, but only if both probes are correctly base paired in the region of probe junction. The presence or absence of mutations is then detectable by the presence or absence of ligated probe.

Also suitable for detecting mutations in the Obesity and/or diabetes variants products coding sequences are oligonucleotide array methods based on sequencing by hybridization (SBH), as described, for example, in U.S. Pat. No. 5,547,839. In a typical method, the DNA target analyte is hybridized with an array of oligonucleotides formed on a microchip. The sequence of the target can then be "read" from the pattern of target binding to the array.

E. Therapeutic Applications of Nucleic Acid Sequences

Nucleic acid sequences of the invention may also be used for therapeutic purposes. Turning first to the second aspect of the invention (i.e. inhibition of expression of Obesity and/or diabetes variants), expression of Obesity and/or diabetes variants products may be modulated through antisense technology, which controls gene expression through hybridization of complementary nucleic acid sequences, i.e. antisense DNA or RNA, to the control, 5' or regulatory regions of the gene encoding variant product. For example, the 5' coding portion of the nucleic acid sequence sequence which codes for the product of the present invention is used to design an antisense oligonucleotide of from about 10 to 40 base pairs in length. Oligonucleotides derived from the transcription start site, e.g. between positions −10 and +10 from the start site, are preferred. An antisense DNA oligonucleotide is designed to be complementary to a region of the nucleic acid sequence involved in transcription (Lee et al., *Nucl. Acids, Res.*, 6:3073, (1979); Cooney et al., Science 241:456, (1988); and Dervan et al., *Science*251:1360, (1991)), thereby preventing transcription and the production of the variant products. An antisense RNA oligonucleotide hybridizes to the mRNA in vivo and blocks translation of the mRNA molecule into the variant products (Okano *J. Neurochem.* 56:560, (1991)). The antisense constructs can be delivered to cells by procedures known in the art such that the antisense RNA or DNA may be expressed in vivo. The antisense may be antisense mRNA or DNA sequence capable of coding such antisense mRNA. The antisense mRNA or the DNA coding thereof can be complementary to the full sequence of nucleic acid sequences coding for the Obesity and/or diabetes variant protein or to a fragment of such a sequence which is sufficient to inhibit production of a protein product. Antisense technologies can also be used for inhibiting expression of one variant as compared to the other, or inhibiting the expression of the variant/s as compared to the original sequence.

Turning now to the first aspect of the invention, i.e. expression of Obesity and/or diabetes variants, expression of Obesity and/or diabetes variants products may be increased by providing coding sequences for coding for said Obesity and/or diabetes variants products under the control of suitable control elements ending its expression in the desired host.

The nucleic acid sequences of the invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The products of the invention may also be employed in accordance with the present invention by expression of such polypeptides in vivo, which is often referred to as "*gene therapy*." Cells from a patient may be engineered with a nucleic acid sequence (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by procedures known in the art. As known in the art, a producer cell for producing a retroviral particle containing RNA encoding the polypeptides of the present invention may be administered to a patient for engineering cells in vivo and expression of the polypeptide in vivo. These and other methods for administering products of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors mentioned above may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, psi-2, psi-AM, PA12, T19-14X, VT-19-17-H2, psi-CRE, psi-CRIP, GP+E-86, GP+envAm12, and DAN cell lines as described in Miller (*Human Gene Therapy*, Vol. 1, pg. 5–14, (1990)). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The genes introduced into cells may be placed under the control of inducible promoters, such as the radiation-inducible Egr-1 promoter, (Maceri, H. J., et al., *Cancer Res.*, 56(19):4311 (1996)), to stimulate variant production or antisense inhibition in response to radiation, eg., radiation therapy for treating tumors.

EXAMPLE II

Obesity and/or Diabetes Variants Products

The substantially purified Obesity and/or diabetes variant product of the invention has been defined above as the product coded from the nucleic acid sequence of the invention. Preferably the amino acid sequence is an amino acid sequence having at least 90% identity the sequence identified as SEQ ID NO:23 to SEQ ID NO:25 or SEQ ID NO:27 to SEQ ID NO:30 or SEQ ID NO:32 or SEQ ID NO:34 to SEQ ID:39 or SEQ ID NO:41 to SEQ ID 42. The protein or polypeptide may be in mature and/or modified form, also as defined above, for example, modified by cleavage of the leader sequence. Also contemplated are protein fragments having at least 10 contiguous amino acid residues, preferably at least 10–20 residues, derived from the Obesity and/or diabetes variant products, as well as homologues as explained above.

The sequence variations are preferably those that are considered conserved substitutions, as defined above. Thus, for example, a protein with a sequence having at least 90% sequence identity with the products identified as SEQ ID NO:23 to SEQ ID NO:25 or SEQ ID NO:27 to SEQ ID NO:30 or SEQ ID NO:32 or SEQ ID NO:34 to SEQ ID:39 or SEQ ID NO:41 to SEQ ID 42, preferably by utilizing conserved substitutions as defined above is also part of the invention, and provided that it is not identical to the original peptide from which it has been varied (typically the substitutions are in regions where the variant differs from the original sequence as for example in Table 1). In a more specific embodiment, the protein has or contains the sequence identified SEQ ID NO:23 to SEQ ID NO:25 or SEQ ID NO:27 to SEQ ID NO:30 or SEQ ID NO:32 or SEQ ID NO:34 to SEQ ID:39 or SEQ ID NO:41 to SEQ ID 42. The Obesity and/or diabetes variants products may be (i) one in which one or more of the amino acid residues in a sequence listed above are substituted with a conserved or non-conserved amino acid residue (preferably a conserved amino acid residue), or (ii) one in which one or more of the amino acid residues includes a substituent group, or (iii) one in which the Obesity and/or diabetes variants products is fused with another compound, such as a compound to increase the half-life of the protein (for example, polyethylene glycol (PEG)), or a moiety which serves as targeting means to direct the protein to its target tissue or target cell population (such as an antibody), or (iv) one in which additional amino acids are fused to the Obesity and/or diabetes variant product. Such fragments, variants and derivatives are deemed to be within the scope of those skilled in the art from the teachings herein.

A. Preparation of Obesity and/or Diabetes Variants Products

Recombinant methods for producing and isolating the Obesity and/or diabetes variant products, and fragments of the protein are described above.

In addition to recombinant production, fragments and portions of variant products may be produced by direct peptide synthesis using solid-phase techniques (cf. Stewart et al., (1969) Solid-Phase Peptide Synthesis, WH Freeman Co, San Francisco; Merrifield J., *J. Am. Chem. Soc.*, 85:2149–2154, (1963)). In vitro peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Fragments of Obesity and/or diabetes variants products may be chemically synthesized separately and combined using chemical methods to produce the full length molecule.

2nd. Therapeutic Uses and Compositions Utilizing the Obesity and/or Diabetes Variants Products The Obesity and/or diabetes variants products of the invention are generally useful in treating obesity and/or diabetes.

Obesity and/or diabetes variant products or fragments may be administered by any of a number of routes and methods designed to provide a consistent and predictable concentration of compound at the target organ or tissue. The product-containing compositions may be administered alone or in combination with other agents, such as stabilizing compounds, and/or in combination with other pharmaceutical agents such as drugs or hormones.

Obesity and/or diabetes variants product-containing compositions may be administered by a number of routes including, but not limited to oral, intravenous, intramuscular, transdermal, subcutaneous, topical, sublingual, or rectal means as well as by nasal application. Obesity and/or diabetes variant product-containing compositions may also be administered via liposomes. Such administration routes and appropriate formulations are generally known to those of skill in the art.

The Obesity and/or diabetes variants products can be given via intravenous or intraperitoneal injection. Similarly, the product may be injected to other localized regions of the body. The product may also be administered via nasal insufflation. Enteral administration is also possible. For such administration, the product should be formulated into an appropriate capsule or elixir for oral administration, or into a suppository for rectal administration.

The foregoing exemplary administration modes will likely require that the product be formulated into an appropriate carrier, including ointments, gels, suppositories. Appropriate formulations are well known to persons skilled in the art.

Dosage of the product will vary, depending upon the potency and therapeutic index of the particular polypeptide selected.

A therapeutic composition for use in the treatment method can include the product in a sterile injectable solution, the polypeptide in an oral delivery vehicle, the product in an aerosol suitable for nasal administration, or the product in a nebulized form, all prepared according to well known methods. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The product of the invention may also be used to modulate endothelial differentiation and proliferation as well as to modulate apoptosis either ex vivo or in vitro, for example, in cell cultures.

EXAMPLE III

Anti-Variant Antibodies

A. Synthesis

In still another aspect of the invention, the purified variants products are used to produce anti-variant antibodies which have diagnostic and therapeutic uses related to the activity, distribution, and expression of the Obesity and/or diabetes variants products.

Antibodies to the Obesity and/or diabetes variant may be generated by methods well known in the art. Such antibodies may include, but are not limited to, polyclonal, monoclonal, chimeric, humanized, single chain, Fab fragments and fragments produced by an Fab expression library. Antibodies, i.e., those which inhibit dimer formation, are especially preferred for therapeutic use.

A fragment of the Obesity and/or diabetes variants products for antibody induction is not required to feature biological activity but has to feature immunological activity; however, the protein fragment or oligopeptide must be antigenic. Peptides used to induce specific antibodies may have an amino acid sequence consisting of at least five amino acids, preferably at least 10 amino acids of the sequences specified in SEQ ID NO:23 to SEQ ID NO:25 or SEQ ID NO:27 to SEQ ID NO:30 or SEQ ID NO:32 or SEQ ID NO:34 to SEQ ID:39 or SEQ ID NO:41 to SEQ ID 42. Preferably they should mimic a portion of the amino acid sequence of the natural protein and may contain the entire amino acid sequence of a small, naturally occurring molecule. Short stretches of Obesity and/or diabetes variants proteins amino acids may be fused with those of another protein such as keyhole limpet hemocyanin and antibody produced against the chimeric molecule. Procedures well known in the art can be used for the production of antibodies to Obesity and/or diabetes variants products.

For the production of antibodies, various hosts including goats, rabbits, rats, mice, etc may be immunized by injection with Obesity and/or diabetes variants products or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants.

Monoclonal antibodies to Obesity and/or diabetes variants protein may be prepared using any technique which provides for the production of antibody molecules by continuous cell lines in culture. These include but are not limited to the hybridoma technique originally described by Koehler and Milstein (*Nature* 256:495–497, (1975)), the human B-cell hybridoma technique (Kosbor et al., *Immunol. Today* 4:72, (1983); Cote et al., *Proc. Natl. Acad. Sci.* 80:2026–2030. (1983)) and the EBV-hybridoma technique (Cole, et al., *Mol. Cell Biol*. 62:109–120, (1984)).

Techniques developed for the production of "chimeric antibodies", the splicing of mouse antibody genes to human antibody genes to obtain a molecule with appropriate antigen specificity and biological activity can also be used (Morrison et al., *Proc. Natl. Acad. Sci.* 81:6851–6855, (1984); Neuberger et al., *Nature* 312:604–608, (1984); Takeda et al., *Nature* 314:452–454, (1985)). Alternatively, techniques described for the production of single chain antibodies (U.S. Pat. No. 4,946,778) can be adapted to produce single-chain antibodies specific for the variant protein.

Antibodies may also be produced by inducing in vivo production in the lymphocyte population or by screening recombinant immunoglobulin libraries or panels of highly specific binding reagents as disclosed in Orlandi et al. (*Proc. Natl. Acad. Sci.* 86:3833–3837, 1989)), and Winter G and Milstein C., (*Nature* 349:293–299, (1991)).

Antibody fragments which contain specific binding sites for the Obesity and/or diabetes variant protein may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W.D. et al., *Science* 256:1275–1281, (1989)).

B. Diagnostic Applications of Antibodies

A variety of protocols for competitive binding or immunoradiometric assays using either polyclonal or monoclonal antibodies with established specificities are well known in the art. Such immunoassays typically involve the formation of complexes between the Obesity and/or diabetes variants products and its specific antibody and the measurement of complex formation. A two-site, monoclonal-based immunoassay utilizing monoclonal antibodies reactive to two noninterfering epitopes on a specific variant product is preferred, but a competitive binding assay may also be employed. These assays are described in Maddox D. E., et al., (*J. Exp. Med.* 158:1211, (1983)).

Antibodies which specifically bind the Obesity and/or diabetes variant product are useful for the diagnosis of conditions or diseases characterized by expression of the novel Obesity and/or diabetes variants of the invention (where normally it is not expressed) by over or under expression of Obesity and/or diabetes variants as well as for detection of diseases in which the proportion between the amount of the Obesity and/or diabetes variants of the invention and the original Obesity and/or diabetes sequence from which it varied is altered. Alternatively, such antibodies may be used in assays to monitor patients being treated with Obesity and/or diabetes variants products. Diagnostic assays for variants proteins include methods utilizing the antibody and a label to detect variants products in human body fluids or extracts of cells or tissues. The products and antibodies of the present invention may be used with or without modification. Frequently, the proteins and antibodies will be labeled by joining them, either covalently or noncovalently, with a reporter molecule. A wide variety of reporter molecules are known in the art.

A variety of protocols for measuring the Obesity and/or diabetes variants products, using either polyclonal or monoclonal antibodies specific for the respective protein are known in the art. Examples include enzyme-linked immunosorbent assay (ELISA), radioimmunoassay (RIA), and fluorescent activated cell sorting (FACS). As noted. above, a two-site, monoclonal-based immunoassay utilizing monoclonal antibodies reactive to two non-interfering epitopes on Obesity and/or diabetes variants products is preferred, but a competitive binding assay may be employed. These assays are described, among other places, in Maddox, et al. (supra). Such protocols provide a basis for diagnosing altered or abnormal levels of Obesity and/or diabetes variants products expression. Normal or standard values for Obesity and/or diabetes variants products expression are established by combining body fluids or cell extracts taken from normal subjects, preferably human, with antibodies to Obesity and/or diabetes variants products under conditions suitable for complex formation which are well known in the art. The amount of standard complex formation may be quantified by various methods, preferably by photometric methods. Then, standard values obtained from normal samples may be compared with values obtained from samples from subjects potentially affected by disease. Deviation between standard and subject values establishes the presence of disease state.

The antibody assays are useful to determine the level of Obesity and/or diabetes variants products present in a body fluid sample, in order to determine whether it is being expressed at all, whether it is being overexpressed or underexpressed in the tissue, or as an indication of how Obesity and/or diabetes variants levels of variable products are responding to drug treatment.

3rd. Therapeutic Uses of Antibodies

In addition to their diagnostic use the antibodies may have a therapeutical utility in blocking or decreasing the activity of the obesity and/or diabetes variants products in pathological conditions where beneficial effect can be achieved by such a decrease.

The antibody employed is preferably a humanized monoclonal antibody, or a human Mab produced by known globulin-gene library methods. The antibody is administered typically as a sterile solution by IV injection, although other parenteral routes may be suitable. Typically, the antibody is administered in an amount between about 1–15 mg/kg body weight of the subject. Treatment is continued, e.g., with dosing every 1–7 days, until a therapeutic improvement is seen.

Although the invention has been described with reference to specific methods and embodiments, it is appreciated that various modifications and changes may be made without departing from the invention.

EXAMPLE 1

Separation

Sf-9 cells are infected with Obesity and/or diabetes variants expressing baculovirus (AC-obesity and/or diabetes variant) comprising the amino acid sequence of SEQ ID NO:23 to SEQ ID NO:25 or SEQ ID NO:27 to SEQ ID NO:30 or SEQ ID NO:32 or SEQ ID NO:34 to SEQ ID NO:39 or SEQ ID NO:41 to SEQ ID NO:42 at MOI of 2. The cells are grown in 28° C. at continuous shaking (90 rpm). At 60 hours post-infection (hpi), the medium is collected and cells are separated from the medium by centrifugation at 5000 rpm for 5 minutes. 10 mL medium is separated using cation exchange chromatography with a SP-Sepharose column. The column is equilibrated with PBS pH 6.5, and, following loading of the sample on the column, the column is washed with PBS to elute the unbound proteins (flow through fraction). Elution is done with increasing concentration of NaCl at a flow rate of 2 mL/min (5% NaCl/min).

The different fractions are subjected to SDS-PAGE electrophoresis and to western blotting using anti-Obesity and/or diabetes variant antibody.

EXAMPLE 2

Secretion

Sf-9 cells are infected with Obesity and/or diabetes variants expressing baculovirus (Ac-obesity and/or diabetes variant) at MOI of 2. The cells are grown at 28° C. at continuous shaking (90 rpm), and 1 mL samples are collected at 24, 48, and 60 hours post-infection (hpi). Following centrifugation, cell pellets are lysed with lysis buffer (50 mM Tris pH 7.5, 1% triton X100, and protease inhibitor cocktail) at 4° C. for 30 mm and sonicated for 30 seconds. The sample is centrifuged for 10 minutes at 14000 rpm and the supernatant is designated Pellet. 40 µL of the Pellet preparation and of the medium (Designated Medium) are supplemented with sample buffer and are electrophoresed on a 15% SDS-PAGE. Following electrophoresis, the gel is subjected to a semi-dry protein transfer onto a nitrocellulose membrane. The membrane is incubated with anti-Obesity and/or diabetes variants antibody for 2 hours and with secondary anti-rabbit antibody for an additional 1 hour.

Detection of the signal is done using a commercial western blot detection kit.

The invention claimed is:

1. An isolated amino acid sequence coded by nucleotides 112 to 462 of SEQ ID NO:11.

2. The isolated amino acid sequence of claim 1, wherein said isolated amino acid sequence is SEQ ID NO:32.

* * * * *

SEQUENCE LISTING

<160> NUMBER OF SEQ ID NOS: 42

<210> SEQ ID NO 1
<211> LENGTH: 4517
<212> TYPE: DNA
<213> ORGANISM: Homo sapiens

<400> SEQUENCE: 1

```
ctgattccat accagagggg ctcaggatgc tgttgctggg agctgttcta ctgctattag      60
ctctgcccgg gcatgaccag gaaaccacga ctcaagggcc cggagtcctg cttcccctgc     120
ccaaggggc ctgcacaggt tggatggcgg gcatcccagg gcatccgggc cataatgggg      180
ccccaggccg tgatggcaga gatggcaccc ctggtgagaa gggtgagaaa ggagatccag     240
gtcttattgg tcctaaggga gacatcggtg aaaccggagt acccgggggct gaaggtcccc   300
gaggctttcc gggaatccaa ggcaggaaag gagaacctgg agaaggtgcc tatgtatacc     360
gctcagcatt cagtgtggga ttggagactt acgttactat ccccaacatg cccattcgct     420
ttaccaagat cttctacaat cagcaaaacc actatgatgg ctccactggt aaattccact     480
gcaacattcc tgggctgtac tactttgcct accacatcac agtctatatg aaggatgtga     540
aggtcagcct cttcaagaag gacaaggcta tgctcttcac ctatgatcag taccaggaaa     600
ataatgtgga ccaggcctcc ggctctgtgc tcctgcatct ggaggtgggc gaccaagtct     660
ggctccaggt gtatggggaa ggagagcgta atggactcta tgctgataat gacaatgact     720
ccaccttcac aggctttctt ctctaccatg acaccaactg atcaccacta actcagagcc     780
tcctccaggc caaacagccc caaagtcaat taaaggcttt cagtacggtt aggaagttga     840
ttattattta gttggaggcc tttagatatt attcattcat ttactcattc atttattcat     900
tcattcatca agtaacttta aaaaaatcat atgctatgtt cccagtcctg gggagcttca     960
caaacatgac cagataactg actagaaaga agtagttgac agtgctattt tgtgcccact    1020
gtctctcctg atgctcatat caatcctata aggcacaggg aacaagcatt ctcctgtttt    1080
tacagattgt atcctgaggc tgagagagtt aagtgaatgt ctaaggtcac acagtattaa    1140
gtgacagtgc tagaaatcaa acccagagct gtggactttg ttcactagac tgtgcccttt    1200
tatagaggta catgttctct ttggagtgtt ggtaggtgtc tgtttcccac ctcacctgag    1260
agccattgaa tttgccttcc tcatgaatta aaacctcccc caagcagagc ttcctcagag    1320
aaagtggttc tatgatgaag tcctgtcttg gaaggactac tactcaatgg cccctgcact    1380
actctacttc ctcttaccta tgtcccttct catgcctttc cctccaacgg ggaaagccaa    1440
ctccatctct aagtgctgaa ctcatccctg ttcctcaagg ccacctggcc aggagcttct    1500
ctgatgtgat atccactttt ttttttttt gagatggagt ctcactctgt cacccaggct    1560
ggagtacagt gacacgacct cggctcactg cagcctcctt ctcctgggtc caagcaatta    1620
ttgtgcctca gcctcccgag tagctgagac ttcaggtgca ttccaccaca catggctaat    1680
ttttgtattt ttagtagaaa tggggttttcg tcatgttggc caggctggtc tcgaactcct    1740
ggcctaggtg atccacccgc ctcgacctcc caaagtgctg ggattacagg catgagccac    1800
catgcccagt cgatatctca cttttatttt tgccatggat gagagtcctg ggtgtgagga    1860
acacctccca ccaggctaga ggcaactgcc caggaaggac tgtgcttccg tcacctctaa    1920
atcccttgca gatccttgat aaatgcctca tgaagaccaa tctcttgaat cccatatcta    1980
cccagaatta actccattcc agtctctgca tgtaatcagt tttatccaca gaaacatttt    2040
cattttagga aatccctggt ttaagtatca atccttgttc agctggacaa tatgaatctt    2100
ttccactgaa gttagggatg actgtgattt tcagaacacg tccagaattt ttcatcaaga    2160
aggtagcttg agcctgaaat gcaaaaccca tggaggaatt ctgaagccat tgtctccttg    2220
agtaccaaca gggtcaggga agactgggcc tcctgaattt attattgttc tttaagaatt    2280
acaggttgag gtagttgatg gtggtaaaca ttctctcagg agacaataac tccagtgatg    2340
```

-continued

```
ttttcaaag attttagcaa aaacagagta aatagcattc tctatcaata tataaattta    2400
aaaaactatc tttttgctta cagttttaaa ttctgaacaa tttctcttat atgtgtattg    2460
ctaatcatta aggtattatt ttttccacat ataaagcttt gtcttttgt tgttgttgtt    2520
gttttaaga tggagtttcc ctctgttgcc aggctagagt gcagtggcat gatctcggct    2580
tactgcaacc tttgcctccc aggtttaagc gattcttctg cctcagcctc ccgagtagct    2640
gggaccacag gtgcctacca ccatgccagg ctaattttg tatttttagt aaagacaggg    2700
tttcaccata ttggccaggc tggtctcgaa ctcctgacct tgtgatctgc ccgcctccat    2760
tgtgttgtta tttgtgagaa agatagatat gaggtttaga gagggatgaa gaggtgagag    2820
taagccttgt gttagtcaga actctgtgtt gtgaatgtca ttcacaacag aaacccaaa    2880
atattatgca aactactgta agcaagaaaa ataaggaaa aatggaaaca tttattcctt    2940
tgcataatag aaattaccag agttgttctg tctttagata aggtttgaac caaagctcaa    3000
aacaatcaag accctttct gtatgtcctt ctgttctgcc ttccgcagtg taggctttac    3060
cctcaggtgc tacacagtat agttctaggg tttccctccc gatatcaaaa agactgtggc    3120
ctgcccagct ctcgtatccc caagccacac catctggcta aatggacatc atgttttctg    3180
gtgatgccca agaggagag aggaagctct cttccccaga tgccccagca agtgtaacct    3240
tgcatctcat tgctctggct gagttgtgtg cctgtttctg accaatcact gagtcaggag    3300
gatgaaatat tcatattgac ttaattgcag cttaagttag gggtatgtag aggtattttc    3360
cctaaagcaa aattgggaca ctgttatcag aaataggaga gtggatgata gatgcaaaat    3420
aataccctgtc cacaacaaac tcttaatgct gtgtttgagc tttcatgagt ttcccagaga    3480
gacatagctg gaaaattcct attgattttc tctaaaattt caacaagtag ctaaagtctg    3540
gctatgctca cagtctcaca tctggtgggg gtgggctcct tacagaacac gctttcacag    3600
ttaccctaaa ctctctgggg caggttatt cctttgtgga accagaggca cagagacagt    3660
caactgaggc ccaacagagg cctgagagaa actgaggtca agatttcagg attaatggtc    3720
ctgtgatgct ttgaagtaca attgtggatt tgtccaattc tctttagttc tgtcagcttt    3780
tgcttcatat attttagcgc tctattatta gatatataca tgtttagtat tatgtcttat    3840
tggtgcattt actctcttat cattatgtaa tgtccttctt tatctgtgat aattttctgt    3900
gttctgaagt ctactttgtc taaaataac atacgcactc aacttccttt tctttcttcc    3960
ttcctttctt tcttccttcc tttctttctc tctctctctt tccttccttc cttcctcctt    4020
ttctctctct ctctctctct ctctcttttc ttgacagact ctcgttctgt ggccctggct    4080
ggagttcagt ggtgtgatct tggctcactg ctacctctac catgagcaat tctcctgcct    4140
cagcctccca gtagctgga actacaggct catgccactg cgcccagcta ttttttgtat    4200
ttttcgtaga cacggggttt caccacattc gtcaggttgg tttcaaactc ctgactttgt    4260
gatccacccg cctcggcctc ccaaagtgct gggattacag gcatgagcca tcacacctgg    4320
tcaactttct tttgattagt gttttgtgg tatatctttt tccatcatgt tactttaaat    4380
atatctatat tattgtattt aaaatgtgtt tcttacagac tgcatgtagt tgggtataat    4440
ttttatccag tctaaaaata tctgtctttt aattggtgtt tagacaattt atatttaata    4500
aaatggtgga atttaaa                                                  4517
```

<210> SEQ ID NO 2
<211> LENGTH: 484
<212> TYPE: DNA

<213> ORGANISM: Homo sapiens

<400> SEQUENCE: 2

```
atgacccggg gctgaaggtc cccgaggctt ccgggaatc caaggcagga aaggagaacc      60
tggagaaggt gcctatgtat accgctcagc attcagtgtg ggattggaga cttacgttac    120
tatccccaac atgcccattc gctttaccaa gatcttctac aatcagcaaa accactatga    180
tggctccact ggtaaattcc actgcaacat tcctgggctg tactactttg cctaccacat    240
cacagtctat atgaaggatg tgaaggtcag cctcttcaag aaggacaagg ctatgctctt    300
cacctatgat cagtaccagg aaaataatgt ggaccaggcc tccggctctg tgctcctgca    360
tctggaggtg ggcgaccaag tctggctcca ggtgtatggg aaggagagc gtaatggact    420
ctatgctgat aatgacaatg actccacctt cacaggcttt cttctctacc atgacaccaa    480
ctga                                                                 484
```

<210> SEQ ID NO 3
<211> LENGTH: 718
<212> TYPE: DNA
<213> ORGANISM: Homo sapiens

<400> SEQUENCE: 3

```
ctgattccat accagagggg ctcaggatgc tgttgctggg agctgttcta ctgctattag      60
ctctgcccgg gcatgaccag gaaaccacga ctcaagggcc cggagtcctg cttcccctgc    120
ccaagggggc ctgcacaggt tggatggcgg catcccagg gcatccgggc cataatgggg    180
ccccaggccg tgatggcaga gatggcaccc ctggtgagaa gggtgagaaa ggagatccag    240
gtcttattgg tcctaaggga gacatcggtg aaaccggagt accgggggct gaaggtcccc    300
gaggctttcc gggaatccaa ggcaggaaag gagaacctgg agaaggtgcg ttactatccc    360
caacatgccc attcgctta ccaagatctt ctacaatcag caaaaccact atgatggctc    420
cactggtaaa ttccactgca acattcctgg gctgtactac tttgcctacc acatcacagt    480
ctatatgaag gatgtgaagg tcagcctctt caagaaggac aaggctatgc tcttcaccta    540
tgatcagtac caggaaaata atgtggacca ggcctccggc tctgtgctcc tgcatctgga    600
ggtgggcgac caagtctggc tccaggtgta tggggaagga gagcgtaatg gactctatgc    660
tgataatgac aatgactcca ccttcacagg cttctttctc taccatgaca ccaactga      718
```

<210> SEQ ID NO 4
<211> LENGTH: 537
<212> TYPE: DNA
<213> ORGANISM: Homo sapiens

<400> SEQUENCE: 4

```
ctgattccat accagagggg ctcaggatgc tgttgctggg agctgttcta ctgctattag      60
ctctgcccgg gcatgaccag gaaaccacga ctcaagggcc cggagtcctg cttcccctgc    120
ccaagggggc ctgcacaggt tggatggcgg catcccagg gcatccgggc cataatgggg    180
ccccaggccg tgatggcaga gatggcaccc ctggtgagaa gggtgagaaa ggagatccag    240
gtcttattgg tcctaaggga gacatcggtg aaaccggagt accgggggct gaaggtcccc    300
gaggctttcc gggaatccaa ggcaggaaag gagaacctgg agaaggtgcc tatgtatacc    360
gctcagcatt cagtgtggga ttggagactt acgttactat ccccaacatg cccattcgct    420
ttaccaagat cttctacaat cagcaaaacc actatgatgg ctccactggt aaattccact    480
gcaacattcc tgggctgtac cttcacaggc tttcttctct accatgacac caactga        537
```

<210> SEQ ID NO 5
<211> LENGTH: 1306
<212> TYPE: DNA
<213> ORGANISM: Mus musculus

<400> SEQUENCE: 5

```
atgagacctg gccactttct cctcatttct gtctgtacga ttgtcagtgg atctgacgac      60
accaaaaggg ctcaggatgc tactgttgca agctctcctg ttcctcttaa tcctgcccag     120
tcatgccgaa gatgacgtta ctacaactga gagctagct cctgctttgg tccctccacc     180
caagggaact tgtgcaggtt ggatggcagg catcccagga catcctggcc acaatggcac     240
accaggccgt gatggcagag atggcactcc tggagagaag ggagagaaag agatgcagg     300
tcttcttggt cctaaggggtg agacaggaga tgttggaatg acaggagctg aagggccacg     360
ggcttcccc ggaaccctg gcaggaaagg agagcctgga gaagccgctt atgtgtatcg     420
ctcagcgttc agtgtggggc tggagacccg cgtcactgtt cccaatgtac ccattcgctt     480
tactaagatc ttctacaacc aacagaatca ttatgacggc agcactggca agttctactg     540
caacattccg ggactctact acttctctta ccacatcacg gtgtacatga agatgtgaa      600
ggtgagcctc ttcaagaagg acaaggccgt tctcttcacc tacgaccagt atcaggaaaa     660
gaatgtggac caggcctctg gctctgtgct cctccatctg gaggtgggag accaagtctg     720
gctccaggtg tatggggatg ggaccacaa tggactctat gcagataacg tcaacgactc     780
tacatttact ggctttcttc tctaccatga taccaactga ctgcaactac ccatagccca     840
tacaccagga gaatcatgga acagtcgaca cactttcagc ttagtttgag agattgattt     900
tattgcttag tttgagagtc ctgagtatta tccacacgtg tactcacttg ttcattaaac     960
gactttataa aaaataattt gtgttcctag tccagaaaaa aaggcactcc ctggtctcca    1020
cgactcttac atggtagcaa taacagaatg aaaatcacat ttggtatggg ggcttcacaa    1080
tattcgcatg actgtctgga agtagaccat gctatttttc tgctcactgt acacaaatat    1140
tgttcacata aaccctataa tgtaaatatg aaatacagtg attactcttc tcacaggctg    1200
astgtatgaa ttctaaagac ccataagtat taaagtggta gggataaatt ggaaaaaaaa    1260
aaaaaaaaaa agaaaaactt tagagcacac tggcggccgt tactag                  1306
```

<210> SEQ ID NO 6
<211> LENGTH: 1184
<212> TYPE: DNA
<213> ORGANISM: Mus musculus

<400> SEQUENCE: 6

```
gctcattcat cttttaattc acccataaag gctttgaaaa ctaaggctgg agatgaactt      60
ataggagcct gccaggccgt ggagagtgag gaagcagaga tgacggagat gatgtctttc     120
cttgtcctgt gaaatggatt gtgggtagag gttccggaga taatgcctct tgctggaaac     180
agtctgggca gttctgttcc cgccattcac agaattcttc tcactttcta ggtcttcttg     240
gtcctaaggg tgagacagga gatgttggaa tgacaggagc tgaagggcca cggggcttcc     300
ccggaacccc tggcaggaaa ggagagcctg gagaagccgc ttatgtgtat cgctcagcgt     360
tcagtgtggg gctggagacc cgcgtcactg ttcccaatgt acccattcgc tttactaaga     420
tcttctacaa ccaacagaat cattatgacg gcagcactgg caagttctac tgcaacattc     480
cgggactcta ctacttctct taccacatca cggtgtacat gaaagatgtg aaggtgagcc     540
```

| | |
|---|---|
| tcttcaagaa ggacaaggcc gttctcttca cctacgacca gtatcaggaa agaatgtgg | 600 |
| accaggcctc tggctctgtg ctcctccatc tggaggtggg agaccaagtc tggctccagg | 660 |
| tgtatgggga tggggaccac aatggactct atgcagataa cgtcaacgac tctacattta | 720 |
| ctggctttct tctctaccat gataccaact gactgcaact cccatagcc catacaccag | 780 |
| gagaatcatg gaacagtcga cacactttca gcttagtttg agagattgat tttattgctt | 840 |
| agtttgagag tcctgagtat tatccacacg tgtactcact tgttcattaa cgactttat | 900 |
| aaaaaataat ttgtgttcct agtccagaaa aaaaggcact ccctggtctc cacgactctt | 960 |
| acatggtagc aataacagaa tgaaaatcac atttggtatg ggggcttcac aatattcgca | 1020 |
| tgactgtctg gaagtagacc atgctatttt tctgctcact gtacacaaat attgttcaca | 1080 |
| taaaccctat aatgtaaata tgaaatacag tgattactct tctcacaggc tgagtgtatg | 1140 |
| aattctaaag acccataagt attaaagtgg tagggataaa ttgg | 1184 |

<210> SEQ ID NO 7
<211> LENGTH: 1209
<212> TYPE: DNA
<213> ORGANISM: Mus musculus

<400> SEQUENCE: 7

| | |
|---|---|
| atgagacctg ccactttct cctcatttct gtctgtacga ttgtcagtgg atctgacgac | 60 |
| accaaaaggg ctcaggatgc tactgttgca agctctcctg ttcctcttaa tcctgcccag | 120 |
| tcatgccgaa gatgacgtta ctacaactga agagctagct cctgctttgg tccctccacc | 180 |
| caagggaact tgtgcaggtt ggatggcagg catcccagga catcctggcc acaatggcac | 240 |
| accaggccgt gatggcagag atggcactcc tggagagaag ggagagaaag agatgcagg | 300 |
| tcttcttggt cctaagggtg agacaggaga tgttggaatg acaggagctg aagggccacg | 360 |
| gggcttcccc ggaacccctg gcaggaaagg agagcctgga gaagccgcgt cactgttccc | 420 |
| aatgtaccca ttcgctttac taagatcttc tacaaccaac agaatcatta tgacggcagc | 480 |
| actggcaagt tctactgcaa cattccggga ctctactact tctcttacca catcacggtg | 540 |
| tacatgaaag atgtgaaggt gagcctcttc aagaaggaca aggccgttct cttcacctac | 600 |
| gaccagtatc aggaaaagaa tgtggaccag gcctctggct ctgtgctcct ccatctggag | 660 |
| gtgggagacc aagtctggct ccaggtgtat ggggatgggg accacaatgg actctatgca | 720 |
| gataacgtca acgactctac atttactggc tttcttctct accatgatac caactgactg | 780 |
| caactaccca tagcccatac accaggagaa tcatggaaca gtcgacacac tttcagctta | 840 |
| gtttgagaga ttgattttat tgcttagttt gagagtcctg agtattatcc acacgtgtac | 900 |
| tcacttgttc attaaacgac tttataaaaa ataatttgtg ttcctagtcc agaaaaaaag | 960 |
| gcactccctg gtctccacga ctcttacatg gtagcaataa cagaatgaaa atcacatttg | 1020 |
| gtatggggc ttcacaatat tcgcatgact gtctggaagt agaccatgct attttctgc | 1080 |
| tcactgtaca caaatattgt tcacataaac cctataatgt aaatatgaaa tacagtgatt | 1140 |
| actcttctca caggctgagt gtatgaattc taaagaccca taagtattaa agtggtaggg | 1200 |
| ataaattgg | 1209 |

<210> SEQ ID NO 8
<211> LENGTH: 1028
<212> TYPE: DNA
<213> ORGANISM: Mus musculus

<400> SEQUENCE: 8

```
atgagacctg gccactttct cctcatttct gtctgtacga ttgtcagtgg atctgacgac    60
accaaaaggg ctcaggatgc tactgttgca agctctcctg ttcctcttaa tcctgcccag   120
tcatgccgaa gatgacgtta ctacaactga agagctagct cctgctttgg tccctccacc   180
caagggaact tgtgcaggtt ggatggcagg catcccagga catcctggcc acaatggcac   240
accaggccgt gatggcagag atggcactcc tggagagaag ggagagaaag agatgcagg    300 tcttcttggt cctaagggtg agacaggaga tgttggaatg acaggagctg aagggccacg   360
gggcttcccc ggaaccctg gcaggaaagg agagcctgga gaagccgctt atgtgtatcg    420
ctcagcgttc agtgtggggc tggagacccg cgtcactgtt cccaatgtac ccattcgctt   480
tactaagatc ttctacaacc aacagaatca ttatgacggc agcactggca agttctactg   540
caacattccg ggactctaca tttactggct ttcttctcta ccatgatacc aactgactgc   600
aactacccat agcccataca ccaggagaat catggaacag tcgacacact ttcagcttag   660
tttgagagat tgattttatt gcttagtttg agagtcctga gtattatcca cacgtgtact   720
cacttgttca ttaaacgact ttataaaaaa taatttgtgt tcctagtcca gaaaaaaagg   780
cactccctgg tctccacgac tcttacatgg tagcaataac agaatgaaaa tcacatttgg   840
tatgggggct tcacaatatt cgcatgactg tctggaagta gaccatgcta tttttctgct   900
cactgtacac aaatattgtt cacataaacc ctataatgta aatatgaaat acagtgatta   960
ctcttctcac aggctgagtg tatgaattct aaagacccat aagtattaaa gtggtaggga  1020
taaattgg                                                           1028
```

<210> SEQ ID NO 9
<211> LENGTH: 306
<212> TYPE: DNA
<213> ORGANISM: Mus musculus

<400> SEQUENCE: 9

```
atgagacctg gccactttct cctcatttct gtctgtacga ttgtcagtgg atctgacgac    60
accaaaaggg ctcaggatgc tactgttgca agctctcctg ttcctcttaa tcctgcccag   120
tcatgccgaa gatgacgtta ctacaactga agagctagct cctgctttgg tccctccacc   180
caagggaact tgtgcaggtt ggatggcagg catcccagga catcctggcc acataaaaat   240
ataattcgag gggcatccac caggccggct gaattgtgcc aaaatatggc acttcctgca   300
agataa                                                              306
```

<210> SEQ ID NO 10
<211> LENGTH: 665
<212> TYPE: DNA
<213> ORGANISM: Homo sapiens

<400> SEQUENCE: 10

```
actctggatg ggtgctgttt agacaaacgc cgtctcctat ataagacctg acagcacagg    60
caccactccg ccaggactgc aggcccacct gtctgcaacc cagctgaggc catgccctcc   120
ccagggaccg tctgcagcct cctgctcctc ggcatgctct ggctggactt ggccatggca   180
ggctccagct tcctgagccc tgaacaccag agagtccagc agagaaagga gtcgaagaag   240
ccaccagcca agctgcagcc ccgagctcta gcaggctggc tccgcccgga agatggaggt   300
caagcagaag gggcagagga tgaactgaa gtccggttca acgccccctt tgatgttgga   360
atcaagctgt caggggttca gtaccagcag cacagccagg ccctgggaa gtttcttcag   420
```

```
gacatcctct gggaagaggc caaagaggcc ccagccgaca agtgatcgcc cacaagcctt    480
actcacctct ctctaagttt agaagcgctc atctggcttt tcgcttgctt ctgcagcaac    540
tcccacgact gttgtacaag ctcaggaggc gaataaatgt tcaaactgta tgctgatgtt    600
ccaaatggga atttatttca agaggaaaa gttaatattt actttaaaa aaatcaaaat      660 aatac                                                               665

<210> SEQ ID NO 11
<211> LENGTH: 579
<212> TYPE: DNA
<213> ORGANISM: Homo sapiens

<400> SEQUENCE: 11
actctggatg ggtgctgttt agacaaacgc cgtctcctat ataagacctg acagcacagg     60
caccactccg ccaggactgc aggcccacct gtctgcaacc cagctgaggc catgccctcc    120
ccagggaccg tctgcagcct cctgctcctc ggcatgctct ggctggactt ggccatggca    180
ggctccagct tcctgagccc tgaacaccag agagtccagg tgagacctcc cacaaagcc    240 ccacatgttg ttccagccct gccacttagc aaccagctct gtgacctgga gcagcagcgc    300
catctctggg cttcagtctt ctcccagagc acaaaggact ctgggtctga cctcactgtt    360
tctggaagga catgggggct tagagtccta aacagactgt ttccccttc cagcagagaa     420 aggagtcgaa gaagccacca gccaagctgc agccccgagc tctagcaggc tggctccgcc    480
cggaagatgg aggtcaagca gaaggggcag aggatgaact ggaagtccgg gtcggtacct    540
ctgcagtttt atgcttctgt ggcagcgagg agggtgggg                           579

<210> SEQ ID NO 12
<211> LENGTH: 1448
<212> TYPE: DNA
<213> ORGANISM: Homo sapiens

<400> SEQUENCE: 12
gcactgcctg agactactcc agcctccccc gtccctgatg tcacaattca gaggctgctg     60
cctgcttagg aggttgtaga aagctctgta ggttctctct gtgtgtccta caggagtctt    120
caggccagct ccctgtcgga tggcttttat gaaaaaatat ctcctcccca ttctggggct    180
cttcatggcc tactactact attctgcaaa cgaggaattc agaccagaga tgctccaagg    240
aaagaaagtg attgtcacag gggccagcaa agggatcgga agagagatgg cttatcatct    300
ggcgaagatg ggagcccatg tggtggtgac agcgaggtca aaagaaactc tacagaaggt    360
ggtatcccac tgcctggagc ttggagcagc tcagcacac tacattgctg gcaccatgga    420
agacatgacc ttcgcagagc aatttgttgc ccaagcagga agctcatgg gaggactaga    480 catgctcatt ctcaaccaca tcaccaacac ttctttgaat ctttttcatg atgatattca    540
ccatgtgcgc aaaagcatgg aagtcaactt cctcagttac gtggtcctga ctgtagctgc    600
cttgcccatg ctgaagcaga gcaatggaag cattgttgtc gtctcctctc tggctgggaa    660
agtggcttat ccaatggttg ctgcctattc tgcaagcaag tttgctttgg atgggttctt    720
ctcctccatc agaaaggaat attcagtgtc cagggtcaat gtatcaatca ctctctgtgt    780
tcttggcctc atagacacag aaacagccat gaaggcagtt tctgggatag tccatatgca    840
agcagctcca aaggaggaat gtgccctgga gatcatcaaa gggggagctc tgcgccaaga    900
agaagtgtat tatgacagct cactctggac cactcttctg atcagaaatc catgcaggaa    960
gatcctggaa tttctctact caacgagcta taatatggac agattcataa acaagtagga   1020
```

```
actccctgag ggctgggcat gctgagggat tttgggactg ttctgtctca tgtttatctg    1080
agctcttatc tatgaagaca tcttcccaga gtgtccccag agacatgcaa gtcatgggtc    1140
acacctgaca aatggaagga gttcctctaa catttgcaaa atggaaatgt aataataatg    1200
aatgtcatgc accgctgcag ccagcagttg taaaattgtt agtaaacata ggtataatta    1260
ccagatagtt atattaaatt tatatcttat atataataat atgtgatgat taatacaata    1320
ttaattataa taaaggtcac ataaacttta taaattcata actggtagct ataacttgag    1380
cttattcagg atggtttctt taaaaccata aactgtacaa atgaaatttt tcaatatttg    1440
tttctttat                                                             1448

<210> SEQ ID NO 13
<211> LENGTH: 708
<212> TYPE: DNA
<213> ORGANISM: Homo sapiens
<220> FEATURE:
<221> NAME/KEY: misc_feature
<222> LOCATION: (626)..(626)
<223> OTHER INFORMATION: n is a, g, c, or t

<400> SEQUENCE: 13
gcactgcctg agactactcc agcctcccccc gtccctgatg tcacaattca gaggctgctg     60
cctgcttagg aggttgtaga aagctctgta ggttctctct gtgtgtccta caggagtctt    120
caggccagct ccctgtcgga tggcttttat gaaaaaatat ctcctcccca ttctggggct    180
cttcatggcc tactactact attctgcaaa cgaggaattc agaccagaga tgctccaagg    240
aaagaaagtg attgtcacag gggccagcaa agggatcgga agagagatgg cttatcatct    300
ggcgaagatg ggagcccatg tggtggtgac agcgagctca gcacactaca ttgctggcac    360
catggaagac atgaccttcg cagagcaatt tgttgcccaa gcaggaaagc tcatgggagg    420
actagacatg ctcattctca accacatcac caacacttct ttgaatcttt ttcatgatga    480 tattccaccat gtgcgcaaaa gcatggaagt caacttcctc agttacgtgg tcctgactgt    540
agctgccttg cccatgctga agcagagcaa tggaagcatg tgcgctcttc tgctggaatg    600
ctatcatgtt gtgcatctga gcagtngttg atggtctctc tcatagaaga tatcaggcag    660
gcatgatata ctttggtctg ctataccaga cgctaggcgt ctgatgca                 708

<210> SEQ ID NO 14
<211> LENGTH: 1394
<212> TYPE: DNA
<213> ORGANISM: Homo sapiens

<400> SEQUENCE: 14
gcactgcctg agactactcc agcctcccccc gtccctgatg tcacaattca gaggctgctg     60
cctgcttagg aggttgtaga aagctctgta ggttctctct gtgtgtccta caggagtctt    120
caggccagct ccctgtcgga tggcttttat gaaaaaatat ctcctcccca ttctggggct    180
cttcatggcc tactactact attctgcaaa cgaggaattc agaccagaga tgctccaagg    240
aaagaaagtg attgtcacag gggccagcaa agggatcgga agagagatgg cttatcatct    300
ggcgaagatg ggagcccatg tggtggtgac agcgaggtca aaagaaactc tacagaaggt    360
ggtatcccac tgcctggagc ttggagcagc ctcagcacac tacattgctg gcaccatgga    420
agacatgacc ttcgcagagc aatttgttgc ccaagcagga agctcatgg gaggactaga    480 catgctcatt ctcaaccaca tcaccaacac ttctttgaat cttttcatg atgatattca    540
```

-continued

```
ccatgtgcgc aaaagcatgg aagtcaactt cctcagttac gtggtcctga ctgtagctgc      600
cttgcccatg ctgaagcaga gcaatggaag cattgttgtc gtctcctctc tggctgggaa      660
agtggcttat ccaatggttg ctgcctattc tgcaagcaag tttgctttgg atgggttctt      720
ctcctccatc agaaaggaat attcagtgtc cagggtcaat gtatcaatca ctctctgtgt      780
tcttggcctc atagacacag aaacagccat gaaggcagtt tctgggatag tccatatgca      840
agcagctcca aaggaggaat gtgccctgga gatcatcaaa gggggagctc tgcgccaaga      900
agaagtgtat tatgcagct cactctggac cactcttctg atcagaaatc catgcaggaa       960
gatcctggaa tttctctact caacgagcta taatatggag ggactgttct gtctcatgtt     1020
tatctgagct cttatctatg aagacatctt cccagagtgt ccccagagac atgcaagtca     1080
tgggtcacac ctgacaaatg aaggagttc ctctaacatt tgcaaaatgg aaatgtaata      1140
ataatgaatg tcatgcaccg ctgcagccag cagttgtaaa attgttagta aacataggta     1200
taattaccag atagttatat taaatttata tcttatatat aataatatgt gatgattaat     1260
acaatattaa ttataataaa ggtcacataa actttataaa ttcataactg gtagctataa     1320
cttgagctta ttcaggatgg tttctttaaa accataaact gtacaaatga aattttttcaa    1380
tatttgtttc ttat                                                      1394
```

<210> SEQ ID NO 15
<211> LENGTH: 1394
<212> TYPE: DNA
<213> ORGANISM: Homo sapiens

<400> SEQUENCE: 15

```
gcactgcctg agactactcc agcctcccc gtccctgatg tcacaattca gaggctgctg       60
cctgcttagg aggttgtaga aagctctgta ggttctctct gtgtgtccta caggagtctt     120
caggccagct ccctgtcgga tggcttttat gaaaaaatat ctcctcccca ttctggggct     180
cttcatggcc tactactact attctgcaaa cgaggaattc agaccagaga tgctccaagg     240
aaagaaagtg attgtcacag gggccagcaa agggatcgga agagagatgg cttatcatct     300
ggcgaagatg ggagcccatg tggtggtgac agcgaggtca aaagaaactc tacagaaggt     360
ggtatcccac tgcctggagc ttggagcagc ctcagcacac tacattgctg gcaccatgga     420
agacatgacc ttcgcagagc aatttgttgc ccaagcagga aagctcatgg gaggactaga     480
catgctcatt ctcaaccaca tcaccaacac ttctttgaat cttttcatg atgatattca      540
ccatgtgcgc cccatgctga agcagagcaa tggaagcatt gttgtcgtct cctctctggc     600
tgggaaagtg gcttatccaa tggttgctgc ctattctgca agcaagtttg ctttggatgg     660
gttcttctcc tccatcagaa aggaatattc agtgtccagg gtcaatgtat caatcactct     720
ctgtgttctt ggcctcatag acacagaaac agccatgaag gcagtttctg ggatagtcca     780
tatgcaagca gctccaaagg aggaatgtgc cctggagatc atcaaagggg agctctgcg      840
ccaagaagaa gtgtattatg cagctcact ctggaccact cttctgatca gaaatccatg      900
caggaagatc ctggaatttc tctactcaac gagctataat atggacagat tcataaacaa     960
gtaggaactc cctgagggct gggcatgctg agggattttg ggactgttct gtctcatgtt    1020
tatctgagct cttatctatg aagacatctt cccagagtgt ccccagagac atgcaagtca    1080
tgggtcacac ctgacaaatg aaggagttc ctctaacatt tgcaaaatgg aaatgtaata     1140
ataatgaatg tcatgcaccg ctgcagccag cagttgtaaa attgttagta aacataggta    1200
taattaccag atagttatat taaatttata tcttatatat aataatatgt gatgattaat    1260
```

```
acaatattaa ttataataaa ggtcacataa actttataaa ttcataactg gtagctataa    1320
cttgagctta ttcaggatgg tttctttaaa accataaact gtacaaatga aatttttcaa    1380
tatttgtttc ttat                                                      1394

<210> SEQ ID NO 16
<211> LENGTH: 1394
<212> TYPE: DNA
<213> ORGANISM: Homo sapiens

<400> SEQUENCE: 16
gcactgcctg agactactcc agcctccccc gtccctgatg tcacaattca gaggctgctg      60
cctgcttagg aggttgtaga aagctctgta ggttctctct gtgtgtccta caggagtctt    120
caggccagct ccctgtcgga tggctttat gaaaaaatat ctcctcccca ttctggggct     180
cttcatggcc tactactact attctgcaaa cgaggaattc agaccagaga tgctccaagg    240
aaagaaagtg attgtcacag gggccagcaa agggatcgga agagagatgg cttatcatct    300
ggcgaagatg ggagcccatg tggtggtgac agcgagctca gcacactaca ttgctggcac    360
catggaagac atgaccttcg cagagcaatt tgttgcccaa gcaggaaagc tcatgggagg    420
actagacatg ctcattctca accacatcac caacacttct ttgaatcttt ttcatgatga    480
tattcaccat gtgcgcaaaa gcatggaagt caacttcctc agttacgtgg tcctgactgt    540
agctgccttg cccatgctga agcagagcaa tggaagcatt gttgtcgtct cctctctggc    600
tgggaaagtg gcttatccaa tggttgctgc ctattctgca agcaagtttg ctttggatgg    660
gttcttctcc tccatcagaa aggaatattc agtgtccagg gtcaatgtat caatcactct    720
ctgtgttctt ggcctcatag acacagaaac agccatgaag gcagtttctg ggatagtcca    780
tatgcaagca gctccaaagg aggaatgtgc cctggagatc atcaaagggg gagctctgcg    840
ccaagaagaa gtgtattatg acagctcact ctggaccact cttctgatca gaaatccatg    900
caggaagatc ctggaatttc tctactcaac gagctataat atggacagat tcataaacaa    960
gtaggaactc cctgagggct gggcatgctg agggattttg ggactgttct gtctcatgtt   1020
tatctgagct cttatctatg aagacatctt cccagagtgt ccccagagac atgcaagtca   1080
tgggtcacac ctgacaaatg gaaggagttc ctctaacatt tgcaaaatgg aaatgtaata   1140
ataatgaatg tcatgcaccg ctgcagccag cagttgtaaa attgttagta aacataggta   1200
taattaccag atagttatat taaatttata tcttatatat aataatatgt gatgattaat   1260
acaatattaa ttataataaa ggtcacataa actttataaa ttcataactg gtagctataa   1320
cttgagctta ttcaggatgg tttctttaaa accataaact gtacaaatga aatttttcaa   1380
tatttgtttc ttat                                                     1394

<210> SEQ ID NO 17
<211> LENGTH: 1821
<212> TYPE: DNA
<213> ORGANISM: Homo sapiens

<400> SEQUENCE: 17
ggtgaaaagg gaaaacctgc ccaaatccag ttttttgtttc agtaacttcc tttgagacaa     60
agtcaggaat ctgagagtaa gcacctgcta agggtgggac aggggctctg tctggtatgc    120
ctctcccatg ttaagagcta acaatagtaa tggataagtc tccagggcaa ccaggaccac    180
ttccaagcat tcctgtcttg ggctgcctcg agggctcctc tgtcctttgg ggagtactga    240
```

```
ttgatgcctg atgcccagaa ctggcccact ctggcttctc tttggagctg tctctgcagg      300
cgccttctgg ctgccagctc ggtcctagca taagggactt cttccttggc ctgggtttca      360
ccttcttgta tcaggtggca gaccagctgg tttcagtccc aaatcaggtc ttctgactcc      420
tcccagaaac caaccaactt ctgagcagga atcctgccc  ctccccaaag agtgggaaac      480
cgcaaaggaa gagagagatg aaacagaagg aaaggcagag gaggagggag agagagagaa      540
gagaagaaaa agaaaaaaga acatcaataa aaagaagtca gatttgttcg aaatcttgag      600
agatgctcca aggaaagaaa gtgattgtca caggggccag caaagggatc ggaagagaga      660
tggcttatca tctggcgaag atgggagccc atgtggtggt gacagcgagg tcaaaagaaa      720
ctctacagaa ggtggtatcc cactgcctgg agcttggagc agcctcagca cactacattg      780
ctggcaccat ggaagacatg accttcgcag agcaatttgt tgcccaagca ggaaagctca      840
tgggaggact agacatgctc attctcaacc acatcaccaa cacttctttg aatctttttc      900
atgatgatat tcaccatgtg cgcaaaagca tggaagtcaa cttcctcagt tacgtggtcc      960
tgactgtagc tgccttgccc atgctgaagc agagcaatgg aagcattgtt gtcgtctcct     1020
ctctggctgg gaaagtggct tatccaatgg ttgctgccta ttctgcaagc aagtttgctt     1080
tggatgggtt cttctcctcc atcagaaagg aatattcagt gtccagggtc aatgtatcaa     1140
tcactctctg tgttcttggc ctcatagaca cagaaacagc catgaaggca gtttctggga     1200
tagtccatat gcaagcagct ccaaaggagg aatgtgccct ggagatcatc aaaggggag      1260 ctctgcgcca agaagaagtg tattatgaca gctcactctg gaccactctt ctgatcagaa     1320
atccatgcag gaagatcctg gaatttctct actcaacgag ctataatatg gacagattca     1380
taaacaagta ggaactccct gagggctggg catgctgagg gattttggga ctgttctgtc     1440
tcatgtttat ctgagctctt atctatgaag acatcttccc agagtgtccc cagagacatg     1500
caagtcatgg gtcacacctg acaaatgaaa ggagttcctc taacatttgc aaaatggaaa     1560
tgtaataata atgaatgtca tgcaccgctg cagccagcag ttgtaaaatt gttagtaaac     1620
ataggtataa ttaccagata gttatattaa atttatatct tatatataat aatatgtgat     1680
gattaataca atattaatta taataaaggt cacataaact ttataaattc ataactggta     1740
gctataactt gagcttattc aggatggttt ctttaaaacc ataaactgta caaatgaaat     1800 tttcaatat ttgtttctta t                                                1821
```

<210> SEQ ID NO 18
<211> LENGTH: 1304
<212> TYPE: DNA
<213> ORGANISM: Homo sapiens

<400> SEQUENCE: 18

```
gcactgcctg agactactcc agcctccccc gtccctgatg tcacaattca gaggctgctg       60
cctgcttagg aggttgtaga aagctctgta ggttctctct gtgtgtccta caggagtctt      120
caggccagct ccctgtcgga tggcttttat gaaaaaatat ctcctcccca ttctggggct      180
cttcatggcc tactactact attctgcaaa cgaggaattc agaccagaga tgctccaagg      240
aaagaaagtg attgtcacag gggccagcaa aggatcgga  agagagatgg cttatcatct      300
ggcgaagatg ggagcccatg tggtggtgac agcgaggtca aagaaactc  tacagaaggt      360 ggtatcccac tgcctggagc ttggagcagc tcagcacac  tacattgctg gcaccatgga      420
agacatgacc ttcgcagagc aatttgttgc ccaagcagga aagctcatgg gaggactaga      480
catgctcatt ctcaaccaca tcaccaacac ttctttgaat cttttcatg  atgatattca      540
```

-continued

```
ccatgtgcgc aaaagcatgg aagtcaactt cctcagttac gtggtcctga ctgtagctgc      600
cttgcccatg ctgaagcaga gcaatggaag cattgttgtc gtctcctctc tggctgaaac      660
agccatgaag gcagtttctg ggatagtcca tatgcaagca gctccaaagg aggaatgtgc      720
cctggagatc atcaaagggg gagctctgcg ccaagaagaa gtgtattatg acagctcact      780
ctggaccact cttctgatca gaaatccatg caggaagatc ctggaatttc tctactcaac      840
gagctataat atggacagat tcataaacaa gtaggaactc cctgagggct gggcatgctg      900
agggattttg ggactgttct gtctcatgtt tatctgagct cttatctatg aagacatctt      960
cccagagtgt ccccagagac atgcaagtca tgggtcacac ctgacaaatg aaggagttc     1020 ctctaacatt tgcaaaatgg aaatgtaata ataatgaatg tcatgcaccg ctgcagccag     1080
cagttgtaaa attgttagta aacataggta taattaccag atagttatat taaatttata     1140
tcttatatat aataatatgt gatgattaat acaatattaa ttataataaa ggtcacataa     1200
actttataaa ttcataactg gtagctataa cttgagctta ttcaggatgg tttctttaaa     1260
accataaact gtacaaatga aattttcaa tatttgtttc ttat                       1304
```

<210> SEQ ID NO 19
<211> LENGTH: 1307
<212> TYPE: DNA
<213> ORGANISM: Mus musculus

<400> SEQUENCE: 19

```
actgttggcc tctggawtca gaggctgctg cctgcctggg aggttgtaga aagctctgca      60
ggttttcttc gtgtgtccta cagggcgccc tgagccaggt ccctgtttga tggcagttat     120
gaaaaattac ctcctcccga tcctggtgct cttcctggcc tactactact attctacaaa     180
tgaagagttc agaccagaaa tgctccaggg aaagaaagtg attgtcactg gggccagcaa     240
agggattgga agagaaatgg catatcatct gtcaaaaatg ggagcccatg tggtattgac     300
tgccaggtcg gaggaaggtc tccagaaggt agtgtctcgc tgccttgaac tcggagcagc     360
ctctgctcac tacattgctg cactatggaa agacatgaca tttgcggagc aatttattgt     420
caaggcggga aagctcatgg gcggactgga catgcttatt ctaaaccaca tcactcagac     480
ctcgctgtct ctcttccatg acgacatcca ctctgtgcga agagtcatgg aggtcaactt     540
cctcagctac gtggtcatga gcacagccgc cttgcccatg ctgaagcaga gcaatggcag     600
cattgccgtc atctcctcct ggctgggaa aatgacccag cctatgattg ctccctactc      660
tgcaagcaag tttgctctgg atgggttctt ttccaccatt agaacagaac tctacataac     720
caaggtcaac gtgtccatca ctctctgtgt ccttggcctc atagacacag aaacagctat     780
gaaggaaatc tctgggataa ttaacgccca agcttctccc aaggaggagt gcgccctgga     840
gatcatcaaa ggcacagctc tacgcaaaag cgaggtgtac tatgacaaat cgcctttgac     900
tccaatcctg cttgggaacc caggaaggaa gatcatggaa tttttttcat tacgatatta     960
taataaggac atgtttgtaa gtaactagga actcctgagc cctggtgagt ggtcttagaa     1020
cagtcctgcc tgatacttct gtaagcccta cccacaaaag tatctttcca gagatacaca     1080 aatttttgggg tacacctcat catgagaaat tcttgcaaca cttgcacagt gaaaatgtaa     1140
ttgtaataaa tgtcacaaac cactttgggg cctgcagttg tgaacttgat tgtaactatg     1200
gatataaaca catagtggtt gtatcggctt tacctcacac tgaatgaaac aatgataact     1260
aatgtaacat taaatataat aaaggtaata tcaactttgt aaatgca                   1307
```

<210> SEQ ID NO 20
<211> LENGTH: 1181
<212> TYPE: DNA
<213> ORGANISM: Mus musculus

<400> SEQUENCE: 20

| | | | | | |
|---|---|---|---|---|---|
| actgttggcc | tctggawtca | gaggctgctg | cctgcctggg | aggttgtaga | aagctctgca | 60 |
| ggttttcttc | gtgtgtccta | cagggcgccc | tgagccaggt | ccctgtttga | tggcagttat | 120 |
| gaaaaattac | ctcctcccga | tcctggtgct | cttcctggcc | tactactact | attctacaaa | 180 |
| tgaagagttc | agactccaga | aggtagtgtc | tcgctgcctt | gaactcggag | cagcctctgc | 240 |
| tcactacatt | gctggcacta | tggaagacat | gacatttgcg | gagcaattta | ttgtcaaggc | 300 |
| gggaaagctc | atgggcggac | tggacatgct | tattctaaac | cacatcactc | agacctcgct | 360 |
| gtctctcttc | catgacgaca | tccactctgt | gcgaagagtc | atggaggtca | acttcctcag | 420 |
| ctacgtggtc | atgagcacag | ccgccttgcc | catgctgaag | cagagcaatg | cagcattgc | 480 |
| cgtcatctcc | tccttggctg | ggaaaatgac | ccagcctatg | attgctccct | actctgcaag | 540 |
| caagtttgct | ctggatgggt | tcttttccac | cattagaaca | gaactctaca | taaccaaggt | 600 |
| caacgtgtcc | atcactctct | gtgtccttgg | cctcatagac | acagaaacag | ctatgaagga | 660 |
| aatctctggg | ataattaacg | cccaagcttc | tcccaaggag | gagtgcgccc | tggagatcat | 720 |
| caaaggcaca | gctctacgca | aaagcgaggt | gtactatgac | aaatcgcctt | tgactccaat | 780 |
| cctgcttggg | aacccaggaa | ggaagatcat | ggaatttttt | tcattacgat | attataataa | 840 |
| ggacatgttt | gtaagtaact | aggaactcct | gagccctggt | gagtggtctt | agaacagtcc | 900 |
| tgcctgatac | ttctgtaagc | cctacccaca | aagtatctt | tccagagata | cacaaatttt | 960 |
| ggggtacacc | tcatcatgag | aaattcttgc | aacacttgca | cagtgaaaat | gtaattgtaa | 1020 |
| taaatgtcac | aaaccacttt | ggggcctgca | gttgtgaact | tgattgtaac | tatggatata | 1080 |
| aacacatagt | ggttgtatcg | gctttacctc | acactgaatg | aaacaatgat | aactaatgta | 1140 |
| acattaaata | taataaaggt | aatatcaact | ttgtaaatgc | a | | 1181 |

<210> SEQ ID NO 21
<211> LENGTH: 845
<212> TYPE: DNA
<213> ORGANISM: Mus musculus

<400> SEQUENCE: 21

| | | | | | |
|---|---|---|---|---|---|
| actgttggcc | tctggawtca | gaggctgctg | cctgcctggg | aggttgtaga | aagctctgca | 60 |
| ggttttcttc | gtgtgtccta | cagggcgccc | tgagccaggt | ccctgtttga | tggcagttat | 120 |
| gaaaaattac | ctcctcccga | tcctggtgct | cttcctggcc | tactactact | attctacaaa | 180 |
| tgaagagttc | agaccagaaa | tgctccaggg | aaagaaagtg | attgtcactg | gggccagcaa | 240 |
| agggattgga | agagaaatgg | catatcatct | gtcaaaaatg | ggagcccatg | tggtattgac | 300 |
| tgccaggtcg | gaggaaggtc | tccagaaggt | agtgtctcgc | tgccttgaac | tcggagcagc | 360 |
| ctctgctcac | tacattgctg | gcactatgga | agacatgaca | tttgcggagc | aatttattgt | 420 |
| caaggcggga | aagctcatgg | gcggactgga | catgcttatt | ctaaaccaca | tcactcagac | 480 |
| ctcgctgtct | ctcttccatg | acgacatcca | ctctgtgcga | agagtcatgg | aggtcaactt | 540 |
| cctcagctac | gtggtcatga | gcacagccgc | cttgcccatg | ctgaagcaga | gcaatggcag | 600 |
| cattgccgtc | atctcctcct | tggctggggg | aagaacagtt | ccacaacaga | gaagtcgcag | 660 |
| tgttactcct | gactcccgcg | gcccgtgatt | aatatcacca | gccacagaat | ggactggaac | 720 |

```
cctgtatcga tctggtggga ttggatataa cgaacataga attactcctg agactaccag    780
aactgaatag ttcaaatcaa atcatgccag aatatcagac aaatccaaat ggcaaaacag    840
ttgca                                                                845
```

<210> SEQ ID NO 22
<211> LENGTH: 244
<212> TYPE: PRT
<213> ORGANISM: Homo sapiens

<400> SEQUENCE: 22

```
Met Leu Leu Leu Gly Ala Val Leu Leu Leu Ala Leu Pro Gly His
 1               5                   10                  15

Asp Gln Glu Thr Thr Thr Gln Gly Pro Gly Val Leu Leu Pro Leu Pro
                 20                  25                  30

Lys Gly Ala Cys Thr Gly Trp Met Ala Gly Ile Pro Gly His Pro Gly
             35                  40                  45

His Asn Gly Ala Pro Gly Arg Asp Gly Arg Asp Gly Thr Pro Gly Glu
         50                  55                  60

Lys Gly Glu Lys Gly Asp Pro Gly Leu Ile Gly Pro Lys Gly Asp Ile
 65                  70                  75                  80

Gly Glu Thr Gly Val Pro Gly Ala Glu Gly Pro Arg Gly Phe Pro Gly
                 85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn
```

<210> SEQ ID NO 23
<211> LENGTH: 160
<212> TYPE: PRT
<213> ORGANISM: Homo sapiens

<400> SEQUENCE: 23

```
Met Pro Gly Ala Glu Gly Pro Arg Gly Phe Pro Gly Ile Gln Gly Arg
 1               5                  10                  15

Lys Gly Glu Pro Gly Glu Gly Ala Tyr Val Tyr Arg Ser Ala Phe Ser
                 20                  25                  30

Val Gly Leu Glu Thr Tyr Val Thr Ile Pro Asn Met Pro Ile Arg Phe
             35                  40                  45
```

Thr Lys Ile Phe Tyr Asn Gln Gln Asn His Tyr Asp Gly Ser Thr Gly
    50                  55                  60

Lys Phe His Cys Asn Ile Pro Gly Leu Tyr Tyr Phe Ala Tyr His Ile
65                  70                  75                  80

Thr Val Tyr Met Lys Asp Val Lys Val Ser Leu Phe Lys Lys Asp Lys
                85                  90                  95

Ala Met Leu Phe Thr Tyr Asp Gln Tyr Gln Glu Asn Asn Val Asp Gln
            100                 105                 110

Ala Ser Gly Ser Val Leu Leu His Leu Glu Val Gly Asp Gln Val Trp
        115                 120                 125

Leu Gln Val Tyr Gly Glu Gly Glu Arg Asn Gly Leu Tyr Ala Asp Asn
    130                 135                 140

Asp Asn Asp Ser Thr Phe Thr Gly Phe Leu Leu Tyr His Asp Thr Asn
145                 150                 155                 160

<210> SEQ ID NO 24
<211> LENGTH: 153
<212> TYPE: PRT
<213> ORGANISM: Homo sapiens

<400> SEQUENCE: 24

Met Leu Leu Leu Gly Ala Val Leu Leu Leu Ala Leu Pro Gly His
1               5                   10                  15

Asp Gln Glu Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
    50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Leu Leu Ser Pro
            100                 105                 110

Thr Cys Pro Phe Ala Leu Pro Arg Ser Ser Thr Ile Ser Lys Thr Thr
        115                 120                 125

Met Met Ala Pro Leu Val Asn Ser Thr Ala Thr Phe Leu Gly Cys Thr
    130                 135                 140

Thr Leu Pro Thr Thr Ser Gln Ser Ile
145                 150

<210> SEQ ID NO 25
<211> LENGTH: 166
<212> TYPE: PRT
<213> ORGANISM: Homo sapiens

<400> SEQUENCE: 25

Met Leu Leu Leu Gly Ala Val Leu Leu Leu Ala Leu Pro Gly His
1               5                   10                  15

Asp Gln Glu Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
    50                  55                  60

```
Lys Gly Glu Lys Gly Asp Pro Gly Leu Ile Gly Pro Lys Gly Asp Ile
 65                  70                  75                  80

Gly Glu Thr Gly Val Pro Gly Ala Glu Gly Pro Arg Gly Phe Pro Gly
                 85                  90                  95

Ile Gln Gly Arg Lys Gly Glu Pro Gly Glu Gly Ala Tyr Val Tyr Arg
                100                 105                 110

Ser Ala Phe Ser Val Gly Leu Glu Thr Tyr Val Thr Ile Pro Asn Met
            115                 120                 125

Pro Ile Arg Phe Thr Lys Ile Phe Tyr Asn Gln Gln Asn His Tyr Asp
        130                 135                 140

Gly Ser Thr Gly Lys Phe His Cys Asn Ile Pro Gly Leu Tyr Leu His
145                 150                 155                 160

Arg Leu Ser Ser Leu Pro
                165
```

<210> SEQ ID NO 26
<211> LENGTH: 247
<212> TYPE: PRT
<213> ORGANISM: Mus musculus

<400> SEQUENCE: 26

```
Met Leu Leu Leu Gln Ala Leu Leu Phe Leu Leu Ile Leu Pro Ser His
  1               5                  10                  15

Ala Glu Asp Asp Val Thr Thr Thr Glu Glu Leu Ala Pro Ala Leu Val
                 20                  25                  30

Pro Pro Pro Lys Gly Thr Cys Ala Gly Trp Met Ala Gly Ile Pro Gly
             35                  40                  45

His Pro Gly His Asn Gly Thr Pro Gly Arg Asp Gly Arg Asp Gly Thr
         50                  55                  60

Pro Gly Glu Lys Gly Glu Lys Gly Asp Ala Gly Leu Leu Gly Pro Lys
 65                  70                  75                  80

Gly Glu Thr Gly Asp Val Gly Met Thr Gly Ala Glu Gly Pro Arg Gly
                 85                  90                  95

Phe Pro Gly Thr Pro Gly Arg Lys Gly Glu Pro Gly Glu Ala Ala Tyr
                100                 105                 110

Met Tyr Arg Ser Ala Phe Ser Val Gly Leu Glu Thr Arg Val Thr Val
            115                 120                 125

Pro Asn Val Pro Ile Arg Phe Thr Lys Ile Phe Tyr Asn Gln Gln Asn
        130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr
                180                 185                 190

Gln Glu Lys Asn Val Asp Gln Ala Ser Gly Ser Val Leu Leu His Leu
            195                 200                 205

Glu Val Gly Asp Gln Val Trp Leu Gln Val Tyr Gly Asp Gly Asp His
        210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245
```

<210> SEQ ID NO 27

```
<211> LENGTH: 160
<212> TYPE: PRT
<213> ORGANISM: Mus musculus

<400> SEQUENCE: 27

Met Thr Gly Ala Glu Gly Pro Arg Gly Phe Pro Gly Thr Pro Gly Arg
1               5                   10                  15

Lys Gly Glu Pro Gly Glu Ala Ala Tyr Val Tyr Arg Ser Ala Phe Ser
            20                  25                  30

Val Gly Leu Glu Thr Arg Val Thr Val Pro Asn Val Pro Ile Arg Phe
        35                  40                  45

Thr Lys Ile Phe Tyr Asn Gln Gln Asn His Tyr Asp Gly Ser Thr Gly
    50                  55                  60

Lys Phe Tyr Cys Asn Ile Pro Gly Leu Tyr Tyr Phe Ser Tyr His Ile
65                  70                  75                  80

Thr Val Tyr Met Lys Asp Val Lys Val Ser Leu Phe Lys Lys Asp Lys
                85                  90                  95

Ala Val Leu Phe Thr Tyr Asp Gln Tyr Gln Glu Lys Asn Val Asp Gln
            100                 105                 110

Ala Ser Gly Ser Val Leu Leu His Leu Glu Val Gly Asp Gln Val Trp
        115                 120                 125

Leu Gln Val Tyr Gly Asp Gly Asp His Asn Gly Leu Tyr Ala Asp Asn
    130                 135                 140

Val Asn Asp Ser Thr Phe Thr Gly Phe Leu Leu Tyr His Asp Thr Asn
145                 150                 155                 160

<210> SEQ ID NO 28
<211> LENGTH: 156
<212> TYPE: PRT
<213> ORGANISM: Mus musculus

<400> SEQUENCE: 28

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
            20                  25                  30

Pro Pro Pro Lys Gly Thr Cys Ala Gly Trp Met Ala Gly Ile Pro Gly
        35                  40                  45

His Pro Gly His Asn Gly Thr Pro Gly Arg Asp Gly Arg Asp Gly Thr
    50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Ser
            100                 105                 110

Leu Phe Pro Met Tyr Pro Phe Ala Leu Leu Arg Ser Ser Thr Thr Asn
        115                 120                 125

Arg Ile Ile Met Thr Ala Ala Leu Ala Ser Ser Thr Ala Thr Phe Arg
    130                 135                 140

Asp Ser Thr Thr Ser Leu Thr Thr Ser Arg Cys Thr
145                 150                 155

<210> SEQ ID NO 29
<211> LENGTH: 169
<212> TYPE: PRT
<213> ORGANISM: Mus musculus
```

```
<400> SEQUENCE: 29

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
                20                  25                  30

Pro Pro Pro Lys Gly Thr Cys Ala Gly Trp Met Ala Gly Ile Pro Gly
            35                  40                  45

His Pro Gly His Asn Gly Thr Pro Gly Arg Asp Gly Arg Asp Gly Thr
    50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
            100                 105                 110

Val Tyr Arg Ser Ala Phe Ser Val Gly Leu Glu Thr Arg Val Thr Val
            115                 120                 125

Pro Asn Val Pro Ile Arg Phe Thr Lys Ile Phe Tyr Asn Gln Gln Asn
            130                 135                 140

His Tyr Asp Gly Ser Thr Gly Lys Phe Tyr Cys Asn Ile Pro Gly Leu
145                 150                 155                 160

Tyr Ile Tyr Trp Leu Ser Ser Leu Pro
                165

<210> SEQ ID NO 30
<211> LENGTH: 76
<212> TYPE: PRT
<213> ORGANISM: Mus musculus

<400> SEQUENCE: 30

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
                20                  25                  30

Pro Pro Pro Lys Gly Thr Cys Ala Gly Trp Met Ala Gly Ile Pro Gly
            35                  40                  45

His Pro Gly His Ile Lys Ile Lys Phe Glu Gly His Pro Pro Gly Arg
    50                  55                  60

Leu Asn Cys Ala Lys Ile Trp His Phe Leu Gln Asp
65                  70                  75

<210> SEQ ID NO 31
<211> LENGTH: 117
<212> TYPE: PRT
<213> ORGANISM: Homo sapiens

<400> SEQUENCE: 31

Met Pro Ser Pro Gly Thr Val Cys Ser Leu Leu Leu Gly Met Leu
1               5                   10                  15

Trp Leu Asp Leu Ala Met Ala Gly Ser Ser Phe Leu Ser Pro Glu His
                20                  25                  30

Gln Arg Val Gln Arg Lys Glu Ser Lys Lys Pro Pro Ala Lys Leu
            35                  40                  45

Gln Pro Arg Ala Leu Ala Gly Trp Leu Arg Pro Glu Asp Gly Gly Gln
    50                  55                  60
```

```
Ala Glu Gly Ala Glu Asp Glu Leu Glu Val Arg Phe Asn Ala Pro Phe
 65                  70                  75                  80

Asp Val Gly Ile Lys Leu Ser Gly Val Gln Tyr Gln Gln His Ser Gln
                 85                  90                  95

Ala Leu Gly Lys Phe Leu Gln Asp Ile Leu Trp Glu Gly Ala Lys Glu
            100                 105                 110

Ala Pro Ala Asp Lys
        115

<210> SEQ ID NO 32
<211> LENGTH: 116
<212> TYPE: PRT
<213> ORGANISM: Homo sapiens

<400> SEQUENCE: 32

Met Pro Ser Pro Gly Thr Val Cys Ser Leu Leu Leu Gly Met Leu
 1               5                  10                  15

Trp Leu Asp Leu Ala Met Ala Gly Ser Ser Phe Leu Ser Pro Glu His
                 20                  25                  30

Gln Arg Val Gln Val Arg Pro Pro His Lys Ala Pro His Val Val Pro
             35                  40                  45

Ala Leu Pro Leu Ser Asn Gln Leu Cys Asp Leu Glu Gln Gln Arg His
         50                  55                  60

Trp Ala Ser Val Phe Ser Gln Ser Thr Lys Asp Ser Gly Ser Asp Leu
 65                  70                  75                  80

Thr Val Ser Gly Arg Thr Trp Gly Leu Arg Val Leu Asn Arg Leu Phe
                 85                  90                  95

Pro Pro Ser Ser Arg Glu Arg Ser Arg Arg Ser His Gln Pro Ser Cys
            100                 105                 110

Ser Pro Glu Leu
        115

<210> SEQ ID NO 33
<211> LENGTH: 292
<212> TYPE: PRT
<213> ORGANISM: Homo sapiens

<400> SEQUENCE: 33

Met Ala Phe Met Lys Lys Tyr Leu Leu Pro Ile Leu Gly Leu Phe Met
 1               5                  10                  15

Ala Tyr Tyr Tyr Tyr Ser Ala Asn Glu Glu Phe Arg Pro Glu Met Leu
                 20                  25                  30

Gln Gly Lys Lys Val Ile Val Thr Gly Ala Ser Lys Gly Ile Gly Arg
             35                  40                  45

Glu Met Ala Tyr His Leu Ala Lys Met Gly Ala His Val Val Val Thr
         50                  55                  60

Ala Arg Ser Lys Glu Thr Leu Gln Lys Val Val Ser His Cys Leu Glu
 65                  70                  75                  80

Leu Gly Ala Ala Ser Ala His Tyr Ile Ala Gly Thr Met Glu Asp Met
                 85                  90                  95

Thr Phe Ala Glu Gln Phe Val Ala Gln Ala Gly Lys Leu Met Gly Gly
            100                 105                 110

Leu Asp Met Leu Ile Leu Asn His Ile Thr Asn Thr Ser Leu Asn Leu
        115                 120                 125

Phe His Asp Asp Ile His His Val Arg Lys Ser Met Glu Val Asn Phe
    130                 135                 140
```

```
Leu Ser Tyr Val Val Leu Thr Val Ala Ala Leu Pro Met Leu Lys Gln
145                 150                 155                 160

Ser Asn Gly Ser Ile Val Val Ser Ser Leu Ala Gly Lys Val Ala
            165                 170                 175

Tyr Pro Met Val Ala Ala Tyr Ser Ala Ser Lys Phe Ala Leu Asp Gly
            180                 185                 190

Phe Phe Ser Ser Ile Arg Lys Glu Tyr Ser Val Ser Arg Val Asn Val
            195                 200                 205

Ser Ile Thr Leu Cys Val Leu Gly Leu Ile Asp Thr Glu Thr Ala Met
            210                 215                 220

Lys Ala Val Ser Gly Ile Val His Met Gln Ala Ala Pro Lys Glu Glu
225                 230                 235                 240

Cys Ala Leu Glu Ile Ile Lys Gly Gly Ala Leu Arg Gln Glu Glu Val
                245                 250                 255

Tyr Tyr Asp Ser Ser Leu Trp Thr Thr Leu Leu Ile Arg Asn Pro Cys
            260                 265                 270

Arg Lys Ile Leu Glu Phe Leu Tyr Ser Thr Ser Tyr Asn Met Asp Arg
            275                 280                 285

Phe Ile Asn Lys
    290

<210> SEQ ID NO 34
<211> LENGTH: 163
<212> TYPE: PRT
<213> ORGANISM: Homo sapiens
<220> FEATURE:
<221> NAME/KEY: MISC_FEATURE
<222> LOCATION: (163)..(163)
<223> OTHER INFORMATION: Xaa can be any naturally occuring amino acid

<400> SEQUENCE: 34

Met Ala Phe Met Lys Lys Tyr Leu Leu Pro Ile Leu Gly Leu Phe Met
1               5                   10                  15

Ala Tyr Tyr Tyr Tyr Ser Ala Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ala Lys Met Gly Ala His Val Val Val Thr
    50                  55                  60

Ala Ser Ser Ala His Tyr Ile Ala Gly Thr Met Glu Asp Met Thr Phe
65                  70                  75                  80

Ala Glu Gln Phe Val Ala Gln Ala Gly Lys Leu Met Gly Gly Leu Asp
                85                  90                  95

Met Leu Ile Leu Asn His Ile Thr Asn Thr Ser Leu Asn Leu Phe His
            100                 105                 110

Asp Asp Ile His His Val Arg Lys Ser Met Glu Val Asn Phe Leu Ser
            115                 120                 125

Tyr Val Val Leu Thr Val Ala Ala Leu Pro Met Leu Lys Gln Ser Asn
            130                 135                 140

Gly Ser Met Cys Ala Leu Leu Leu Glu Cys Tyr His Val Val His Leu
145                 150                 155                 160

Ser Ser Xaa

<210> SEQ ID NO 35
<211> LENGTH: 295
<212> TYPE: PRT
<213> ORGANISM: Homo sapiens
```

<400> SEQUENCE: 35

```
Met Ala Phe Met Lys Lys Tyr Leu Leu Pro Ile Leu Gly Leu Phe Met
1               5                   10                  15

Ala Tyr Tyr Tyr Ser Ala Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ala Lys Met Gly Ala His Val Val Val Thr
50                  55                  60

Ala Arg Ser Lys Glu Thr Leu Gln Lys Val Val Ser His Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Val Ala Gln Ala Gly Lys Leu Met Gly Gly
            100                 105                 110

Leu Asp Met Leu Ile Leu Asn His Ile Thr Asn Thr Ser Leu Asn Leu
        115                 120                 125

Phe His Asp Asp Ile His His Val Arg Lys Ser Met Glu Val Asn Phe
    130                 135                 140

Leu Ser Tyr Val Val Leu Thr Val Ala Ala Leu Pro Met Leu Lys Gln
145                 150                 155                 160

Ser Asn Gly Ser Ile Val Val Ser Ser Leu Ala Gly Lys Val Ala
                165                 170                 175

Tyr Pro Met Val Ala Ala Tyr Ser Ala Ser Lys Phe Ala Leu Asp Gly
            180                 185                 190

Phe Phe Ser Ser Ile Arg Lys Glu Tyr Ser Val Ser Arg Val Asn Val
        195                 200                 205

Ser Ile Thr Leu Cys Val Leu Gly Leu Ile Asp Thr Glu Thr Ala Met
210                 215                 220

Lys Ala Val Ser Gly Ile Val His Met Gln Ala Ala Pro Lys Glu Glu
225                 230                 235                 240

Cys Ala Leu Glu Ile Ile Lys Gly Gly Ala Leu Arg Gln Glu Glu Val
                245                 250                 255

Tyr Tyr Asp Ser Ser Leu Trp Thr Thr Leu Leu Ile Arg Asn Pro Cys
            260                 265                 270

Arg Lys Ile Leu Glu Phe Leu Tyr Ser Thr Ser Tyr Asn Met Glu Gly
        275                 280                 285

Leu Phe Cys Leu Met Phe Ile
    290                 295
```

<210> SEQ ID NO 36
<211> LENGTH: 274
<212> TYPE: PRT
<213> ORGANISM: Homo sapiens

<400> SEQUENCE: 36

```
Met Ala Phe Met Lys Lys Tyr Leu Leu Pro Ile Leu Gly Leu Phe Met
1               5                   10                  15

Ala Tyr Tyr Tyr Ser Ala Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ala Lys Met Gly Ala His Val Val Val Thr
50                  55                  60
```

```
Ala Arg Ser Lys Glu Thr Leu Gln Lys Val Val Ser His Cys Leu Glu
 65                  70                  75                  80

Leu Gly Ala Ala Ser Ala His Tyr Ile Ala Gly Thr Met Glu Asp Met
             85                  90                  95

Thr Phe Ala Glu Gln Phe Val Ala Gln Ala Gly Lys Leu Met Gly Gly
        100                 105                 110

Leu Asp Met Leu Ile Leu Asn His Ile Thr Asn Thr Ser Leu Asn Leu
    115                 120                 125

Phe His Asp Asp Ile His His Val Arg Pro Met Leu Lys Gln Ser Asn
130                 135                 140

Gly Ser Ile Val Val Ser Ser Leu Ala Gly Lys Val Ala Tyr Pro
145                 150                 155                 160

Met Val Ala Ala Tyr Ser Ala Ser Lys Phe Ala Leu Asp Gly Phe Phe
                165                 170                 175

Ser Ser Ile Arg Lys Glu Tyr Ser Val Ser Arg Val Asn Val Ser Ile
            180                 185                 190

Thr Leu Cys Val Leu Gly Leu Ile Asp Thr Glu Thr Ala Met Lys Ala
        195                 200                 205

Val Ser Gly Ile Val His Met Gln Ala Ala Pro Lys Glu Glu Cys Ala
210                 215                 220

Leu Glu Ile Ile Lys Gly Gly Ala Leu Arg Gln Glu Glu Val Tyr Tyr
225                 230                 235                 240

Asp Ser Ser Leu Trp Thr Thr Leu Leu Ile Arg Asn Pro Cys Arg Lys
                245                 250                 255

Ile Leu Glu Phe Leu Tyr Ser Thr Ser Tyr Asn Met Asp Arg Phe Ile
            260                 265                 270

Asn Lys

<210> SEQ ID NO 37
<211> LENGTH: 274
<212> TYPE: PRT
<213> ORGANISM: Homo sapiens

<400> SEQUENCE: 37

Met Ala Phe Met Lys Lys Tyr Leu Leu Pro Ile Leu Gly Leu Phe Met
  1               5                  10                  15

Ala Tyr Tyr Tyr Tyr Ser Ala Asn Glu Glu Phe Arg Pro Glu Met Leu
                 20                  25                  30

Gln Gly Lys Lys Val Ile Val Thr Gly Ala Ser Lys Gly Ile Gly Arg
             35                  40                  45

Glu Met Ala Tyr His Leu Ala Lys Met Gly Ala His Val Val Val Thr
 50                  55                  60

Ala Ser Ser Ala His Tyr Ile Ala Gly Thr Met Glu Asp Met Thr Phe
 65                  70                  75                  80

Ala Glu Gln Phe Val Ala Gln Ala Gly Lys Leu Met Gly Gly Leu Asp
                 85                  90                  95

Met Leu Ile Leu Asn His Ile Thr Asn Thr Ser Leu Asn Leu Phe His
            100                 105                 110

Asp Asp Ile His His Val Arg Lys Ser Met Glu Val Asn Phe Leu Ser
        115                 120                 125

Tyr Val Val Leu Thr Val Ala Ala Leu Pro Met Leu Lys Gln Ser Asn
130                 135                 140

Gly Ser Ile Val Val Ser Ser Leu Ala Gly Lys Val Ala Tyr Pro
145                 150                 155                 160
```

```
Met Val Ala Ala Tyr Ser Ala Ser Lys Phe Ala Leu Asp Gly Phe Phe
            165                 170                 175
Ser Ser Ile Arg Lys Glu Tyr Ser Val Ser Arg Val Asn Val Ser Ile
            180                 185                 190
Thr Leu Cys Val Leu Gly Leu Ile Asp Thr Glu Thr Ala Met Lys Ala
            195                 200                 205
Val Ser Gly Ile Val His Met Gln Ala Pro Lys Glu Glu Cys Ala
    210                 215                 220
Leu Glu Ile Ile Lys Gly Gly Ala Leu Arg Gln Glu Glu Val Tyr Tyr
225                 230                 235                 240
Asp Ser Ser Leu Trp Thr Thr Leu Leu Ile Arg Asn Pro Cys Arg Lys
                245                 250                 255
Ile Leu Glu Phe Leu Tyr Ser Thr Ser Tyr Asn Met Asp Arg Phe Ile
            260                 265                 270
Asn Lys
```

<210> SEQ ID NO 38
<211> LENGTH: 262
<212> TYPE: PRT
<213> ORGANISM: Homo sapiens

<400> SEQUENCE: 38

```
Met Leu Gln Gly Lys Lys Val Ile Val Thr Gly Ala Ser Lys Gly Ile
1               5                   10                  15
Gly Arg Glu Met Ala Tyr His Leu Ala Lys Met Gly Ala His Val Val
            20                  25                  30
Val Thr Ala Arg Ser Lys Glu Thr Leu Gln Lys Val Val Ser His Cys
        35                  40                  45
Leu Glu Leu Gly Ala Ala Ser Ala His Tyr Ile Ala Gly Thr Met Glu
    50                  55                  60
Asp Met Thr Phe Ala Glu Gln Phe Val Ala Gln Ala Gly Lys Leu Met
65                  70                  75                  80
Gly Gly Leu Asp Met Leu Ile Leu Asn His Ile Thr Asn Thr Ser Leu
                85                  90                  95
Asn Leu Phe His Asp Asp Ile His His Val Arg Lys Ser Met Glu Val
            100                 105                 110
Asn Phe Leu Ser Tyr Val Val Leu Thr Val Ala Ala Leu Pro Met Leu
        115                 120                 125
Lys Gln Ser Asn Gly Ser Ile Val Val Ser Ser Leu Ala Gly Lys
    130                 135                 140
Val Ala Tyr Pro Met Val Ala Ala Tyr Ser Ala Ser Lys Phe Ala Leu
145                 150                 155                 160
Asp Gly Phe Phe Ser Ser Ile Arg Lys Glu Tyr Ser Val Ser Arg Val
                165                 170                 175
Asn Val Ser Ile Thr Leu Cys Val Leu Gly Leu Ile Asp Thr Glu Thr
            180                 185                 190
Ala Met Lys Ala Val Ser Gly Ile Val His Met Gln Ala Ala Pro Lys
        195                 200                 205
Glu Glu Cys Ala Leu Glu Ile Ile Lys Gly Gly Ala Leu Arg Gln Glu
    210                 215                 220
Glu Val Tyr Tyr Asp Ser Ser Leu Trp Thr Thr Leu Leu Ile Arg Asn
225                 230                 235                 240
Pro Cys Arg Lys Ile Leu Glu Phe Leu Tyr Ser Thr Ser Tyr Asn Met
                245                 250                 255
```

```
Asp Arg Phe Ile Asn Lys
            260

<210> SEQ ID NO 39
<211> LENGTH: 244
<212> TYPE: PRT
<213> ORGANISM: Homo sapiens

<400> SEQUENCE: 39

Met Ala Phe Met Lys Lys Tyr Leu Leu Pro Ile Leu Gly Leu Phe Met
1               5                   10                  15

Ala Tyr Tyr Tyr Tyr Ser Ala Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ala Lys Met Gly Ala His Val Val Val Thr
    50                  55                  60

Ala Arg Ser Lys Glu Thr Leu Gln Lys Val Val Ser His Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Val Ala Gln Ala Gly Lys Leu Met Gly Gly
            100                 105                 110

Leu Asp Met Leu Ile Leu Asn His Ile Thr Asn Thr Ser Leu Asn Leu
        115                 120                 125

Phe His Asp Asp Ile His His Val Arg Lys Ser Met Glu Val Asn Phe
    130                 135                 140

Leu Ser Tyr Val Val Leu Thr Val Ala Ala Leu Pro Met Leu Lys Gln
145                 150                 155                 160

Ser Asn Gly Ser Ile Val Val Ser Ser Leu Ala Glu Thr Ala Met
                165                 170                 175

Lys Ala Val Ser Gly Ile Val His Met Gln Ala Ala Pro Lys Glu Glu
            180                 185                 190

Cys Ala Leu Glu Ile Ile Lys Gly Gly Ala Leu Arg Gln Glu Glu Val
        195                 200                 205

Tyr Tyr Asp Ser Ser Leu Trp Thr Thr Leu Leu Ile Arg Asn Pro Cys
    210                 215                 220

Arg Lys Ile Leu Glu Phe Leu Tyr Ser Thr Ser Tyr Asn Met Asp Arg
225                 230                 235                 240

Phe Ile Asn Lys

<210> SEQ ID NO 40
<211> LENGTH: 292
<212> TYPE: PRT
<213> ORGANISM: Mus musculus

<400> SEQUENCE: 40

Met Ala Val Met Lys Asn Tyr Leu Leu Pro Ile Leu Val Leu Phe Leu
1               5                   10                  15

Ala Tyr Tyr Tyr Tyr Ser Thr Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ser Lys Met Gly Ala His Val Val Leu Thr
    50                  55                  60
```

-continued

Ala Arg Ser Glu Glu Gly Leu Gln Lys Val Val Ser Arg Cys Leu Glu
 65                  70                  75                  80

Leu Gly Ala Ala Ser Ala His Tyr Ile Ala Gly Thr Met Glu Asp Met
                 85                  90                  95

Thr Phe Ala Glu Gln Phe Ile Val Lys Ala Gly Lys Leu Met Gly Gly
            100                 105                 110

Leu Asp Met Leu Ile Leu Asn His Ile Thr Gln Thr Ser Leu Ser Leu
        115                 120                 125

Phe His Asp Asp Ile His Ser Val Arg Arg Val Met Glu Val Asn Phe
    130                 135                 140

Leu Ser Tyr Val Val Met Ser Thr Ala Ala Leu Pro Met Leu Lys Gln
145                 150                 155                 160

Ser Asn Gly Ser Ile Ala Val Ile Ser Ser Leu Ala Gly Lys Met Thr
                165                 170                 175

Gln Pro Met Ile Ala Pro Tyr Ser Ala Ser Lys Phe Ala Leu Asp Gly
            180                 185                 190

Phe Phe Ser Thr Ile Arg Thr Glu Leu Tyr Ile Thr Lys Val Asn Val
        195                 200                 205

Ser Ile Thr Leu Cys Val Leu Gly Leu Ile Asp Thr Glu Thr Ala Met
    210                 215                 220

Lys Glu Ile Ser Gly Ile Ile Asn Ala Gln Ala Ser Pro Lys Glu Glu
225                 230                 235                 240

Cys Ala Leu Glu Ile Ile Lys Gly Thr Ala Leu Arg Lys Ser Glu Val
                245                 250                 255

Tyr Tyr Asp Lys Ser Pro Leu Thr Pro Ile Leu Leu Gly Asn Pro Gly
            260                 265                 270

Arg Lys Ile Met Glu Phe Phe Ser Leu Arg Tyr Tyr Asn Lys Asp Met
        275                 280                 285

Phe Val Ser Asn
    290

<210> SEQ ID NO 41
<211> LENGTH: 250
<212> TYPE: PRT
<213> ORGANISM: Mus musculus

<400> SEQUENCE: 41

Met Ala Val Met Lys Asn Tyr Leu Leu Pro Ile Leu Val Leu Phe Leu
  1               5                  10                  15

Ala Tyr Tyr Tyr Tyr Ser Thr Asn Glu Glu Phe Arg Leu Gln Lys Val
                 20                  25                  30

Val Ser Arg Cys Leu Glu Leu Gly Ala Ala Ser Ala His Tyr Ile Ala
             35                  40                  45

Gly Thr Met Glu Asp Met Thr Phe Ala Glu Gln Phe Ile Val Lys Ala
 50                  55                  60

Gly Lys Leu Met Gly Gly Leu Asp Met Leu Ile Leu Asn His Ile Thr
 65                  70                  75                  80

Gln Thr Ser Leu Ser Leu Phe His Asp Asp Ile His Ser Val Arg Arg
                 85                  90                  95

Val Met Glu Val Asn Phe Leu Ser Tyr Val Val Met Ser Thr Ala Ala
            100                 105                 110

Leu Pro Met Leu Lys Gln Ser Asn Gly Ser Ile Ala Val Ile Ser Ser
        115                 120                 125

Leu Ala Gly Lys Met Thr Gln Pro Met Ile Ala Pro Tyr Ser Ala Ser
    130                 135                 140

-continued

```
Lys Phe Ala Leu Asp Gly Phe Phe Ser Thr Ile Arg Thr Glu Leu Tyr
145                 150                 155                 160

Ile Thr Lys Val Asn Val Ser Ile Thr Leu Cys Val Leu Gly Leu Ile
                165                 170                 175

Asp Thr Glu Thr Ala Met Lys Glu Ile Ser Gly Ile Ile Asn Ala Gln
            180                 185                 190

Ala Ser Pro Lys Glu Glu Cys Ala Leu Glu Ile Ile Lys Gly Thr Ala
        195                 200                 205

Leu Arg Lys Ser Glu Val Tyr Tyr Asp Lys Ser Pro Leu Thr Pro Ile
    210                 215                 220

Leu Leu Gly Asn Pro Gly Arg Lys Ile Met Glu Phe Phe Ser Leu Arg
225                 230                 235                 240

Tyr Tyr Asn Lys Asp Met Phe Val Ser Asn
                245                 250

<210> SEQ ID NO 42
<211> LENGTH: 192
<212> TYPE: PRT
<213> ORGANISM: Mus musculus

<400> SEQUENCE: 42

Met Ala Val Met Lys Asn Tyr Leu Leu Pro Ile Leu Val Leu Phe Leu
1               5                   10                  15

Ala Tyr Tyr Tyr Ser Thr Asn Glu Glu Phe Arg Pro Glu Met Leu
                20                  25                  30

Gln Gly Lys Lys Val Ile Val Thr Gly Ala Ser Lys Gly Ile Gly Arg
            35                  40                  45

Glu Met Ala Tyr His Leu Ser Lys Met Gly Ala His Val Val Leu Thr
        50                  55                  60

Ala Arg Ser Glu Glu Gly Leu Gln Lys Val Val Ser Arg Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Ile Val Lys Ala Gly Lys Leu Met Gly Gly
            100                 105                 110

Leu Asp Met Leu Ile Leu Asn His Ile Thr Gln Thr Ser Leu Ser Leu
        115                 120                 125

Phe His Asp Asp Ile His Ser Val Arg Arg Val Met Glu Val Asn Phe
    130                 135                 140

Leu Ser Tyr Val Val Met Ser Thr Ala Ala Leu Pro Met Leu Lys Gln
145                 150                 155                 160

Ser Asn Gly Ser Ile Ala Val Ile Ser Ser Leu Ala Gly Gly Arg Thr
                165                 170                 175

Val Pro Gln Gln Arg Ser Arg Ser Val Thr Pro Asp Ser Arg Gly Pro
            180                 185                 190
```